(12) United States Patent
Rungta et al.

(10) Patent No.: US 10,975,005 B2
(45) Date of Patent: Apr. 13, 2021

(54) TRANSALKYLATION PROCESSES FOR CONVERTING AROMATIC HYDROCARBONS COMPRISING ALKYL-DEMETHYLATION

(71) Applicant: ExxonMobil Chemical Patents Inc., Baytown, TX (US)

(72) Inventors: Meha Rungta, Houston, TX (US); Michel Molinier, Houston, TX (US); Hari Nair, Spring, TX (US); Doron Levin, Highland Park, NJ (US); Scott J. Weigel, Allentown, PA (US); Michael Salciccioli, Ann Arbor, MI (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/903,058

(22) Filed: Jun. 16, 2020

(65) Prior Publication Data
US 2021/0017103 A1 Jan. 21, 2021

Related U.S. Application Data

(60) Provisional application No. 62/876,445, filed on Jul. 19, 2019.

(51) Int. Cl.
*C07C 6/06* (2006.01)
*C07C 4/18* (2006.01)
(Continued)

(52) U.S. Cl.
CPC .................. *C07C 6/06* (2013.01); *C07C 4/18* (2013.01); *C07C 5/2754* (2013.01); *C07C 7/005* (2013.01); *C07C 15/08* (2013.01)

(58) Field of Classification Search
CPC .... C10G 2400/30; C10G 35/04; C10G 45/68; C10G 2300/104; C10G 29/205; C10G 35/00; C10G 35/095; C10G 50/00; C10G 59/00; C10G 69/00; C10G 69/04; C10G 69/08; C10G 69/14; B01J 19/24; B01J 19/2445; B01J 19/245; B01J 2219/24; B01J 29/40; B01J 29/48; B01J 29/7469; B01J 29/80; B01J 35/0006; B01J 37/0009; B01J 37/10; C07C 15/08; C07C 7/005;
(Continued)

(56) References Cited

U.S. PATENT DOCUMENTS

| 3,919,339 A | 11/1975 | Ransley |
| 2015/0368571 A1 | 12/2015 | Mehlberg et al. |

(Continued)

FOREIGN PATENT DOCUMENTS

WO 2019/112769 6/2019

OTHER PUBLICATIONS

Nair et al. U.S. Appl. No. 62/876,391, filed Jul. 19, 2019.
Molinier et al. U.S. Appl. No. 62/876,426, filed Jul. 19, 2019.

*Primary Examiner* — Sharon Pregler

(57) ABSTRACT

Alkyl-demethylation of C2+-hydrocarbyl substituted aromatic hydrocarbons can be utilized to treat one or more of a heavy naphtha reformate stream, a hydrotreated SCN stream, a C8 aromatic hydrocarbon isomerization feed stream, a C9+ aromatic hydrocarbon transalkylation feed stream, and similar hydrocarbon streams to produce additional quantity of xylene products.

23 Claims, 6 Drawing Sheets

(51) Int. Cl.
*C07C 7/00* (2006.01)
*C07C 5/27* (2006.01)
*C07C 15/08* (2006.01)

(58) Field of Classification Search
CPC .. C07C 15/06; C07C 4/08; C07C 4/12; C07C 4/18; C07C 5/2732; C07C 6/04; C07C 6/06
See application file for complete search history.

(56) References Cited

U.S. PATENT DOCUMENTS

2015/0376086 A1* 12/2015 Tinger .................... C07C 2/864
585/314
2016/0046544 A1* 2/2016 Molinier ............... C07C 5/2732
585/319

* cited by examiner

TRANSALKYLATION PROCESSES FOR CONVERTING AROMATIC HYDROCARBONS COMPRISING ALKYL-DEMETHYLATION

CROSS-REFERENCE TO RELATED APPLICATIONS

This application claims priority to and the benefit of U.S. Ser. No. 62/876,445, filed Jul. 19, 2019, the disclosure of which is incorporated herein by reference.

FIELD

This disclosure relates to processes for converting aromatic hydrocarbons such as processes for making xylenes, isomerizing C8 aromatic hydrocarbons, and transalkylating aromatic hydrocarbons. In particular, this disclosure relates to such processes comprising alkyl-demethylating an aromatic hydrocarbon having a C2+-alkyl substitute attached to an aromatic ring therein or an aliphatic ring annelated to an aromatic ring therein. This disclosure is useful for producing, e.g., xylenes (e.g., p-xylene, o-xylene, and/or mixed xylenes), from a naphtha reformer effluent and/or a hydrotreated steam-cracked naphtha stream produced in a petrochemical plant.

BACKGROUND

Para-xylene ("p-xylene") is an important industrial commodity for making terephthalic acid, which is then used for making large quantities of polyester fibers. Ortho-xylene ("o-xylene") is another important industrial commodity for making phthalic acid, which is then used for making plasticizers and other industrial materials. Large quantities of p-xylene and o-xylene are consumed worldwide every year. The high demands of these two aromatic hydrocarbons has led to the advancement of many technologies for their large-scale fabrication. o-Xylene and p-xylene are quite often present in C8 aromatic hydrocarbon mixtures additionally comprising their isomers including meta-xylene and ethylbenzene at various quantities. Separation of a p-xylene product from such C8 aromatic hydrocarbon mixtures can be effected by using, e.g., crystallization and adsorption chromatography-based technologies. The residual filtrate from crystallization-separation and the raffinate from the adsorption chromatography-based technology (collectively the "raffinate") are depleted in p-xylene and rich in m-xylene and o-xylene. Typically the raffinate is then isomerized in contacting an isomerization catalyst in an isomerization reactor to convert a portion of the m-xylene and o-xylene to p-xylene, from which additional p-xylene can be separated in the xylenes loop.

In a petrochemical plant, a major source of the C8 aromatic hydrocarbon mixtures is a C6+ hydrocarbon reformate stream produced from a heavy naphtha reforming reactor ("reformer"). In the presence of a reforming catalyst under reforming conditions, the paraffins and aromatic hydrocarbons contained in the heavy naphtha feed supplied to the reformer undergo complex chemical reactions such as isomerization, dehydrogenation, dehydrocyclization, aromatization, and the like, to yield a reforming mixture comprising more branched paraffins, aromatic hydrocarbons, and hydrogen. A C6+ hydrocarbon reformate stream separated from the reforming mixture comprises benzene, toluene, C8 aromatics, and C9+ aromatics. The C8 aromatics typically comprise, in addition to the xylenes, ethylbenzene at substantial quantity. The C9+ aromatics typically comprise, in addition to aromatic hydrocarbons comprising only methyl substitutes attached to the aromatic ring therein, aromatic hydrocarbons comprising C2+ alkyl group(s) (e.g., ethylmethylbenzenes, diethylbenzenes, C3-alkylbenzenes, and the like) and/or aromatic hydrocarbons comprising an aliphatic ring annelated to an aromatic ring (e.g., indane, methylindanes, tetralin, methyltetralins, and the like).

Thus the raffinate subject to isomerization described above derived from a reformate stream typically comprises ethylbenzene at significant quantity. It is difficult to convert ethylbenzene directly to xylenes in an isomerization reactor. To prevent ethylbenzene accumulation in the xylenes loop and to convert ethylbenzene into more valuable products, a known strategy is to conduct the isomerization process under vapor-phase conditions and in the presence of a catalyst effective to de-ethylate ethylbenzene. The removed ethyl group from ethylbenzene forms light hydrocarbons in the presence of hydrogen in the isomerization reactor. Vapor-phase isomerization is energy intensive. It would be beneficial if at least a portion of the ethyl group is converted into methyl group attached to a benzene ring so that more valuable products such as xylenes can be produced.

To maximize the production of xylenes, the C9+ aromatics in the C6+ reformate stream can be separated and then supplied to a transalkylation reactor together with benzene and/or toluene. In the presence of a transalkylation catalyst and under transalkylation conditions, the C9+ aromatics exchanges methyl groups with benzene/toluene to produce more xylenes. To convert the C9+ aromatics comprising C2+ alkyl substitute(s) and/or an aliphatic ring to useful products such as xylenes, a strategy is to conduct transalkylation in vapor phase in the presence of a catalyst effective to dealkylate such C2+ alkyl substitutes. The removed alkyl groups form light hydrocarbons in the presence of hydrogen in the transalkylation reactor. Vapor-phase transalkylation is energy intensive. It would be beneficial if at least a portion of the C2+ group(s) and the aliphatic ring(s) are converted into methyl group attached to a benzene ring so that more valuable products such as xylenes can be produced.

C8 aromatic hydrocarbons are also present in hydrotreated steam cracked naphtha ("SCN"). However, traditionally hydrotreated SCN streams are not considered as economic source materials for producing xylene products due to the high concentrations of ethylbenzene and indane therein. It would be highly desirable to develop a process to produce xylene products from hydrotreated SCN streams.

There are still needs for more energy efficient processes such as C8 aromatic hydrocarbons isomerization process and C9+ aromatic hydrocarbon transalkylation process for producing more xylenes, particularly p-xylene, from a reformate stream and other similar aromatic hydrocarbon sources such as hydrotreated SCN streams. This disclosure satisfies this and other needs.

SUMMARY

It has been found that an alkyl-demethylation process can be used to selectively convert C2+-hydrocarbyl-substituted aromatic hydrocarbons comprising a C2+ alkyl group attached to an aromatic ring therein or an aliphatic ring annelated to an aromatic ring therein to produce alkyl-demethylated hydrocarbons, particularly methylated aromatic hydrocarbons. Incorporating an alkyl-demethylation process into the aromatic hydrocarbon production processes such as a transalkylation process (particularly a liquid-phase transalkylation process) can have at least one of the following advantages: (i) improved energy efficiency; (ii) increased production of more valuable products such as xylenes (vs. benzene); (iii) improved carbon utilization (lower fuel gas make, higher overall product yield); and (iv) simplified process, equipment, and system.

A first aspect of this disclosure relates to a transalkylation process, the process comprising one or more of: (A) providing a C9+ aromatic hydrocarbon stream comprising a C2+-hydrocarbyl-substituted aromatic hydrocarbon, wherein the C2+-hydrocarbyl-substituted aromatic hydrocarbon has (i) a C2+ alkyl substitute attached to an aromatic ring therein and/or (ii) an aliphatic ring annelated to an aromatic ring therein; (B) optionally contacting at least a portion of the C9+ aromatic hydrocarbon stream with an alkyl-demethylation catalyst No. 1 in an alkyl-demethylation zone No. 1 under a set of alkyl-demethylation conditions No. 1 to convert at least a portion of the C2+-hydrocarbyl-substituted aromatic hydrocarbon contained in the C9+ aromatic hydrocarbon stream to an alkyl-demethylated hydrocarbon to produce an alkyl-demethylated effluent No. 1 exiting the alkyl-demethylation zone No. 1; (C) optionally separating the C9+ aromatic hydrocarbons stream and/or the alkyl-demethylated effluent No. 1 in a separation device No. 1 to obtain a C9-C10 aromatic hydrocarbons-rich stream and a C11+ aromatic hydrocarbons-rich stream; (D) optionally contacting at least a portion of the alkyl-demethylated effluent No. 1 and/or at least a portion of the C9-C10 aromatic hydrocarbons-rich stream with an alkyl-demethylation catalyst No. 2 in an alkyl-demethylation zone No. 2 under a set of alkyl-demethylation conditions No. 2 to convert at least a portion of the C2+-hydrocarbyl-substituted aromatic hydrocarbon, if any, contained in the alkyl-demethylated effluent No. 1 and/or the C9-C10 aromatic hydrocarbons-rich stream to an alkyl-demethylated hydrocarbon to produce an alkyl-demethylated effluent No. 2 exiting the alkyl-demethylation zone No. 2; (E) feeding at least a portion of the C9+ aromatic hydrocarbons stream, and/or at least a portion of the alkyl-demethylated effluent No. 1, and/or at least a portion of the C9-C10 aromatic hydrocarbons-rich stream, and/or at least a portion of the alkyl-demethylated effluent No. 2, and an optional benzene/toluene stream to a transalkylation zone; (F) contacting C9+ aromatic hydrocarbons with benzene/toluene in the presence of a transalkylation catalyst in the transalkylation zone under transalkylation conditions to produce a transalkylation effluent exiting the transalkylation zone; and (G) separating the transalkylation effluent in a separation device No. 2 to obtain an optional benzene product stream, a toluene-rich stream, and a C8+ aromatic hydrocarbons-rich stream; wherein at least one of steps (B) and (D) is carried out.

A second aspect of this disclosure relates to a process for converting aromatic hydrocarbons, the process comprising at least one of the following: (A) providing a C9+ aromatic hydrocarbon stream comprising a C2+-hydrocarbyl-substituted aromatic hydrocarbon, wherein the C2+-hydrocarbyl-substituted aromatic hydrocarbon has (i) a C2+ alkyl substitute attached to an aromatic ring therein and/or (ii) an aliphatic ring annelated to an aromatic ring therein; (B) optionally contacting at least a portion of the C9+ aromatic hydrocarbon stream with an alkyl-demethylation catalyst No. 1 in an alkyl-demethylation zone No. 1 under a set of alkyl-demethylation conditions No. 1 to convert at least a portion of the C2+-hydrocarbyl-substituted aromatic hydrocarbon contained in the C9+ aromatic hydrocarbon stream to an alkyl-demethylated hydrocarbon to produce an alkyl-demethylated effluent No. 1 exiting the alkyl-demethylation zone No. 1; (C) optionally separating the C9+ aromatic hydrocarbons stream and/or the alkyl-demethylated effluent No. 1 in a separation device No. 1 to obtain a C9-C10 aromatic hydrocarbons-rich stream and a C11+ aromatic hydrocarbons-rich stream; (D) optionally contacting at least a portion of the alkyl-demethylated effluent No. 1 and/or at least a portion of the C9-C10 aromatic hydrocarbons-rich stream with an alkyl-demethylation catalyst No. 2 in an alkyl-demethylation zone No. 2 under a set of alkyl-demethylation conditions No. 2 to convert at least a portion of the C2+-hydrocarbyl-substituted aromatic hydrocarbon, if any, contained in the alkyl-demethylated effluent No. 1 and/or the C9-C10 aromatic hydrocarbons-rich stream to an alkyl-demethylated hydrocarbon to produce an alkyl-demethylated effluent No. 2 exiting the alkyl-demethylation zone No. 2; (E) feeding at least a portion of the C9+ aromatic hydrocarbons stream, and/or at least a portion of the alkyl-demethylated effluent No. 1, and/or at least a portion of the C9-C10 aromatic hydrocarbons-rich stream, and/or at least a portion of the alkyl-demethylated effluent No. 2, and an optional benzene/toluene stream to a transalkylation zone; (F) contacting C9+ aromatic hydrocarbons with benzene/toluene in the presence of a transalkylation catalyst in the transalkylation zone under transalkylation conditions to produce a transalkylation effluent exiting the transalkylation zone; and (G) separating the transalkylation effluent in a separation device No. 2 to obtain an optional benzene product stream, a toluene-rich stream, and a C8+ aromatic hydrocarbons-rich stream; wherein at least one of the following is met: (i) at least one of steps (B) and (D) is carried out; (ii) the set of alkyl-demethylation conditions No. 1 and the set of alkyl-demethylation conditions No. 2, the same or different, comprise at least one of: a temperature in a range from 200 to 500° C.; an absolute pressure in a range from 350 to 2500 kilopascal; a molar ratio of molecular hydrogen to hydrocarbon in a range from 0.5 to 20; and a liquid weight hourly space velocity in a range from 1 to 20 hour$^{-1}$; and (iii) the first alkyl-demethylation catalyst and/or the second alkyl-demethylation catalyst, the same or different, comprises a first metal element selected from groups 7, 8, 9, and 10 metals and combinations thereof, and a support.

DETAILED DESCRIPTION

Figure 1:
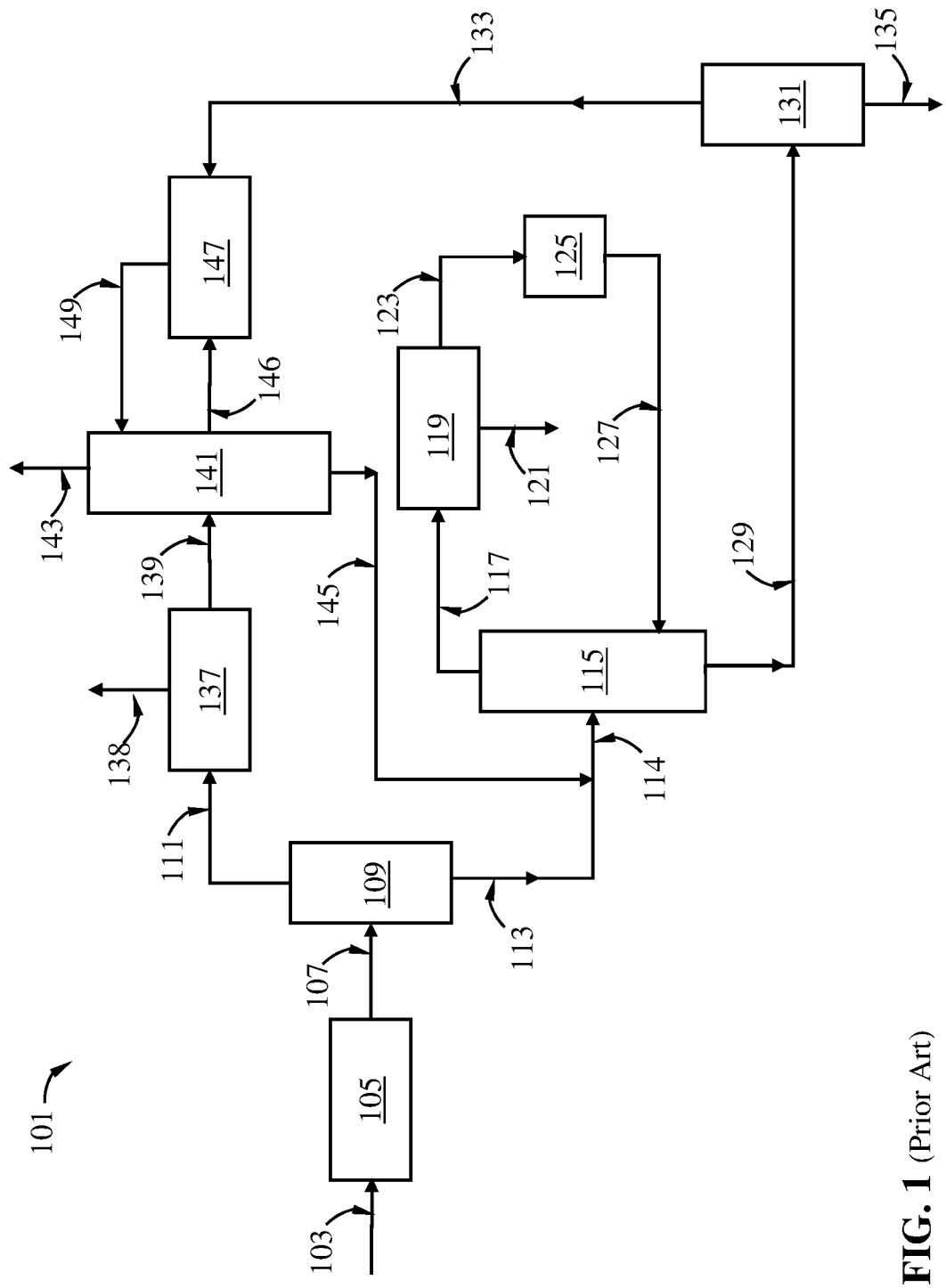
FIG. 1 is a schematic diagram showing a prior art process for producing p-xylene from naphtha reforming including a xylenes loop and a transalkylation step.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used.

"Consisting essentially of" as used herein means the composition, feed, or effluent comprises a given component at a concentration of at least 60 wt %, preferably at least 70 wt %, more preferably at least 80 wt %, more preferably at least 90 wt %, still more preferably at least 95 wt %, based on the total weight of the composition, feed, or effluent in question.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a C2 hydrocarbon can be ethane, ethylene, acetylene, or mixtures of at least two of them at any proportion. A "Cm to Cn hydrocarbon" or "Cm-Cn hydrocarbon," where m and n are positive integers and m<n, means any of Cm, Cm+1, Cm+2, . . . , Cn-1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

"Light hydrocarbon" in this disclosure means any C5− hydrocarbon.

"Liquid-phase isomerization" means a C8 aromatic hydrocarbon isomerization process in an isomerization zone in the presence of an isomerization catalyst whereby the xylenes (e.g., a p-xylene-depleted and/or o-xylene-depleted xylenes mixture) isomerize under isomerization conditions such that the aromatic hydrocarbons present in the isomerization zone are substantially in liquid phase. "Substantially in liquid phase" means ≥90 wt % preferably ≥95 wt %, preferably ≥99 wt %, preferably the entirety, is in liquid phase. Such isomerization conditions are called liquid-phase isomerization conditions.

"Vapor-phase isomerization" means a C8 aromatic hydrocarbon isomerization process in an isomerization zone in the presence of an isomerization catalyst whereby the xylenes (e.g., a p-xylene-depleted and/or o-xylene-depleted xylenes mixture) isomerize under isomerization conditions such that the aromatic hydrocarbons present in the isomerization zone are substantially in vapor phase. "Substantially in vapor phase" means ≥90 wt %, preferably ≥95 wt %, preferably ≥99 wt %, preferably the entirety, is in vapor phase. Such isomerization conditions are called vapor-phase isomerization conditions.

"Liquid-phase transalkylation" means a transalkylation process between aromatic hydrocarbons (e.g., between a light aromatic hydrocarbon such as benzene and/or toluene and a heavy aromatic hydrocarbon such as a C9+ aromatic hydrocarbon, or between two toluene molecules) in the presence of a transalkylation catalyst in a transalkylation zone whereby the aromatic hydrocarbons exchange substitutes attached to aromatic rings therein under transalkylation conditions such that the aromatic hydrocarbons present in the transalkylation zone are substantially in liquid phase. "Substantially in liquid phase" means ≥90 wt %, preferably ≥95 wt %, preferably ≥99 wt %, preferably the entirety, is in liquid phase. Such transalkylation conditions are called liquid-phase transalkylation conditions. Thus, a toluene disproportionation process whereby toluene is converted into xylenes and benzene is a specific type of transalkylation process.

"Vapor-phase transalkylation" means a transalkylation process between aromatic hydrocarbons (e.g., between a light aromatic hydrocarbon such as benzene and/or toluene and a heavy aromatic hydrocarbon such as a C9+ aromatic hydrocarbon, or between two toluene molecules) in the presence of a transalkylation catalyst in a transalkylation zone whereby the aromatic hydrocarbons exchange substitutes attached to aromatic rings therein under transalkylation conditions such that the aromatic hydrocarbons present in the transalkylation zone are substantially in vapor phase. "Substantially in vapor phase" means ≥90 wt %, preferably ≥95 wt %, preferably ≥99 wt %, preferably the entirety, is in vapor phase. Such transalkylation conditions are called vapor-phase transalkylation conditions. Thus, a toluene disproportionation process whereby toluene is converted into xylenes and benzene is a specific type of transalkylation process.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All concentrations herein are expressed on the basis of the total amount of the composition in question. All ranges expressed herein should include both end points as two specific embodiments unless specified or indicated to the contrary.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

"Methylated aromatic hydrocarbon" means an aromatic hydrocarbon comprising at least one methyl group and only methyl group(s) attached to the aromatic ring(s) therein. Examples of methylated aromatic hydrocarbons are: toluene; xylenes; trimethylbenzenes; tetramethylbenzenes; pentamethylbenzene; hexamethylbenzene; methylnaphthalenes; dimethylnaphthalenes; trimethylnaphthalenes; tetramethylnaphthalenes; and the like.

"C2+-hydrocarbyl-substituted aromatic hydrocarbon" means an aromatic hydrocarbon comprising a substituted aromatic ring, other than a methylated aromatic hydrocarbon. A C2+-hydrocarbyl-substituted aromatic hydrocarbon may comprise (i) a C2+-hydrocarbyl group (e.g., a C2+-alkyl group) attached to an aromatic ring therein and/or (ii) an aliphatic ring annelated to an aromatic ring therein. Examples of C2+-hydrocarbyl-substituted aromatic hydrocarbons in scenario (i) include, but are not limited to: ethylbenzene (C8); ethylmethylbenzenes (C9); n-propylbenzene (C9); cumene (C9); ethyldimethylbenzenes (C10); diethylbenzenes (C10); n-propylmethylbenzenes (C10); methylcumenes (i.e., isopropylmethylbenzenes, C10); n-butylbenzene (C10); sec-butylbenzene (C10); tert-butylbenzene (C10); and the like. Examples of C2+-hydrocarbyl-substituted aromatic hydrocarbons in scenario (ii) include, but are not limited to: indane (C9); indene (C9); methylindanes (C10); methylindenes (C10); tetralin (C10); methyltetralin (C11), dimethylindanes (C11); ethylindanes (C11); and the like. Benzene and naphthalene are neither methylated aromatic hydrocarbon nor C2+-hydrocarbyl-substituted aromatic hydrocarbon.

"Alkyl-demethylation" means, in the presence of an alkyl-demethylation catalyst and molecular hydrogen, (i) the removal of one or more carbon atoms from a Cm (m ≥ 2) alkyl group attached to an aromatic ring to leave a Cm' residual alkyl group attached to the aromatic ring, wherein 1 ≤ m' ≤ m−1, preferably m'=1; or (ii) the removal of one or more carbon atoms from a Cn aliphatic ring annelated to an aromatic ring to leave one or more residual alkyl groups (preferably methyl) comprising n' carbon atoms in total, wherein 1 ≤ n' ≤ n−2. Reactions (i) and (ii) are collectively called "alkyl-demethylation reactions" in this disclosure. Thus, alkyl-demethylation of a C2+-hydrocarbyl-substituted aromatic hydrocarbon comprising a Cm (m ≥ 2) alkyl group attached to an aromatic ring therein can result in an aromatic hydrocarbon substituted by a Cm−1 alkyl group, or a Cm−2 alkyl group, . . . , or a methyl group, as an alkyl-demethylated hydrocarbon. Alkyl-demethylation of a C2+-hydrocarbyl-substituted aromatic hydrocarbon comprising an n-member (n ≥ 5) aliphatic ring annelated to an aromatic ring therein can result in aromatic hydrocarbons substituted by at least one substitutes (preferably two methyls) taken together having n−2, n−3, n−4, . . . , or 1 carbon atoms. The removed methyl group(s) forms light hydrocarbon(s) (preferably methane) in the presence of molecular hydrogen. With respect to C2+-hydrocarbyl-substituted aromatic hydrocarbons, the alkyl-demethylation catalyst is desirably selective toward alkyl-demethylation defined above over (i) the removal of the Cn (n ≥ 2) group attached to an aromatic ring in its entirety leaving no residual substitute and (ii) the removal of methyl group attached to an aromatic ring leaving no residual substitute. Thus, further alkyl-demethylation of the alkyl-demethylated hydrocarbon(s) which are also C2+-hydrocarbyl-substituted aromatic hydrocarbons can result in increased amount of methylated aromatic hydrocarbons (e.g., tetramethylbenzenes, trimethylbenzenes, xylenes, and toluene). Without intending to be bound by a particular theory, such methylated aromatic hydrocarbons can be produced from C2+-hydrocarbyl aromatic hydrocarbons with or without the formation of the alkyl-demethylated hydrocarbons as intermediate C2+-hydrocarbyl aromatic hydrocarbons. Desirably, treating an aromatic hydrocarbon feed mixture comprising C2+-hydrocarbyl-substituted aromatic hydrocarbons by alkyl-demethylation produces an aromatic hydrocarbon product mixture having a higher methyl to aromatic ring molar ratio compared to the feed mixture. Examples of alkyl-demethylation reactions of C2+-hydrocarbyl-substituted aromatic hydrocarbons to produce alkyl-demethylated hydrocarbon(s) include, but are not limited to the following:

| C2+-hydrocarbly-substituted aromatic hydrocarbon | Alkyl-demethylated hydrocarbon(s) |
|---|---|
| Ethylbenzene | Toluene |
| n-Propylbenzene | Ethylbenzene; toluene |
| Cumene | Ethylbenzene; toluene |
| Ethylmethylbenzenes | Xylenes |
| Indane | Ethylmethylbenzenes; n-propylbenzene; cumene; ethylbenzene; xylenes; toluene |
| 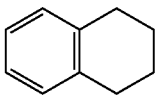 (methylindanes) | Indane; propylmethylbenzenes; diethylbenzenes; ethylmethylbenzenes; butylbenzenes; n-propylbenzene; cumene; ethylbenzene; xylenes; toluene |
| 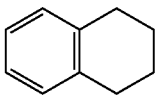 (methylindanes) | Ethylmethylbenzenes; ethyldimethylbenzene; trimethylbenzenes; butylmethylbenzenes; propylmethylbenzenes; xylenes |
| 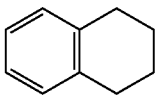 (tetralin) | Propylmethylbenzenes, diethylbenzene, butylbenzenes; n-propylbenzene; cumene; ethylmethylbenzenes; xylenes; ethylbenzene; toluene |

"Dealkylation" of an alkyl group attached to an aromatic ring means the removal of the alkyl group in its entirety leaving no residual group attached to the aromatic ring. Thus, demethylation of the methyl group in toluene to form benzene, deethylation of the ethyl group in ethylbenzene to form benzene, deethylation of the ethyl group in ethylmethylbenzenes to form toluene, and the depropylation of the isopropyl group in cumene to form benzene are a specific forms of dealkylation. Dealkylation of an alkylated aromatic hydrocarbon is typically effected in the presence of a dealkylation catalyst selective for dealkylation over alkyl-demethylation discussed above in the presence of molecular hydrogen. The removed alkyl group in the dealkylation reaction forms light hydrocarbon(s) in the presence of molecular hydrogen.

An effluent or a feed is sometimes also called a stream in this disclosure. Where two or more streams are shown to form a join stream and then supplied into a vessel, it should be interpreted to include alternatives where the streams are supplied separately to the vessel where appropriate. Likewise, where two or more streams are supplied separately to a vessel, it should be interpreted to include alternatives where the streams are combined before entering into the vessel as joint stream(s) where appropriate.

The Alkyl-Demethylation Processes of this Disclosure

An alkyl-demethylation process occurs in the presence of an alkyl-demethylation catalyst under a set of alkyl-demethylation conditions in an alkyl-demethylation zone. On contacting the alkyl-demethylation catalyst, a $Cm+(m \geq 2)$ alkyl group attached to an aromatic ring (e.g., a benzene ring, a naphthalene ring, and the like) loses one or more distal carbon atoms (i.e., the carbon atom from the alkyl group on the aromatic ring) to form preferably a methylated aromatic hydrocarbon with a methyl group attached to the aromatic ring. Preferably, the alkyl-demethylation catalyst favors alkyl-demethylation of a Cm ($m \geq 2$) alkyl group attached to an aromatic ring over the demethylation of a methyl group attached to an aromatic ring under the alkyl-demethylation conditions. Thus, alkyl-demethylation of ethylbenzene (i.e., ethyl-demethylation) results in the net production of toluene, further demethylation of which to produce benzene is not favored. Alkyl-demethylation of ethylmethylbenzenes results in the net production of xylenes, further demethylation of which to produce toluene and benzene is not favored. Similarly, alkyl-demethylation of C3-alkylbenzenes (i.e., benzene substituted by a single C3-alkyl group) preferably produces toluene. Alkyl-demethylation of C3-alkylmethylbenzenes preferably results in the net production of xylenes. Thus, alkyl-demethylation processes favor the production of methylated aromatic hydrocarbons (toluene, xylenes, trimethylbenzenes, and the like) over the production of benzene. A process for converting aromatic hydrocarbons of this disclosure can advantageously comprises one or more alkyl-demethylation process steps.

In the presence of the alkyl-demethylation catalyst and under the alkyl-demethylation conditions, aromatic hydrocarbons comprising an aliphatic ring annelated to an aromatic ring (e.g., indane, methylindanes, tetralin, methyltetralins, and the like) may undergo scission of the aliphatic ring to form one or more linear or branched residual groups attached to the aromatic ring with or without first losing a carbon atom from the aliphatic ring. Any C2+ linear or branched residual alkyl group may undergo one or more steps of alkyl-demethylation reactions to be eventually converted into a methyl group attached to the aromatic ring, the further demethylation of which is disfavored. Thus, those C2+-hydrocarbyl-substituted aromatic hydrocarbons such as indane, methylindanes, tetralin, and methyltetralins can be converted into methylated aromatic hydrocarbons in the alkyl-demethylation processes. In the processes of this disclosure including an alkyl-demethylation step in an alkyl-demethylation zone, preferably the alkyl-demethylation catalyst is capable of catalyzing the scission of aliphatic ring(s) annelated to an aromatic ring. In case the alkyl-demethylation catalyst is not sufficiently active in catalyzing the scission of the aliphatic ring, an additional catalyst selective for the scission of the aliphatic ring may be included in the alkyl-demethylation zone as well.

While alkyl-demethylation reactions as described above are favored in the alkyl-demethylation process of this disclosure, it should be understood that certain side reactions other than the alkyl-demethylation reactions may occur to a certain degree in the presence of the alkyl-demethylation catalyst under the alkyl-demethylation reaction conditions in the alkyl-demethylation zone.

The hydrocarbon feed supplied to an alkyl-demethylation zone in the process of this disclosure comprises C2+-hydrocarbyl-substituted aromatic hydrocarbons. The concentration of the C2+-hydrocarbyl-substituted aromatic hydrocarbons in the feed can range from c1 to c2 wt %, based on the total weight of the C6+ aromatics in the feed to the zone, wherein c1 and c2 can be, independently, e.g., 2, 4, 5, 6, 8, 10, 15, 20, 25, 30, 35, 40, 45, 50, 55, 60, 65, 70, 75, 80, 85, 90, as long as c1<c2. Thus the feed subject to alkyl-demethylation can comprise such C2+-hydrocarbyl-substituted aromatic hydrocarbons at relatively low to very high concentrations, depending on the source of the feed.

In certain embodiments, the hydrocarbon feed supplied to the alkyl-demethylation zone can comprise C8 aromatics including ethylbenzene and xylenes at various concentrations. In certain embodiments, the concentration of ethylbenzene in the feed (e.g., a p-xylene depleted feed produced from a p-xylene separation sub-system in the processes described below in connection with the drawings) to the alkyl-demethylation zone can range from c(EB)1 to c(EB)2 wt %, based on the total weight of the C8 aromatic hydrocarbons contained in the feed, wherein c(EB)1 and c(EB)2 can be, independently, e.g., 2, 4, 5, 6, 8, 10, 15, 20, 25, 30, 35, 40, 45, or 50, as long as c(EB)1<c(EB)2. The processes of this disclosure can be particularly advantageously used to process such streams comprising high concentrations of ethylbenzene such as at $\geq 10$ wt %, $\geq 20$ wt %, or $\geq 30$ wt %, based on the weight of all C8 aromatic hydrocarbons in the feed, to produce toluene. Toluene can be converted into additional quantities of xylenes, particularly p-xylene, via methylation with methanol and/or dimethyl ether, toluene disproportionation, and transalkylation with C9+ aromatic hydrocarbons, particularly methylated aromatic hydrocarbons such as trimethylbenzenes and tetramethylbenzenes.

In certain embodiments, the hydrocarbon feed supplied to the alkyl-demethylation zone can comprise C9+ aromatic hydrocarbons including methylethylbenzenes, C3-alkyl substituted benzenes, indane, trimethylbenzenes, C4-alkyl substituted benzenes, methylindanes, tetramethylbenzenes, tetralin, methyltetralins, and the like, at various concentrations. In certain embodiments, the concentration of C9+C2+-hydrocarbyl-substituted aromatic hydrocarbons in the feed (e.g., a C9+ aromatic hydrocarbons-rich stream produced from a xylenes splitter as described in the processes described below in connection with the drawings) to the alkyl-demethylation zone can range from cx1 to cx2 wt %, based on the total weight of the C9+ aromatic hydrocarbons contained in the feed, wherein cx1 and cx2 can be, independently, e.g., 10, 15, 20, 25, 30, 35, 40, 45, 50, 55, 60, 65, 70, 75, 80, 85, or 90, as long as cx1<cx2. The processes of this disclosure can be particularly advantageously used to process such streams comprising high concentrations of C9+C2+-hydrocarbyl-substituted aromatic hydrocarbons such as at ≥30 wt %, ≥40 wt %, or ≥40 wt %, ≥50 wt %, ≥60 wt %, ≥70 wt %, ≥80 wt %, based on the weight of all C8 aromatic hydrocarbons in the feed. Large quantities of C9+C2+-hydrocarbyl-substituted aromatic hydrocarbons can be conveniently converted into useful methylated aromatic hydrocarbons such as toluene, xylenes, and trimethylbenzenes. Toluene can be converted into additional quantities of xylenes, particularly p-xylene, via methylation with methanol and/or dimethyl ether, toluene disproportionation, and transalkylation with C9+ aromatic hydrocarbons, particularly methylated aromatic hydrocarbons such as trimethylbenzenes and tetramethylbenzenes. C9+ methylated aromatic hydrocarbons, including trimethylbenzenes, tetramethylbenzenes, and the like, can be converted into additional quantities of xylenes, particularly p-xylene, via transalkylation with benzene and/or toluene.

The alkyl-demethylation step is preferably carried out in the presence of molecular hydrogen co-fed into the alkyl-demethylation zone. The methyl group(s) removed in the alkyl-demethylation step is converted into light hydrocarbons such as methane in the presence of molecular hydrogen.

The processes of this disclosure can include one or more alkyl-demethylation zones. An alkyl-demethylation zone can include a portion of a reactor, a full reactor, or multiple reactors. Where multiple alkyl-demethylation zones are present in a process of this disclosure, the alkyl-demethylation catalysts and conditions in them may be the same or different.

The alkyl-demethylation conditions (e.g., the first, second, third, fourth, fifth, sixth, and seventh alkyl-demethylation conditions) in the alkyl-demethylation zones can vary widely, depending on the composition of the feed subject to alkyl-demethylation. Even in a single alkyl-demethylation zone, the alkyl-demethylation conditions can vary widely during a production campaign, or from one production campaign to another. Thus, the alkyl-demethylation conditions can include a temperature in a range from t1 to t2° C., wherein t1 and t2 can be, independently, e.g.: 200, 220, 240, 250, 260, 280, 300, 320, 340, 350, 360, 380, 400, 420, 440, 450, 460, 480, or 500, as long as t1<t2. The alkyl-demethylation conditions can include an absolute pressure in the alkyl-demethylation zone in a range from p1 to p2 kilopascal, wherein p1 and p2 can be, independently, e.g.: 350, 400, 450, 500, 550, 600, 650, 700, 750, 800, 850, 900, 950, 1000, 1200, 1400, 1500, 1600, 1800, 2000, 2200, 2400, or 2500, as long as p1<p2. Thus, the alkyl-demethylation conditions can be such that the aromatic hydrocarbons in the alkyl-demethylation zone are substantially in vapor phase, substantially in liquid phase, or a mixed phase. The alkyl-demethylation conditions can include a molecular hydrogen to hydrocarbons molar ratio in a range from r1 to r2, where r1 and r2 can be, independently, e.g., 0.5, 1, 2, 3, 4, 5, 6, 7, 8, 9, 10, 11, 12, 13, 14, 15, 16, 17, 18, 19, 20, as long as r1<r2. The alkyl-demethylation conditions can further include a liquid weight hourly space velocity ("WHSV") in a range from w1 to w2, where w1 and w2 can be, independently, e.g., 0.1, 0.2, 0.4, 0.5, 0.6, 0.8, 1, 2, 4, 5, 6, 8, 10, 12, 14, 15, 16, 18, or 20, as long as w1<w2.

Specifically, with respect to a C8 aromatic hydrocarbon stream comprising a majority by weight, or consisting essentially of, xylenes and ethylbenzene, such as a p-xylene depleted stream produced from a p-xylene separation subsystem described below in connection with the drawings, the alkyl-demethylation conditions can include a temperature in a range from t3 to t4° C., wherein t3 and t4 can be, independently, e.g.: 200, 220, 240, 250, 260, 280, 300, 320, 340, 350, 360, 380, 400, 420, 440, 450, 460, 480, or 500, as long as t3<t4. The alkyl-demethylation conditions can include an absolute pressure in the alkyl-demethylation zone in a range from p3 to p4 kilopascal, wherein p3 and p4 can be, independently, e.g.: 350, 400, 450, 500, 550, 600, 650, 700, 750, 800, 850, 900, 950, 1000, 1200, 1400, 1500, 1600, 1800, 2000, 2200, 2400, or 2500, as long as p3<p4. Thus, the alkyl-demethylation conditions can be such that the C8 aromatic hydrocarbons in the alkyl-demethylation zone are substantially in vapor phase, substantially in liquid phase, or a mixed phase. The alkyl-demethylation conditions can include a molecular hydrogen to hydrocarbons molar ratio in a range from r1 to r2, where r1 and r2 can be, independently, e.g., 0.5, 1, 2, 3, 4, 5, 6, 7, 8, 9, 10, 12, 14, 15, 16, 18, 20, as long as r1<r2. The alkyl-demethylation conditions can further include a weight hourly space velocity ("WHSV") in a range from w1 to w2, where w1 and w2 can be, independently, e.g., 0.1, 0.2, 0.4, 0.5, 0.6, 0.8, 1, 2, 4, 5, 6, 8, 10, 12, 14, 15, 16, 18, or 20, as long as w1<w2.

Specifically, with respect to a C9+ aromatic hydrocarbons-rich stream comprising a majority by weight, or consisting essentially of, C9+ aromatic hydrocarbons, such as a C9+ aromatic hydrocarbons-rich stream produced from a xylenes splitter described below in connection with the drawings, the alkyl-demethylation conditions can include a temperature in a range from t to t6° C., wherein t5 and t6 can be, independently, e.g.: 200, 220, 240, 250, 260, 280, 300, 320, 340, 350, 360, 380, 400, 420, 440, 450, 460, 480, or 500, as long as t5<t6 The alkyl-demethylation conditions can include an absolute pressure in the alkyl-demethylation zone in a range from p5 to p6 kilopascal, wherein p5 and p6 can be, independently, e.g.: 350, 400, 450, 500, 550, 600, 650, 700, 750, 800, 850, 900, 950, 1000, 1200, 1400, 1500, 1600, 1800, 2000, 2200, 2400, or 2500, as long as p5<p6. Thus, the alkyl-demethylation conditions can be such that the C8 aromatic hydrocarbons in the alkyl-demethylation zone are substantially in vapor phase, substantially in liquid phase, or a mixed phase. The alkyl-demethylation conditions can include a molecular hydrogen to hydrocarbons molar ratio in a range from r1 to r2, where r1 and r2 can be, independently, e.g., 0.5, 1, 2, 3, 4, 5, 6, 7, 8, 9, 10, 12, 14, 15, 16, 18, 20, as long as r1<r2. The alkyl-demethylation conditions can further include a weight hourly space velocity ("WHSV") in a range from w1 to w2, where w1 and w2 can be, independently, e.g., 0.1, 0.2, 0.4, 0.5, 0.6, 0.8, 1, 2, 4, 5, 6, 8, 10, 12, 14, 15, 16, 18, or 20, as long as w1<w2.

The Alkyl-Demethylation Catalyst of this Disclosure

The alky-demethylation catalyst useful in the alkyl-demethylation zones in the processes of this disclosure comprises a first metal element selected from Groups 7, 8, 9, and 10 metals and combinations thereof, an optional second metal element selected from Groups 11, 12, 13 and 14, and a support. Preferably, the first metal element is selected from Fe, Co, Ni, Ru, Rh, Re, Os, Ir, and combinations and mixtures thereof. Concentration of the first metal element, based on the total weight of the alkyl-demethylation catalyst can range from c(m1)1 to c(m1)2 wt %, where c(m1)1 and c(m1)2 can be, independently, e.g., 0.01, 0.02, 0.04, 0.05, 0.06, 0.08, 0.1, 0.2, 0.4, 0.5, 0.6, 0.8, 1, 2, 4, 5, 6, 8, 10, as long as c(m1)1<c(m1)2. Without intending to be bound by a particular theory, it is believed that the first metal element catalyzes the hydrogenolysis of the alkyl group attached to an aromatic ring to effect the alkyl-demethylation. Preferably, the optional second metal is selected from Cu, Ag, Au, Zn, Al, Ga, Sn, and combinations and mixtures thereof. Concentration of the second metal element, based on the total weight of the alkyl-demethylation catalyst can range from $c(m2)1$ to $c(m2)2$ wt %, where $c(m2)1$ and $c(m2)2$ can be, independently, e.g., 0.01, 0.02, 0.04, 0.05, 0.06, 0.08, 0.1, 0.2, 0.4, 0.5, 0.6, 0.8, 1, 2, 4, 5, 6, 8, 10, as long as $c(m2)1<c(m2)2$. Without intending to be bound by a particular theory, it is believed that the second metal element can minimize undesired demethylation of methylated aromatic hydrocarbons and/or aromatic ring saturation and/or hydrocracking reactions, when in combination with the first metal element to achieve a high selectivity for alkyl-demethylation.

The support in the alkyl-demethylation catalyst can be, e.g., silica, alumina, kaolin, zirconia, any molecular sieves (e.g., any zeolite), and mixtures and combinations thereof. Preferred support materials are high surface area materials ($\geq 100$ m$^2$/g). Mild-to-medium acidity is preferred in order to promote dispersion of the metal(s) on the support, while still allowing high selectivity to desired demethylation reaction. Examples of supports that can be used include silica, alumina (preferably gamma and theta phase), low-acidity zeolites, silica-alumina, alumina modified with Lanthanide series (e.g. La, Ce) and/or Group IVB metals (e.g. Zr). Additives such as alkali and/or alkali earth metals and/or chlorides may be used to tune the acidity of the support to the desired extent. In situations where a combination of transalkylation/isomerization and demethylation chemistries is desired, the acidity of the support may be raised. The amount of the support in the alkyl-demethylation catalyst can range from $c(s)1$ to $c(s)2$ wt %, where $c(s)1$ and $c(s2)2$ can be, independently, e.g., 2, 4, 5, 6, 8, 10, 15, 20, 25, 30, 35, 40, 45, 50, 55, 60, 65, 70, 75, 80, 85, 90, 95, 96, 97, 98, or 99, as long as $c(s)1<c(s)2$.

The alkyl-demethylation catalyst can further comprise an optional promoter selected from Groups 1 and 2 metal elements, and combination and mixtures thereof. The amount of the promoter can range from $c(p)1$ to $c(p)2$ wt %, based on the total weight of the alkyl-demethylation catalyst, where $c(p)1$ and $c(p)2$ can be, independently, e.g., 0.01, 0.02, 0.04, 0.05, 0.06, 0.08, 0.1, 0.2, 0.4, 0.5, 0.6, 0.8, 1, 2, 4, 5, 6, 8, 10, as long as $c(p)1<c(p)2$. Preferably, the optional promoter metal is selected from Li, Na, K, Cs, Mg, Ca, Ba. The groups 1 and 2 promoters when used in combination with the first metal element and optionally the second metal element, can enhance the performance of the alkyl-demethylation catalyst, particularly in terms of activity and selectivity for alkyl-demethylation.

Any method known in the art for making a supported metal catalyst may be used for making the alkyl-demethylation catalyst in this disclosure. In one exemplary process, a support may be impregnated with a solution (e.g., an aqueous solution) of a precursor compound of the metal element and a precursor material of the promoter, followed by drying and calcination to obtain an alkyl-demethylation catalyst comprising the support, the metal element, and the optional promoter. Alternatively, a precursor material to the support, a precursor material to the metal element, and optionally a precursor material for the promoter, may be mixed to form an admixture, which is then dried and calcined to obtain the alkyl-demethylation catalyst.

Before using the alkyl-demethylation catalyst in an alkyl-demethylation process, it may be desirable to activate the catalyst either ex-situ (i.e., outside of the alkyl-demethylation zone for its intended use) or in-situ (i.e., inside the alkyl-demethylation zone for its intended use). Activation can include, e.g., heating the catalyst in the presence of, e.g., a molecular hydrogen containing gas stream.

The C8 Aromatic Hydrocarbon Isomerization Process of this Disclosure

In a process for making p-xylene in an aromatic production plant, p-xylene is typically separated from a C8 aromatic hydrocarbon mixture comprising, in addition to p-xylene, m-xylene, o-xylene, and ethylbenzene in a p-xylene separation sub-system. Depending on the composition of the C8 aromatic hydrocarbon mixture, particularly the concentration of p-xylene therein, various technologies can be used for separating the p-xylene product, e.g., crystallization-based technologies and adsorption chromatography-based technologies. Upon separation of the p-xylene product, a residual p-xylene-depleted stream (called a raffinate in an adsorption chromatography-based process and a filtrate in a crystallization-based technology, collectively a "raffinate" herein) is produced. The raffinate is rich in m-xylene, o-xylene and ethylbenzene. To produce more p-xylene, typically the raffinate is then isomerized in the presence of an isomerization catalyst in an isomerization zone operated under isomerization conditions. A portion of the isomerization effluent, rich in p-xylene compared to the p-xylene-depleted stream fed into the isomerization zone, can be recycled to the p-xylene separation recovery sub-system, forming a xylenes loop. In the isomerization zone, direct conversion of ethylbenzene into xylenes, particularly p-xylene, is difficult. Thus, unless ethylbenzene is converted into other hydrocarbons and/or conducted away, it can accumulate in the xylenes loop. Typically, in the prior art processes, the isomerization catalyst and the isomerization conditions are chosen such that at least a portion of the ethylbenzene in the p-xylene-depleted stream fed into the isomerization zone is subjected to dealkylation (i.e., deethylation) in the presence of molecular hydrogen, whereby benzene and light hydrocarbons are produced. To facilitate deethylation, typically the isomerization conditions are chosen such that the C8 aromatic hydrocarbons present in the isomerization zone are substantially in vapor phase. In a separate version of the prior art process, the isomerization catalyst and the isomerization conditions are chosen such that at least a portion of the ethylbenzene in the p-xylene-depleted stream fed into the isomerization zone is subjected to conversion to xylenes. To facilitate ethylbenzene conversion to xylenes, typically the isomerization conditions are chosen such that the C8 aromatic hydrocarbons present in the isomerization zone are substantially in vapor phase. While this disclosure focuses on alkyl-demethylation use with the prior art process converting ethylbenzene to benzene, it should be noted that alkyl-demethylation can be applied with either version of prior the art process.

In the C8 aromatics hydrocarbon isomerization process of this disclosure, at least a portion of the p-xylene-depleted stream is subject to ethyl-demethylation of the ethyl-substituted benzene (i.e. ethylbenzene) in an ethyl-demethylation zone under ethyl-demethylation conditions to convert a portion of ethylbenzene to toluene. The ethyl-demethylation zone may be upstream the isomerization zone, or overlaps with the isomerization zone partly or in its entirety. When the ethyl-demethylation zone overlaps with the isomerization zone, then in the common zone, both the isomerization catalyst and the ethyl-demethylation zone may be present. Alternatively, a single catalyst composition may perform the dual functions of isomerization and ethyl-demethylation in the overlapping zone.

As a result of the presence of one or more ethyl-demethylation zones in the xylenes loop, the quantity of ethylbenzene entering into the isomerization can be reduced compared to a prior art process where no ethyl-demethylation zone is present in the xylenes loop. The reduced quantity of ethylbenzene reduces the need for reducing ethylbenzene via deethylation. As such, the need for a vapor-phase isomerization of the p-xylene-depleted feed can be reduced. In certain embodiments, substantially the entirety of the ethyl-demethylation effluent can be supplied to a liquid-phase isomerization zone, where isomerization of the xylenes occurs at significantly lower temperature than typical vapor-phase isomerization processes. Liquid-phase isomerization is less energy-intensive than vapor-phase isomerization and thus preferred. The Transalkylation Process of this Disclosure One aspect of this disclosure relates to a transalkylation process, the process comprising: (A) providing a C9+ aromatic hydrocarbon-rich stream comprising a C2+-hydrocarbyl-substituted aromatic hydrocarbon, wherein the C2+-hydrocarbyl substituted aromatic hydrocarbon has (i) a C2+ alkyl substitute attached to an aromatic ring therein and/or (ii) an aliphatic ring annelated to an aromatic ring therein; (B) optionally contacting at least a portion of the C9+ aromatic hydrocarbon-rich stream with an alkyl-demethylation catalyst No. 1 in an alkyl-demethylation zone No. 1 under a set of alkyl-demethylation conditions No. 1 to convert at least a portion of the C2+-hydrocarbyl substituted aromatic hydrocarbon contained in the C9+ aromatic hydrocarbon-rich stream to an alkyl-demethylated hydrocarbon to produce a alkyl-demethylated effluent No. 1 exiting the alkyl-demethylation zone No. 1; (C) optionally separating the C9+ aromatic hydrocarbons-rich stream and/or the alkyl-demethylated effluent No. 1 in a separation device No. 1 to obtain a C9-C10 aromatic hydrocarbons-rich stream and a C11+ aromatic hydrocarbons-rich stream; (D) optionally contacting at least a portion of the alkyl-demethylated effluent No. 1 and/or at least a portion of the C9-C10 aromatic hydrocarbons-rich stream with an alkyl-demethylation catalyst No. 2 in an alkyl-demethylation zone No. 2 under a set of alkyl-demethylation conditions No. 2 to convert at least a portion of the C2+-hydrocarbyl substituted aromatic hydrocarbon, if any, contained in the alkyl-demethylated effluent No. 1 and/or the C9-C10 aromatic hydrocarbons-rich stream to an alkyl-demethylated hydrocarbon to produce an alkyl-demethylated effluent No. 2 exiting the alkyl-demethylation zone No. 2; (E) feeding at least a portion of the C9+ aromatic hydrocarbons-rich stream, and/or at least a portion of the alkyl-demethylated effluent No. 1, and/or at least a portion of the C9-C10 aromatic hydrocarbons-rich stream, and/or at least a portion of the alkyl-demethylated effluent No. 2, and a benzene/toluene stream to a transalkylation zone; (F) contacting the C9+ aromatic hydrocarbons with benzene/toluene in the presence of a transalkylation catalyst in the transalkylation zone under transalkylation conditions to produce a transalkylation effluent exiting the transalkylation zone; and (G) separating the transalkylation effluent in a separation device No. 2 to obtain an optional benzene product stream, a toluene-rich stream, and a C8+ aromatic hydrocarbons-rich stream; wherein at least one of steps (B) and (D) is carried out.

In certain embodiments, the transalkylation process can further comprise: (H) separating at least a portion of the C8+ aromatic hydrocarbons-rich stream in a separation device No. 3 to obtain a xylenes-rich stream and a C9+ aromatic hydrocarbons-rich stream; and (I) providing at least a portion of the C9+ aromatic hydrocarbons-rich stream as at least a portion of the C9+ aromatic hydrocarbon-rich stream in step (A). Additionally and alternatively, the C9+ aromatic hydrocarbon-rich stream in step (A) can be derived from separating a C8+ aromatic hydrocarbons-rich stream in a xylenes splitter, which, in turn, can be produced from a reformate splitter which receives a C6+ hydrocarbon stream from a reformer. Indeed, the third separation device in step (A) can be the xylenes splitter receiving two sources of C8+ aromatic hydrocarbons.

The C9+ aromatic hydrocarbons-rich stream may be subject to alkyl-demethylation in the optional step (B) in certain embodiments. If this step is carried out, in the alkyl-demethylation zone No. 1, a portion of the C11+C2+-hydrocarbyl-substituted aromatic hydrocarbons contained therein can be converted into tetramethylbenzenes, trimethylbenzenes, xylenes, toluene, and C8+C2+-hydrocarbyl-substituted aromatic hydrocarbons via alkyl-demethylation, which can be utilized for making additional, valuable and useful products such as xylenes and benzene in, e.g., subsequent optional alkyl-demethylation step (D) and the transalkylation step (F), regardless of whether the optional separation step (C) is carried out.

Step (C) is optional. If step (C) is carried out and step (B) is not carried out, then the C11+C2+-hydrocarbyl-substituted aromatic hydrocarbons present in the C9+ aromatic hydrocarbons-rich stream will be primarily separated into the C11+ aromatic hydrocarbons-rich stream. If step (C) is carried out and step (B) is also carried out, then as discussed above, the C11+C2+-hydrocarbyl-substituted aromatic hydrocarbons present in the C9+ aromatic hydrocarbons-rich stream is at least partly converted into C10− aromatic hydrocarbons rich in methyl groups, which can be used for making additional, valuable and useful products. In embodiments where both steps (B) and (C) are carried out, it may be desired that the C9-C10 hydrocarbons-rich stream produced in step (C) also comprises at least a portion, preferably the entirety, of the C8− aromatic hydrocarbons that may be produced in the alkyl-demethylation zone No. 1 in step (B), especially if the C9+ aromatic hydrocarbons-rich stream comprises C11+C2+-hydrocarbyl-substituted aromatic hydrocarbons at a high proportion. It is possible, though, to separate in step (C) the C8− aromatic hydrocarbons produced in step (B) as one or more additional streams from the separation device No. 1, which can be further separated to produce one or more of a benzene-rich stream, a toluene-rich stream, and/or a C8 aromatic hydrocarbons-rich stream, from which additional xylenes products may be produced.

Step (D) is optional. If the optional step (D) is carried out, then the C2+-hydrocarbyl-substituted aromatic hydrocarbons C2+-hydrocarbyl-substituted aromatic hydrocarbons contained in the feed supplied into the alkyl-demethylation zone No. 2 is at least partly converted to produce alkyl-demethylated hydrocarbons which collectively comprise more methyl groups attached to the aromatic rings compared to the C2+-hydrocarbyl-substituted aromatic hydrocarbons supplied into the alkyl-demethylation zone No. 2.

In the transalkylation process of this disclosure, at least one of steps (B) and (D) is carried out.

Where step (B) is carried out and steps (C) and (D) are not carried out, then the alkyl-demethylation effluent No. 1 exiting the alkyl-demethylation zone, partly or entirely (preferably entirely), is supplied to the transalkylation zone in step (E). In such case, the feed from the alkyl-demethylation zone No. 1 to the transalkylation zone can comprise a portion of the unconverted C9+ aromatic hydrocarbons supplied into the alkyl-demethylation zone No. 1, and C8-aromatic hydrocarbons produced in the alkyl-demethylation zone No. 1.

Where step (B) is not carried out, and steps (C) and (D) are carried out, then preferably at least a portion of the hydrocarbon feed, preferably the entirety of the hydrocarbon feed, to the alkyl-demethylation zone No. 2 is at least a portion, preferably the entirety, of the C9-C10 aromatic hydrocarbons-rich stream produced in step (C). Where the entirety of the hydrocarbon feed to the alkyl-demethylation zone No. 2 is derived from the C9-C10 aromatic hydrocarbons-rich stream produced in step (C), then the C11+ aromatic hydrocarbons present in the C9+ aromatic hydrocarbons-rich stream supplied to the separation device No. 1 in step (C) are largely not utilized for making xylenes in the transalkylation step.

Where all steps (B), (C), and (D) are carried out, then a portion of the C2+-hydrocarbyl-substituted aromatic hydrocarbons supplied to the alkyl-demethylation zone No. 2 is further converted via alkyl-demethylation to produce additional methylated hydrocarbons in the alkyl-demethylation effluent No. 2. Preferably the feed to the alkyl-demethylation zone No. 2 comprises at least a portion, preferably the entirety, of the C9-C10 aromatic hydrocarbons-rich stream produced in step (C). Preferably the entirety of the feed to the alkyl-demethylation zone No. 2 comprises at least a portion, preferably the entirety, of the C9-C10 aromatic hydrocarbons-rich stream. The C2+-hydrocarbyl-substituted aromatic hydrocarbons contained in the C9-C10 hydrocarbons-rich stream supplied into the alkyl-demethylation zone No. 2 in step (D), comprising one or more of, e.g., ethylbenzene, C3-alkylbenzenes, ethylmethylbenzenes, indane, ethyldimethylbenzenes, diethylbenzenes, methylindanes, tetralin, and C4-alkylbenzenes, can be at least partly converted to toluene, xylenes, trimethylbenzenes via one or more steps of alkyl-demethylation. Carrying out both steps (B) and (D) can significantly increase the concentration of methylated aromatic hydrocarbons including toluene, xylenes, trimethylbenzenes, and tetramethylbenzenes in the alkyl-demethylated effluent No. 2 supplied to the alkyl-demethylation zone No. 2 to the transalkylation zone, which can be advantageously and conveniently converted into xylenes in the transalkylation zone.

In certain embodiments, the second alkyl-demethylation zone may be located upstream of the transalkylation zone. In such case, at least a portion, desirably the entirety, of the second alkyl-demethylated effluent is supplied to the transalkylation zone. In one embodiment, the alkyl-demethylation zone and the transalkylation zone are located in separate vessels. In another embodiment, the alkyl-demethylation zone and the transalkylation zone may be located in a common vessel such as a reactor housing, wherein the alkyl-demethylation catalyst is disposed in an upstream bed, and the transalkylation catalyst in a downstream bed.

In certain embodiments, the second alkyl-demethylation zone may overlap with the transalkylation zone at least partly. Thus, the two zones may be present in a common vessel such as a reactor housing. In the overlap of the two zones, the transalkylation catalyst and the alkyl-demethylation catalyst may be both present, e.g., as a physical mixture. In another embodiment, the transalkylation catalyst performs dual functions of catalyzing transalkylation reactions and the alkyl-demethylation reactions of the non-alkyl-demethylated substituted aromatic hydrocarbons.

In embodiments where the second alkyl-demethylation zone is present and located upstream of the transalkylation zone, the process may further comprise contacting at least a portion of the alkyl-demethylated effluent No. 2 and/or at least a portion of the C9-C10 aromatic hydrocarbons-rich stream with an alkyl-demethylation catalyst No. 3 in an alkyl-demethylation zone No. 3 under a set of alkyl-demethylation conditions No. 3 to convert at least a portion of the C2+-hydrocarbyl-substituted aromatic hydrocarbon, if any, contained in the alkyl-demethylated effluent No. 2 and/or the C9-C10 aromatic hydrocarbons-rich stream to an alkyl-demethylated hydrocarbon, wherein the alkyl-demethylation zone No. 3 at least partly overlaps with the transalkylation zone. The third alkyl-demethylation zone can be considered as equivalent the second alkyl-demethylation zone at least partly overlapping with the transalkylation zone as described above.

The alkyl-demethylation catalyst Nos. 1, 2, and 3 may be the same or different. Any alkyl-demethylation catalyst described in this disclosure earlier may be used as one or more of the alkyl-demethylation catalyst Nos. 1, 2, and 3 in the transalkylation processes of this disclosure.

The sets of alkyl-demethylation conditions Nos. 1, 2, and 3 in the alkyl-demethylation zone Nos. 1, 2, 3, may be the same or different. They may include an alkyl-demethylation temperature in a range from t5 to t6° C., wherein t5 and t6 can be, independently, e.g.: 200, 220, 240, 250, 260, 280, 300, 320, 340, 350, 360, 380, 400, 420, 440, 450, 460, 480, or 500, as long as t5<t6. The alkyl-demethylation conditions can include an absolute pressure in the alkyl-demethylation zone in a range from p5 to p6 kilopascal, wherein p5 and p6 can be, independently, e.g.: 350, 400, 450, 500, 550, 600, 650, 700, 750, 800, 850, 900, 950, 1000, 1200, 1400, 1500, 1600, 1800, 2000, 2200, 2400, 2600, 2800, 3000, 3200, 3400 or 3500, as long as p5<p6.

Depending on the quantity of toluene present in the alkyl-demethylated effluent No. 2 supplied into the transalkylation zone, an additional quantity of benzene/toluene in a benzene/toluene stream may be supplied to the transalkylation zone in step (E) as well. If additional benzene/toluene is supplied to the alkylation zone, the benzene/toluene stream can comprise benzene and toluene at any proportion. Preferably the benzene/toluene stream comprises ≥50 wt %, ≥60 wt %, ≥70 wt %, ≥80 wt %, ≥90 wt %, ≥95 wt %, ≥98 wt %, or ≥99 wt % of toluene, based on the total weight of benzene and toluene in the benzene/toluene stream. Proper ratio of toluene to C9+ aromatic hydrocarbons in the hydrocarbon feed to the transalkylation zone can be decided based on the composition of the C9+ aromatic hydrocarbons to maximize the production of xylenes. In certain embodiments, at a least portion of the benzene product stream and/or at least a portion of the toluene-rich stream produced in step (G) is supplied to the transalkylation zone as at least a portion of the benzene/toluene stream in step (E).

The transalkylation zone comprises a transalkylation catalyst disposed therein. Transalkylation catalysts known in the art may be used in the transalkylation zone in the processes of this disclosure. The transalkylation catalyst can comprise one or more zeolites such as MFI, MEL, MTW, MOR, BEA, MEI, MWW framework zeolites. The transalkylation catalyst may further comprise a first metal element selected from groups 6, 7, 8, 9, and 10 metals, preferably Mo, Ru, Rh, Ru, Pd, Re, Os, Ir, Pt, and combinations or mixtures of two or more thereof. The transalkylation catalyst may further comprise a second metal element selected from groups 11, 12, 13, and 14 metals, preferably Ag, Cu, Zn, Ga, In, Sn, and combinations or mixtures of two or more thereof. The transalkylation catalyst may further comprise a binder such as alumina, silica, zirconia, titania, and combinations and mixtures thereof. For the transalkylation catalyst used in the process of this disclosure, the concentration of the first metal element can be desirably low, e.g., in the range from c1 to c2 wt %, based on the total weight of the transalkylation catalyst, where c1 and c2 can be, 0.001, 0.004, 0.005, 0.008, 0.01, 0.04, 0.05, 0.08, 0.1, 0.4, 0.5, 1, as long as c1<c2. Furthermore for the transalkylation catalyst used in the process of this disclosure, the concentration of the second metal element can be desirably low, e.g., in the range from c1 to c2 wt %, based on the total weight of the transalkylation catalyst, where c1 and c2 can be, 0.001, 0.004, 0.005, 0.008, 0.01, 0.04, 0.05, 0.08, 0.1, 0.4, 0.5, 1, 2, 3, 4, 5, as long as c1<c2. In one particularly advantageous embodiment, the transalkylation catalyst is substantially free of the group 8, 9, or 10 metal element.

The transalkylation conditions in the transalkylation zone may enable a vapor-phase transalkylation, e.g., where all of the aromatic hydrocarbons present in the transalkylation zone are in vapor phase. The transalkylation conditions may enable a liquid-phase transalkylation, e.g., where all of the aromatic hydrocarbons present in the transalkylation zone are in liquid phase. The transalkylation conditions may enable a mixed-phase transalkylation where liquid and vapor phases of the aromatic hydrocarbons co-exist in the transalkylation zone. Molecular hydrogen may be co-fed into the transalkylation zone.

In the prior art transalkylation process, to convert the C2+-hydrocarbyl-substituted aromatic hydrocarbons in the transalkylation zone into more valuable products, typically the transalkylation catalyst and conditions are chosen such that at least a portion of the C2+ alkyl groups attached to aromatic rings are subject to dealkylation in their entirety without leaving a residual alkyl group attached to an aromatic ring. To facilitate C2+ alkyl group dealkylation, a precious metal is typically included in the transalkylation catalyst, and a high transalkylation temperature enabling vapor-phase transalkylation is typically used. Hydrogenation of the dealkylated C2+ alkyl groups, in order to avoid re-alkylation reactions, requires the presence of molecular hydrogen fed into the transalkylation zone. The vapor-phase transalkylation requires heating the hydrocarbon feed to a high temperature and subsequently cooling and condensing the transalkylation effluent for the purpose of distillation separation, and is therefore energy-intensive. Moreover, the C2+ alkyl groups and the aliphatic rings annelated to an aromatic ring in the C2+-hydrocarbyl-substituted aromatic hydrocarbons supplied into the transalkylation zone are typically converted into low-value light hydrocarbons in the presence of molecular hydrogen.

Due to the presence of one or more of the transalkylation zone Nos. 1, 2, and 3 in the transalkylation processes of this disclosure, and the performance of at least one of the alkyl-demethylation steps, the concentration of C2+ alkyl group substituted aromatic hydrocarbons supplied into the transalkylation zone can be significantly reduced compared to a prior art transalkylation process without an alkyl-demethylation step at all. As such, the need for dealkylation in the transalkylation zone of the C2+ alkyl groups and aliphatic rings can be significantly reduced. The transalkylation catalyst for the transalkylation process of this disclosure may be therefore free of the metal element, especially expensive precious metal element, reducing its costs. The reduced need for dealkylation may enable liquid-phase transalkylation in the transalkylation at a temperature significantly lower than required in a vapor-phase transalkylation process, which is much less energy-intensive and much more energy-efficient. The reduced need for dealkylation may enable transalkylation, in vapor phase, liquid phase, or mixed phase, in the absence of co-fed molecular hydrogen, further simplifying the process, system, and equipment. Furthermore, the C2+ alkyl groups and aliphatic rings can be partly converted into methyl residual groups attached to an aromatic ring, which can be used for producing additional quantity of useful products such as xylenes.

This disclosure is described in further detail below by referencing the appended drawings.

FIG. 1: A Process in the Prior Art

FIG. 1 schematically illustrates a prior art process 101 for making xylenes, particularly a p-xylene product, from a reformate stream. In this figure, a heavy naphtha stream 103 produced from a crude oil refining process, having a normal boiling point range from, e.g., 100 to 240° C., such as from 120 to 220° C., or from 140 to 200° C., or from 140 to 180° C., is supplied into a reforming zone 105. The heavy naphtha stream 103 may comprise as a majority paraffins and naphthenes, and as a minority aromatic hydrocarbons. The reforming zone 105 can include one or more of any conventional naphtha catalytic reforming reactor(s), e.g., fixed-bed reactor(s) for semi-regenerative process or moving-bed reactor(s) for continuous regeneration process, known in the art. A reforming catalyst is disposed in the reforming zone. On contacting the reforming catalyst under the reforming conditions such as those generally known in the art, hydrocarbons in the heavy naphtha stream 103 undergo a series of chemical reactions, including but not limited to isomerization, aromatization, dehydrocyclization, and the like, whereby at least a portion of the paraffins and naphthenes are converted into aromatic hydrocarbons. It is known that in typical reforming operations, the C2+-hydrocarbyl-substituted aromatic hydrocarbons, i.e., aromatic hydrocarbons comprising (i) a C2+ alkyl group connected to an aromatic ring therein and/or (ii) an aliphatic ring annelated to an aromatic ring therein, can be produced at various, sometimes significant, quantities. A reforming effluent 107 comprising C6+ aromatic hydrocarbons (including benzene, toluene, xylenes, ethylbenzene, and C9+ aromatic hydrocarbons) including C2+-hydrocarbyl-substituted aromatic hydrocarbons can be obtained from the reforming zone. In addition to aromatic hydrocarbons, the reforming effluent 107 may comprise non-aromatic hydrocarbons such as alkanes and naphthenes. Preferably the reforming effluent 107 consists essentially of C6+ hydrocarbons. The reforming effluent 107 is interchangeably called a reformate stream herein. Additional streams, such as a hydrogen stream (not shown), and an off-gas stream comprising light hydrocarbons (e.g., C5− hydrocarbons) (not shown), may be produced from the reforming zone as well.

As shown in FIG. 1, the reforming effluent 107 or a portion thereof is then supplied into a reformate splitter 109 (e.g., a single distillation column, or a series of distillation columns), from which a C6-C7 hydrocarbons-rich stream 111 and a C8+ aromatic hydrocarbons-rich stream 113 are produced. The C6-C7 hydrocarbons-rich stream 111 comprises benzene, toluene, and their co-boiling paraffins and naphthenes, and the like. The C8+ aromatic hydrocarbons-rich stream 113 can comprise C8 aromatic hydrocarbons (e.g., xylenes and ethylbenzene), C9 aromatic hydrocarbons (e.g., trimethylbenzenes, ethylmethylbenzenes, n-propylbenzene, cumene, and indane), C10 aromatic hydrocarbons (e.g., tetramethylbenzenes, diethylbenzenes, ethyldimethylbenzenes, methyl-(n-propyl)benzenes, methylcumenes, n-butylbenzene, isobutyl benzene, sec-butylbenzene, tert-butylbenzene, methylindanes, tetralin, and naphthalene), and even C11+ aromatic hydrocarbons (e.g., methylnaphthalenes, methyltetralins). The C8+ aromatic hydrocarbons-rich stream 113, optionally in combination with other C8+ aromatics-rich stream(s) such as stream 145 (described below) as a joint stream 114, is then supplied to a xylenes splitter 115 (e.g., one or more distillation columns), from which a xylenes-rich stream 117 and a C9+ aromatic hydrocarbons-rich stream 129 are produced.

The joint stream 114 is rich in C8+ aromatic hydrocarbons and lean in benzene, toluene, and co-boilers thereof compared to stream 107. Preferably, stream 114 comprises benzene and toluene in total at a concentration ≤ 5 wt %, e.g., ≤ 2 wt %, ≤ 1 wt %, ≤ 0.5 wt %, or even ≤ 0.1 wt %, based on the total weight of stream 114. The xylenes-rich stream 117 comprises xylenes and ethylbenzene. The concentration of ethylbenzene in stream 117 can range from c(EB)1 to c(EB)2 wt %, based on the total weight of the C8 aromatic hydrocarbons contained in stream 117, where c(EB)1 and c(EB)2 can be, independently, e.g., 2, 4, 5, 6, 8, 10, 12, 14, 15, 16, 18, 20, 22, 24, 25, 26, 28, 30, 32, 34, 35, 36, 38, 40, 42, 44, 45, 46, 48, or 50, as long as c(EB)1<c(EB)2. In certain cases the ethylbenzene concentration can be so substantial that c(EB)1 ≥ 10, c(EB)1 ≥ 15, c(EB)1 ≥ 20, c(EB)1 ≥ 25, or c(EB)1 ≥ 30. Stream 117 can comprise p-xylene at various concentrations, depending on the composition(s) of the C8+ aromatic hydrocarbons-rich stream(s) supplied to the xylenes splitter 115. For example, stream 117 can comprise p-xylene at a concentration from c(pX)1 to c(pX)2 wt %, based on the total weight of the C8 aromatic hydrocarbons contained in stream 117, where c(pX)1 and c(pX)2 can be, independently, e.g., 15, 16, 18, 20, 22, 24, 25, 26, 28, 30, 32, 34, 35, 36, 38, 40, 42, 44, 45, 48, 50, 52, 54, 55, 56, 58, 60, as long as c(pX)1<c(pX)2.

As shown in FIG. 1, for the purpose of production of a p-xylene product, the xylenes-rich stream 117 is typically supplied to a first p-xylene recovery sub-system 119, from which a p-xylene product stream 121 rich in p-xylene and a p-xylene depleted stream 123 are produced. The first p-xylene recovery sub-system 119 can be any crystallization-based or adsorption chromatography-based p-xylene separation systems known in the art. The first p-xylene depleted stream 123, rich in m-xylene, o-xylene, and ethylbenzene compared to stream 117, is typically at least partly supplied to an isomerization zone 125 containing an isomerization catalyst disposed therein and operated under isomerization conditions. On contacting the isomerization catalyst under isomerization conditions, a portion of the m-xylene and o-xylene in stream 125 supplied into the isomerization zone 125 are converted into p-xylene. The isomerization effluent 127 exiting the isomerization zone 125 comprises p-xylene at a concentration higher than the p-xylene depleted stream 123. The isomerization effluent 127, or a portion thereof, is then supplied to the xylenes splitter 115. The xylenes splitter 115, the p-xylene recovery sub-system 119, and the isomerization zone 125 form a xylenes-loop.

In the process of FIG. 1, streams 113, 145, 114, 117, and 123 can comprise ethylbenzene at substantial concentrations (e.g., ≥ 5 wt %, ≥ 10 wt %, ≥ 15 wt %, ≥ 20 wt %, ≥ 25 wt %, ≥ 30 wt %, based on the total weight of the C8 aromatics contained therein). If the isomerization zone 125 does not have the sufficient capability to convert the ethylbenzene, then ethylbenzene can accumulate in the xylenes loop overtime, which is undesirable. To prevent ethylbenzene accumulation in the xylenes loop, the isomerization catalyst and the isomerization conditions in zone 125 are typically chosen such that at least a portion of the ethylbenzene is converted to benzene via deethylation. To effect deethylation, the isomerization conditions typically include temperature and pressure sufficient to maintain the C8 aromatics substantially in vapor phase in the isomerization zone ("vapor-phase conditions", "vapor-phase isomerization"). Conducting xylenes isomerization substantially in vapor phase requires heating the hydrocarbons in the isomerization zone to a high temperature and subsequently cooling and condensing the isomerization effluent to liquid state for the purpose of distillation separation, and therefore is energy intensive. Moreover, vapor-phase isomerization typically produces light hydrocarbons resulting from dealkylation and non-aromatic hydrocarbons due to aromatic ring saturation and/or ring scission, which is typically removed in an intermediate deheptanizer (not shown) before the isomerization effluent 127 is supplied to the xylenes splitter 115, adding to the complexity of the xylenes loop in the process.

C8 aromatic hydrocarbon isomerization processes, catalysts, and conditions are disclosed in, e.g., U.S. Pat. Nos. 7,247,762 and 7,271,118, the contents of all of which are incorporated herein by reference in their entirety.

As shown in FIG. 1, the C9+ aromatic hydrocarbons-rich stream 129 produced from the xylenes splitter 115, typically containing C9, C10, and C11+ aromatic hydrocarbons, is then typically separated in a distillation column 131 to obtain a C9-C10 aromatic hydrocarbons-rich stream 133 and a C11+ aromatic hydrocarbons-rich stream 135. Stream 135 is typically conducted away and used as, e.g., a motor gasoline blending stock, a fuel oil, and the like. Stream 133 comprises methylated aromatic hydrocarbons and the C2+-hydrocarbyl-substituted aromatic hydrocarbons. The total concentration of the C2+-hydrocarbyl-substituted aromatic hydrocarbons in stream 133 can be significant, e.g., ranging from c(A1)1 to c(A1)2 wt %, based on the total weight of the aromatic hydrocarbons in stream 133, where c(A1)1 and c(A1)2 can be, independently, e.g., 2, 4, 5, 6, 8, 10, 12, 14, 15, 16, 18, 20, 22, 24, 25, 26, 28, 30, 32, 34, 35, 36, 38, or 40, as long as c(A1)1<c(A1)2. Stream 133, along with a benzene/toluene-rich stream 146, is then supplied into a transalkylation zone 147 having a transalkylation catalyst disposed therein. In the presence of the transalkylation catalyst and under transalkylation conditions, the C9-C10 aromatic hydrocarbons react with benzene/toluene to produce xylenes. The direct transalkylation between such C9-C10 C2+-hydrocarbyl-substituted aromatic hydrocarbons and benzene/toluene would yield ethylbenzene and other C9+C2+-hydrocarbyl-substituted aromatic hydrocarbons. To increase the production of xylenes and/or benzene/toluene in the transalkylation zone 147, the transalkylation catalyst and the transalkylation conditions are typically chosen such that at least a portion of the C9+C2+-hydrocarbyl-substituted aromatic hydrocarbons and ethylbenzene in the transalkylation zone are converted via dealkylation from the aromatic rings of the C2+ alkyl groups in their entirety (without removing a methyl group attached directly to an aromatic ring). The dealkylation results in the conversion of the C2+ alkyl groups into light hydrocarbon (typically in the presence of molecular hydrogen and a hydrogenation function in the dealkylation catalyst used in the transalkylation zone). The removal of the C2+ alkyl group is therefore a loss for the purpose of producing xylenes. It would be desirable to convert the C2+ alkyl group into a methyl group attached to a benzene ring—which can be then used for producing xylenes via, e.g., isomerization, transalkylation, and/or disproportionation. Similar to deethylation of ethylbenzene, effective dealkylation from the C9-C10 C2+-hydrocarbyl-substituted aromatic hydrocarbons and ethylbenzene in the transalkylation zone typically calls for vapor phase conditions which require high temperature. Such vapor-phase transalkylation is energy-intensive because streams 146 and 133 must be heated to a high temperature before entering the transalkylation zone to effect the vapor-phase isomerization, and the vapor effluent 149 from the transalkylation zone needs to be subsequently cooled and condensed into liquid phase for the purpose of distillation separation. Moreover, vapor-phase transalkylation typically produces light hydrocarbons resulting from dealkylation and non-aromatic hydrocarbons due to aromatic ring saturation and/or ring scission, which is typically removed in an intermediate deheptanizer (not shown) before the isomerization effluent 127 is supplied to the benzene tower 141, adding to the complexity of the transalkylation process.

Aromatic hydrocarbon transalkylation processes, catalysts, and conditions are disclosed in, e.g., U.S. Pat. Nos. 5,763,720 and 8,183,424, the contents of all of which are incorporated herein in their entirety.

As shown in FIG. 1, the C6-C7 hydrocarbons-rich stream 111 is typically supplied to an extraction distillation zone 137, where a C6-C7 aromatic hydrocarbons-rich stream 139 and an aromatic hydrocarbons-depleted raffinate stream 138 are produced. Stream 139 is then supplied to the benzene tower 141, from which a benzene product stream 143, a toluene-rich stream 146, and a C8+ aromatic hydrocarbons-rich stream 145 are produced. The toluene-rich stream 146, or a portion thereof, is supplied to the transalkylation 147 together with the C9-C10 aromatic hydrocarbons-rich stream 133 as described above. The C8+ aromatic hydrocarbons-rich stream 145 is then supplied to the xylenes splitter 115 along with stream 113, as described above.

The traditional process for making xylenes, particularly p-xylene, from a heavy naphtha stream as illustrated in FIG. 1 thus typically requires: (i) conducting the isomerization of the p-xylene-depleted stream 123, or at least a portion thereof, in vapor phase in order to accommodate deethylation of ethylbenzene contained in stream 123; (ii) conducting the transalkylation between the C9-C10 aromatic hydrocarbons-rich stream 133 and benzene/toluene stream in the transalkylation zone 147 in vapor phase in order to accommodate dealkylation of the C2+ alkyl groups in the C2+-hydrocarbyl-substituted aromatic hydrocarbons contained in stream 133. Such vapor phase processes are highly energy intensive, add to the complexity and costs of the aromatic production plant, and result in the loss of valuable methyl substitute sources which could otherwise be used for producing more xylene molecules.

Figure 2:
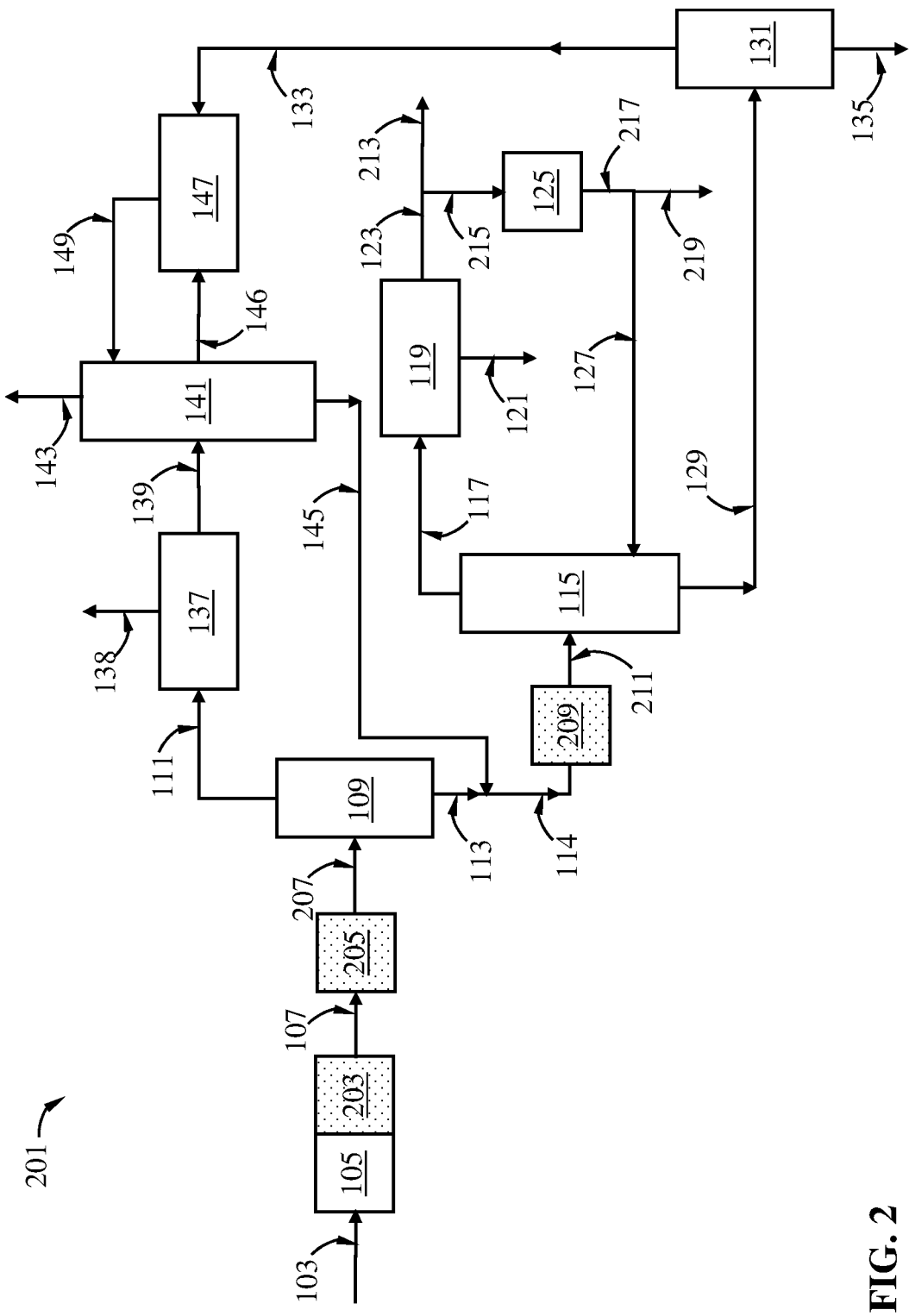
FIG. 2 is a schematic diagram showing a process of this disclosure for producing p-xylene from naphtha reforming including a xylenes loop and a transalkylation step, and one or more alkyl-demethylation steps.

FIG. 2: An Exemplary Inventive Process for Making Xylenes from Naphtha Reforming FIG. 2 schematically illustrates an exemplary inventive process 201 for making xylenes, particularly a p-xylene product from a C6+ aromatic hydrocarbons-containing stream comprising a C2+-hydrocarbyl-substituted aromatic hydrocarbon, such as a reformate stream or a hydrotreated steam-cracked naphtha stream. While this exemplary process is illustrated and described as for the primary purpose of making a p-xylene product, one having ordinary skill in the art readily understands that it can be modified for the purpose of making o-xylene, toluene, and other aromatic hydrocarbon products. In FIG. 2, a heavy naphtha stream produced from, e.g., a crude oil refining process 103, having a normal boiling point range from, e.g., 100 to 240° C., such as from 120 to 220° C., or from 140 to 200° C., or from 140 to 180° C., is supplied into a reforming zone 105. The heavy naphtha stream 103 may comprise as a majority paraffins and naphthenes. The reforming zone 105 can include one or more of any conventional naphtha catalytic reforming reactor, e.g., fixed-bed reactor for semi-regenerative process or moving-bed reactor(s) for continuous regeneration process, known in the art. A reforming catalyst is disposed in the reforming zone. On contacting the reforming catalyst and under the reforming conditions such as those generally known in the art, hydrocarbons in the heavy naphtha stream 103 undergo a series of chemical reactions, including but not limited to isomerization, aromatization, dehydrocyclization, and the like, to convert at least a portion of the paraffins and naphthenes into aromatic hydrocarbons. As discussed above, in typical reforming operations, the C2+-hydrocarbyl-substituted aromatic hydrocarbons can be produced at various quantities, sometimes significant quantities. In FIG. 2, inside a portion of the reforming zone 105, or adjacent to reforming zone and downstream of the reforming zone 105, an optional alkyl-demethylation zone (the seventh alkyl-demethylation zone pursuant to the first aspect of this disclosure) 203 is installed. In this optional alkyl-demethylation zone 203, an alkyl-demethylation catalyst (the seventh alkyl-demethylation catalyst pursuant to the first aspect of this disclosure) is disposed. In one example, the reforming zone 105 and the alkyl-demethylation zone 203 overlap partly or entirely. Such configuration can be effected by mixing a portion or the entirety of the alkyl-demethylation catalyst in the alkyl-demethylation zone 203 with a portion or the entirety of the reforming catalyst in the reforming zone 105 to form an aggregate catalyst mixture. In such case, at least a portion of the C2+-hydrocarbyl-substituted aromatic hydrocarbons generated in the reforming zone 105 can be converted to desirable alkyl-demethylated aromatic hydrocarbons on contacting the alkyl-demethylation catalyst before exiting the reforming zone 105. In another example, the reforming catalyst in zone 105 can form an upstream bed of catalyst, and the alkyl-demethylation catalyst can form a downstream bed of catalyst, and the two beds of catalysts can be located in the same or different vessels. In such case the C2+-hydrocarbyl-substituted aromatic hydrocarbons formed in the zone 107 flow to the alkyl-demethylation zone 203, where they are partly converted into alkyl-demethylated aromatic hydrocarbons, particularly desirably methylated aromatic hydrocarbons such as toluene, xylenes, and trimethylbenzenes. Due the physical proximity or overlapping nature of the reforming zone 105 and the alkyl-demethylation zone 203 (if present), the reforming conditions and the alkyl-demethylation conditions (the seventh set of alkyl-demethylation conditions pursuant to the first aspect of this disclosure) may include similar or even substantially the same temperatures, pressures, and the like. The alkyl-demethylation effluent 107 (the seventh alkyl-demethylation effluent pursuant to the first aspect of this disclosure) exiting the alkyl-demethylation zone 203 (if present) comprise C6+ aromatic hydrocarbons (including benzene, toluene, xylenes, ethylbenzene, and C9+ aromatic hydrocarbons). Since a portion of the C2+-hydrocarbyl-substituted aromatic hydrocarbons produced in the reforming zone 105 is converted into alkyl-demethylated aromatic hydrocarbons in zone 203, the concentration of such C2+-hydrocarbyl-substituted aromatic hydrocarbons in effluent 107 exiting zone 203 is reduced compared to a process where the alkyl-demethylation zone 203 is absent. An advantage of installing the alkyl-demethylation zone 203 in close proximity to the reforming zone 105 is the alkyl-demethylation of all C2+-hydrocarbyl-substituted aromatic hydrocarbons, including C8, C9, C10, and C11+C2+-hydrocarbyl-substituted aromatic hydrocarbons present or generated in zone 105 can be subject to alkyl-demethylation in zone 203, resulting in a effluent 107 with reduced concentration of the C2+-hydrocarbyl-substituted aromatic hydrocarbons, and therefore reducing the burden of the C2+-hydrocarbyl-substituted aromatic hydrocarbons in downstream processes. In addition to aromatic hydrocarbons, effluent 107 may comprise non-aromatic hydrocarbons such as alkanes and naphthenes, especially those co-boiling with the aromatic hydrocarbons. Preferably effluent 107 consist essentially of C6+ hydrocarbons. Additional streams, such as a hydrogen stream (not shown), and an off-gas stream comprising light hydrocarbons (e.g., C5-hydrocarbons) (not shown), may be produced from the reforming zone 105 and/or the alkyl-demethylation zone 203 as well.

As shown in FIG. 2, the reforming effluent (where the optional alkyl-demethylation zone 203 is absent) or the alkyl-demethylation effluent (where the optional alkyl-demethylation zone 203 is present) 107, or a portion thereof, is then supplied into another, downstream, optional alkyl-demethylation zone 205 (the first alkyl-demethylation zone pursuant to the first aspect of this disclosure) downstream of zones 105 and 203. In one embodiment, the entirety of effluent 107 from the zone(s) 105/203 is supplied to the alkyl-demethylation zone 205. In another embodiment, effluent 107 from the zone(s) 105/203 is first separated (not shown), e.g., to remove a portion or certain components before a portion thereof is supplied into the alkyl-demethylation zone 205. Where the optional alkyl-demethylation zone 203 is absent, the alkyl-demethylation zone 205 receives a reforming effluent 107. Where the optional alkyl-demethylation zone is present, the alkyl-demethylation zone 205 may be desirably absent if the conversion of the C2+-hydrocarbyl-substituted aromatic hydrocarbons in zone 203 is sufficiently high. Alternatively, the alkyl-demethylation zone 205 can be installed downstream of the alkyl-demehtylation zone 203 to provide an additional alkyl-demethylation processing of the C2+-hydrocarbyl-substituted aromatic hydrocarbons present in the alkyl-demethylation effluent 107. Similar to the optional zone 203, zone 205, if present, comprises an alkyl-demethylation catalyst (the first alkyl-demethylation catalyst pursuant to the first aspect of this disclosure) disposed therein. The demethylation catalyst in zone 205 may be the same or different from the demethylation catalyst in zone 203, if both are present. The operation conditions in zone 205 (the first set of alkyl-demethylation conditions pursuant to the first aspect of this disclosure) may be the similar to or different from those in zone 203 (the seventh set of alkyl-demethylation conditions pursuant to the first aspect of this disclosure). If substantially all of the C2+-hydrocarbyl-substituted aromatic hydrocarbons are supplied into zone 205, then similar to in zone 203, substantially all C2+-hydrocarbyl-substituted aromatic hydrocarbons, including C8, C9, C10, and C11+C2+-hydrocarbyl-substituted aromatic hydrocarbons can be subjected to alkyl-demethylation conditions in zone 205 and a portion thereof is converted into alkyl-demethylated aromatic hydrocarbons. This can be advantageous because, with a potentially high conversion of the C2+-hydrocarbyl-substituted aromatic hydrocarbons of various molecular weights at such upstream locations, the burden to process high concentrations of C2+-hydrocarbyl-substituted aromatic hydrocarbons in downstream processes, such as C8 aromatic hydrocarbons isomerization and/or C9-C10 aromatic hydrocarbons transalkylation with C6-C7 aromatic hydrocarbons, can be significantly reduced, which enables highly advantageous downstream processes such as liquid-phase-only isomerization and liquid-phase-only transalkylation as described in greater detail below. An alkyl-demethylation effluent 207 exits the alkyl-demehtylation zone 205. Effluent 207 can comprise benzene, toluene, non-aromatic co-boilers of benzene and/or toluene, xylenes, trimethylbenzenes, and C2+-hydrocarbyl-substituted aromatic hydrocarbons such as ethylbenzene, methylethylbenzenes, and the like. Compared to effluent 107, effluent 207 desirably comprises the C2+-hydrocarbyl-substituted aromatic hydrocarbons at a reduced quantity.

In certain embodiments, the optional alkyl-demethylation zone 203 is present, and the alkyl-demethylation zone 205 is absent. Such embodiments can be advantageous if the presence of zone 203 alone is sufficient to reduce the concentration of the C2+-hydrocarbyl-substituted aromatic hydrocarbons in stream 107 to a sufficiently low level. In certain other embodiments, zone 203 is absent and zone 205 is present. Such embodiments can be advantageous if the reforming catalyst in reforming zone 105 and the alkyl-demethylation catalyst in zone 205 have substantially different catalyst cycle times, and/or the reforming conditions in zone 105 and the alkyl-demethylation conditions in zone 205 are substantially different, necessitating two separate reactors. In other embodiments, both alkyl-demethylation zones 203 and 205 are present. Such embodiments can be advantageous in that in both zones 203 and 205, a portion of the C2+-hydrocarbyl-substituted aromatic hydrocarbons are converted to alkyl-demethylated aromatic hydrocarbons, resulting in a high combined conversion thereof. Such embodiments can be advantageous also if the reforming catalyst can perform dual functions of reforming and alkyl-demethylation, and an alkyl-demethylation catalyst specialized for alkyl-demethylation but not reforming is disposed in zone 205 to further convert at least a portion the C2+-hydrocarbyl-substituted aromatic hydrocarbons present in stream 107 to alkyl-demethylated aromatic hydrocarbons.

As shown in FIG. 2, effluent 107 (where the optional alkyl-demethylation zone 205 is absent) or effluent 207 (where the optional alkyl-demethylation zone 205 is present) is then supplied into a reformate splitter 109 (e.g., a single distillation column, or a series of distillation columns), from which a C6-C7 hydrocarbons-rich stream 111 and a C8+ aromatic hydrocarbons-rich stream 113 are produced. The C6-C7 hydrocarbons-rich stream 111 comprises benzene, toluene, and their co-boiling paraffins and naphthenes. It is highly desirable that stream 111 is substantially free of C8+ aromatic hydrocarbons. It is highly desirable that stream 111 is substantially free of the C2+-hydrocarbyl-substituted aromatic hydrocarbons. The C8+ aromatic hydrocarbons-rich stream 113 can comprise C8 aromatic hydrocarbons (e.g., xylenes and ethylbenzene), C9 aromatic hydrocarbons (e.g., trimethylbenzenes, ethylmethylbenzenes, n-propylbenzene, cumene, and indane), C10 aromatic hydrocarbons (e.g., tetramethylbenzenes, diethylbenzenes, ethyldimethylbenzenes, methyl-(n-propyl)benzenes, methylcumenes, n-butylbenzene, isobutyl benzene, sec-butylbenzene, tert-butylbenzene, methylindanes, tetralin, and naphthalene), and even C11+ aromatic hydrocarbons (e.g., methylnaphthalenes, methyltetralins). The C8+ aromatic hydrocarbons-rich stream 113, optionally in combination with other C8+ aromatics-rich stream(s) such as stream 145 (described below) as a joint stream 114, is then supplied to an optional alkyl-demethylation zone 209 (the second alkyl-demethylation zone pursuant to the first aspect of this disclosure). Similar to the optional alkyl-demethylation zones 203 and 205, if present, zone 209 comprises an alkyl-demethylation catalyst (the second alkyl-demethylation catalyst pursuant to the first aspect of this disclosure) disposed therein. The alkyl-demethylation catalyst in zone 209 may be the same or different from the alkyl-demethylation catalyst(s) in zone(s) 203 and/or 205. Zone 209 is operated under a set of alkyl-demethylation conditions (the second set of alkyl-demethylation conditions pursuant to the first aspect of this disclosure) to effect the conversion of at least a portion of the C2+-hydrocarbyl-substituted aromatic hydrocarbons into alkyl-demethylated aromatic hydrocarbons, particularly methylated aromatic hydrocarbons on contacting the alkyl-demethylation catalyst therein. The inclusion of zone 209 in the process can be particularly advantageous if stream 113 and/or stream 145, and hence stream 114, comprise substantial quantity of the C2+-hydrocarbyl-substituted aromatic hydrocarbons.

The joint stream 114 is rich in C8+ aromatic hydrocarbons and lean in benzene, toluene, and co-boilers thereof. Preferably, stream 114 comprises benzene and toluene in total at a concentration $\leq 5$ wt %, e.g., $\leq 2$ wt %, $\leq 1$ wt %, $\leq 0.5$ wt %, or even $\leq 0.1$ wt %, based on the total weight of stream 114. Since the C2+-hydrocarbyl-substituted aromatic hydrocarbons are all C8+ aromatic hydrocarbons, stream 113 is rich in the C2+-hydrocarbyl-substituted aromatic hydrocarbons compared to stream 207. To the extent stream 145 comprises the C2+-hydrocarbyl-substituted aromatic hydrocarbons at any significant amount, it may be desirable to combine it with stream 113, as shown in FIG. 2, and then supplied to the alkyl-demethylation zone 209. If, however, stream 145 is substantially free of the C2+-hydrocarbyl-substituted aromatic hydrocarbons, it may be desirable to supply it directly to xylenes splitter 115 (as described below), bypassing the alkyl-demethylation zone 209 (if present). Including the alkyl-demethylation zone 209 in the process has the advantage of reducing the burden of the C2+-hydrocarbyl-substituted aromatic hydrocarbons in subsequent processes such as isomerization and transalkylation. In alkyl-demethylation zones 203 and 205, the alkyl-demethylation process are typically performed in the presence of substantial quantities of benzene, toluene, and co-boilers thereof. On the other hand, alkyl-demethylation in zone 209 can be performed in the presence of much lower quantities of benzene and toluene in the reaction mixture because the feed stream 114 thereto can comprise toluene at a much lower concentration than stream(s) 107 and 207. Since a desirable product of an alkyl-demethylation process is toluene, the lower toluene concentration in stream 114 can be conducive to a higher conversion of the C2+-hydrocarbyl-substituted aromatic hydrocarbons in zone 209 than in zones 203 and 205. The stream 211 exiting zone 209 (the second alkyl-demethylation effluent pursuant to the first aspect of this disclosure) can comprise toluene generated from the alkyl-demethylation reactions, in addition to C8+ aromatic hydrocarbons.

It is highly desirable that at least one of zones 203, 205, and 209 is present in the process flow for an aromatic hydrocarbons production process including a heavy naphtha reforming step because, as discussed above, heavy naphtha reforming tends to produce substantial quantity of the C2+-hydrocarbyl-substituted aromatic hydrocarbons. By converting the C2+ alkyl groups or carbon atoms in rings annealed to a benzene ring into one or more methyl groups attached to a benzene ring in an alkyl-demethylation step, one can increase the production of methylated benzenes and/or benzene, as discussed above. In certain embodiments of the process of the first aspect of this disclosure, only one of the optional alkyl-demethylation zones 203, 205, and 209 is present. Such single alkyl-demethylation zone arrangement can be advantageous if a single zone is capable of converting the C2+-hydrocarbyl-substituted aromatic hydrocarbons to a sufficient level. In other embodiments, especially those where stream 145 does not comprise substantial quantity of the C2+-hydrocarbyl-substituted aromatic hydrocarbons, both zones 203 and 205 can be present to effect sufficient conversion of the C2+-hydrocarbyl-substituted aromatic hydrocarbons but zone 209 is absent. In other embodiments, especially those where stream 145 comprises substantial quantity of the C2+-hydrocarbyl-substituted aromatic hydrocarbons, zone 209 and either of zones 203 and 205, but not necessarily both, can be present. In other embodiments, especially those where substantial quantities of the C2+-hydrocarbyl-substituted aromatic hydrocarbons are produced in the reforming zone or present in stream 103, to maximize the conversion of the C2+-hydrocarbyl-substituted aromatic hydrocarbons, one may desire to include all three zones 203, 205, and 209 in the process flow.

As shown in FIG. 2, effluent 211 exiting the alkyl-demethylation zone 209 (if present) and/or stream 114 (if zone 209 is not present and/or if stream 114 partly bypasses zone 209), or a portion thereof, is fed into a xylenes splitter 115 (e.g., a distillation column), from which a xylenes-rich stream 117 and a C9+ aromatic hydrocarbons-rich stream 129 are produced. In embodiments where zone 209 is present, a portion of the C2+-hydrocarbyl-substituted aromatic hydrocarbons in stream 114 that are single-substituted by a C2+ alkyl group (e.g., ethylbenzene, n-propylbenzene, cumene, and the like) are converted into toluene via one or more steps of alkyl-demethylation. In such embodiments, a C7− aromatic hydrocarbon stream (now shown) may be produced from the xylenes splitter 115 as well. The C7− aromatic hydrocarbon stream produced from 115 may be supplied, e.g., to the extraction zone 137. The xylenes-rich stream 117 comprises the xylenes and ethylbenzene at various concentrations depending on, inter alia, whether one or more of zones 203, 205, and 209 are present. The presence of one of more of zones 203, 205, and 209, as discussed above, reduces the quantity of ethylbenzene in stream 117 compared to the corresponding stream in the process of FIG. 1 where none of zones 203, 205, and 209 is present. The concentration of ethylbenzene in stream 117 in FIG. 2 can range from c(EB)3 to c(EB)4 wt %, based on the total weight of the C8 aromatic hydrocarbons contained in stream 117, where c(EB)3 and c(EB)4 can be, independently, e.g., 0.1, 0.2, 0.4, 0.5, 0.6, 0.8, 1, 2, 4, 5, 6, 8, 10, 12, 14, 15, 16, 18, 20, 22, 24, 25, 26, 28, 30, 32, 34, 35, 36, 38, 40, as long as c(EB)3<c(EB)4. In certain cases the ethylbenzene concentration can be low such that that c(EB)4 $\leq$ 20, c(EB)4 $\leq$ 10, c(EB)4 $\leq$ 5, or even c(EB)4 $\leq$ 1. Stream 117 in FIG. 2 can comprise p-xylene at various concentrations, $\leq$ depending on the composition(s) of the C8+ aromatic hydrocarbons-rich stream(s) supplied to the xylenes splitter 115. For example, stream 117 can comprise p-xylene at a concentration from c(pX)1 to c(pX)2 wt %, based on the total weight of the C8 aromatic hydrocarbons contained in stream 117, where c(pX)1 and c(pX)2 can be, independently, e.g., 15, 16, 18, 20, 22, 24, 25, 26, 28, 30, 32, 34, 35, 36, 38, 40, 42, 44, 45, 48, 50, 52, 54, 55, 56, 58, 60, as long as c(pX)1<c(pX)2.

As shown in FIG. 2, similar to the convention process of FIG. 1, the xylenes-rich stream 117 produced from the xylenes splitter 115 is then supplied to a first p-xylene recovery sub-system 119, from which a first p-xylene product stream 121 rich in p-xylene and a first p-xylene depleted stream 123 are produced. The first p-xylene depleted stream 123, rich in m-xylene, o-xylene, and ethylbenzene compared to stream 117, partly (shown as stream 215) or entirety, is then supplied to a first isomerization zone 125, where m-xylene and/or o-xylene are isomerized to form additional p-xylene in the presence of a first isomerization catalyst under a first set of isomerization conditions. The isomerization effluent 217, or a portion thereof (shown as stream 127), is then supplied to the xylenes splitter 115. The xylenes splitter 115, the p-xylene recovery sub-system 119, and the isomerization zone 125 form a xylene-loop.

In the conventional process of FIG. 1, if the isomerization zone 125 does not have the sufficient capability to convert the ethylbenzene contained in stream 123, then ethylbenzene can undesirably accumulate in the xylene loop overtime to a high concentration. To prevent ethylbenzene accumulation in the xylene loop, especially where streams 113, 145, 117, and 123 comprise ethylbenzene at substantial concentrations (e.g., $\geq 10$ wt %, based on the total weight of the C8 aromatics contained therein), typically the isomerization catalyst and the isomerization conditions in the isomerization zone in the conventional process of FIG. 1 are chosen such that at least a portion of the ethylbenzene is converted to benzene via deethylation under vapor-phase isomerization conditions. As a result of deethylation, the ethyl group in an ethylbenzene molecule is converted into ethane (in the presence of molecular hydrogen and a hydrogenation function in the deethylation catalyst used in the isomerization zone). The result of deethylation of ethylbenzene is the loss of an ethyl substitute connected to a benzene ring. Conducting xylenes isomerization substantially in vapor phase requires heating the hydrocarbons in the isomerization zone to a high temperature and subsequent cooling and condensing the isomerization effluent to liquid state for separation in the xylenes splitter 115, and therefore is energy intensive.

As shown in FIG. 2, to the extent streams 123 and 215 may comprise ethylbenzene at substantial quantity, one may operate the first isomerization zone 125 in FIG. 2 under vapor-phase conditions to covert at least a portion of the ethylbenzene via deethylation, so that ethylbenzene quantity in the xylenes loop does not become overly high, similar to the conventional process of FIG. 1 including an isomerization zone operated under vapor-phase conditions.

In the process of FIG. 2, however, owing to the presence of at least one of zones 203, 205, and 209, and the ensuing reduced quantity of ethylbenzene in stream 117 compared to the corresponding stream in FIG. 1, the need for deethylation of ethylbenzene in the isomerization zone 125 is reduced, and hence the need for vapor-phase isomerization conditions in zone 205 is reduced. Accordingly, at least a portion, desirably a majority, and even the entirety, of the p-xylene-depleted stream 123 can be processed in zone 125 under isomerization conditions such that the C8 aromatic hydrocarbons therein are substantially in liquid phase. Because such liquid-phase isomerization is conducted under an operation temperature significantly lower than that in a conventional vapor-phase isomerization required in the process of FIG. 1, and hence is much less energy intensive, and more energy efficient. As shown in FIG. 2, the p-xylene-depleted stream 123 is split into streams 213 and 215. Stream 215 is supplied to the isomerization zone 125, which operates preferably under liquid-phase isomerization conditions. Stream 213, or a portion thereof, can be a purge stream conducted away and then used, e.g., as molar gas blending stock. Conducting stream 213 or a portion thereof away from the xylenes loop can reduce the quantity of ethylbenzene quantity circulating in the loop. Additionally or alternatively, stream 213, or a portion thereof, can be recycled (not shown) to any of zones 203, 205, and 209 (if present), preferably either of zones 205 and 209 (if present) and more preferably zone 209 (if present), particularly where the quantity of ethylbenzene in stream 123 has reached a very high level. Additionally or alternatively, stream 213, or a portion thereof, can be supplied to a second isomerization zone (not shown), which can be operated under vapor-phase conditions, to isomerize the xylenes and convert the ethylbenzene via deethylation in a conventional manner. The effluent from the second isomerization zone, or a portion thereof, after optional separation of light hydrocarbons and/or non-aromatic hydrocarbons, can be supplied to the xylenes splitter 115 as well.

The first isomerization effluent 217 exiting the first isomerization zone 125 is rich in p-xylene compared to stream 215. To recover the p-xylene from stream 217, a part (as shown as stream 127) or the entirety (not shown) of stream 217 is then supplied to the xylenes splitter. If zone 125 is operated under vapor-phase isomerization conditions, stream 217 may comprise, in addition to aromatic hydrocarbons such as xylenes and ethylbenzene, light hydrocarbons resulting from deethylation and non-aromatic hydrocarbons. Before being fed into the xylenes splitter 115, streams 217 and/or 127 may be separated to remove such light hydrocarbons and non-aromatic hydrocarbons (not shown). If zone 125 is operated under liquid-phase isomerization conditions without deethylation of ethylbenzene, stream 217 tends to comprise such light hydrocarbons and non-aromatic hydrocarbons at quantities significantly lower than a corresponding effluent stream exiting an isomerization zone under vapor-phase conditions, if any at all. Thus, stream 217 exiting a liquid-phase isomerization zone 125, or a portion thereof (shown as stream 127), can be directly supplied to the xylenes splitter 115 without an intermediate separation step (with optional heating/cooling, and the like). Isomerizing substantially the entirety of the p-xylene-depleted stream 123 only in a liquid-phase isomerization zone without using a vapor-phase isomerization zone clearly results in a simpler, less energy-intensive, and more energy-efficient xylenes loop compared to the conventional process of FIG. 1 necessitating a vapor-phase isomerization zone.

As shown in FIG. 2, the first isomerization effluent 217 is split into streams 127 and 219. Stream 217, or a portion thereof, after optional further intermediate separation as appropriate, is supplied to the xylenes splitter 115. Stream 219 or a portion thereof can be conducted away as a purge stream and used for, e.g., motor gas blending. Additionally or alternatively, stream 219 or a portion thereof can be recycled (not shown) to one or more of zones 203, 205, and 209 (if present), preferably to one or more of zones 205 and 209 (if present), and preferably to zone 209 (if present), where the ethylbenzene contained therein can be converted to more valuable molecules via alkyl-demethylation. Additionally or alternatively, stream 219 or a portion thereof can be recycled (not shown) directly to the p-xylene recovery sub-system 119, bypassing the xylenes splitter 115, to recover a portion of p-xylene therein. Bypassing the xylenes splitter can further improve the energy efficiency of the xylenes loop. The isomerization effluent from a vapor-phase isomerization zone typically contains light hydrocarbons and other non-aromatic hydrocarbons generated from, e.g., dealkylation, and therefore is not directly recycled to the p-xylene recovery sub-system without an intermediate separation step, e.g., in a deheptanizer and/or the xylenes splitter 115. Conversely, the isomerization effluent produced from a liquid phase isomerization zone contains such light hydrocarbons and other non-aromatic hydrocarbons at much lower concentrations than in a typical vapor-phase isomerization effluent, if any at all, and therefore can be directly recycled to the p-xylene recovery sub-system to recover additional p-xylene formed in the isomerization zone, bypassing the xylenes splitter. The liquid-phase isomerization zone 125, optionally in combination with recycling streams 213 and/or 217, or a portion thereof, to one or more of the alkyl-demethylation zones 203, 205, and 209 can completely eliminate the need for a vapor-phase isomerization zone in the xylenes loop, resulting in an overall higher energy efficiency, and the production of more valuable, methylated aromatic hydrocarbons compared to the conventional process requiring the use of a vapor-phase isomerization zone in the xylenes loop as illustrated in FIG. 1. The conversion of a portion of the C2+-hydrocarbyl-substituted aromatic hydrocarbons in zones 203, 205, and/or 209 to methylated aromatic hydrocarbons enables the production of more xylenes compared to a conventional process of FIG. 1 where at least a portion of ethylbenzene is dealkylated in the vapor-phase isomerization zone.

As shown in FIG. 2, similar to FIG. 1, the C9+ aromatic hydrocarbons-rich stream 129 produced from the xylenes splitter 115, rich in C9, C10, and C11+ aromatic hydrocarbons compared to stream 211, is then separated in a distillation column 131 to obtain a C9-C10 aromatic hydrocarbons-rich stream 133 and a C11+ aromatic hydrocarbons-rich stream 135. Stream 135 can be conducted away and used as, e.g., motor gas blending stock, fuel oil, and the like. The C9-C10 aromatic hydrocarbons-rich stream 133 is rich in, e.g., methylated aromatic hydrocarbons such as trimethylbenzenes and tetramethylbenzenes, and C2+-hydrocarbyl-substituted aromatic hydrocarbons such as ethylmethylbenzenes, indane, ethyldimethylbenzenes, diethylbenzenes, methylindanes, tetralin, methytetralins, and the like. Stream 133, along with a benzene/toluene-rich stream 146, is then supplied into a transalkylation zone 147 having a transalkylation catalyst disposed therein. Alternatively, a portion or the entirety of stream 129 may be supplied to the transalkylation zone 147. In the presence of the transalkylation catalyst and under transalkylation conditions, the C9+ aromatic hydrocarbons react with benzene/toluene to produce xylenes. Typically, the streams 129 and 133 produced from a reformate stream as illustrated in FIG. 1 contains significant quantity of C2+-hydrocarbyl-substituted aromatic hydrocarbons. The direct transalkylation between such C9-C10 C2+-hydrocarbyl-substituted aromatic hydrocarbons and benzene/toluene would yield ethylbenzene and other C9+C2+-hydrocarbyl-substituted aromatic hydrocarbons. To increase the production of xylenes and/or benzene/toluene in the transalkylation zone 147, the transalkylation catalyst and the transalkylation conditions in the process of FIG. 1 are typically chosen such that at least a portion of the C9-C10 C2+-hydrocarbyl-substituted aromatic hydrocarbons and ethylbenzene in the transalkylation zone are converted to toluene and/or benzene via dealkylation from the aromatic rings of the C2+ alkyl groups in their entirety. The dealkylation results in the conversion of the C2+ alkyl groups into light hydrocarbon (typically in the presence of molecular hydrogen and a hydrogenation function in the dealkylation catalyst used in the transalkylation zone). The removal of the C2+ alkyl group is therefore a loss for the purpose of producing xylenes. It would be desirable to convert the C2+ alkyl group into a methyl group attached to a benzene ring—which can be then used for producing xylenes via, e.g., isomerization, transalkylation, and/or disproportionation. Similar to deethylation of ethylbenzene, effective dealkylation from the C9-C10 C2+-hydrocarbyl-substituted aromatic hydrocarbons and ethylbenzene in the transalkylation zone typically calls for vapor phase conditions which require high temperature. Such vapor-phase transalkylation is energy-intensive because the vapor effluent from the transalkylation zone needs to be cooled and condensed into liquid for the purpose of distillation separation.

In the inventive process of FIG. 2, however, due to the presence of one or more of zones 203, 205, and 209, the quantity of the C2+-hydrocarbyl-substituted aromatic hydrocarbons in streams 129 and 133 is significantly reduced compared to the corresponding streams in the process of FIG. 1, because a significant portion of such C9+C2+-hydrocarbyl-substituted aromatic hydrocarbons can be converted into methylated aromatic hydrocarbons in zones 203, 205, and/or 209. The low concentration of the C2+-hydrocarbyl-substituted aromatic hydrocarbons in streams 129 and 133 significantly reduces the need for dealkylation in transalkylation zone 147. The reduced need for dealkylation enables transalkylation in zone 147 under a significantly lower temperature than a conventional vapor-phase transalkylation process requiring dealkylation, such that a portion, or even the entirety, of the C8 aromatic hydrocarbons present in zone 147 is in liquid phase. Such partial liquid-phase or completely liquid-phase transalkylation can be much less energy intensive and much more energy efficient than the conventional full vapor-phase transalkylation necessitated by dealkylation. The conversion of a portion of the C2+-hydrocarbyl-substituted aromatic hydrocarbons in zones 203, 205, and/or 209 to methylated aromatic hydrocarbons also enables the production of more xylenes compared to a conventional process of FIG. 1 where at least a portion of the C2+-hydrocarbyl-substituted aromatic hydrocarbons are dealkylated in the transalkylation zone.

In a conventional transalkylation process including dealkylation of the C2+-hydrocarbyl-substituted aromatic hydrocarbons, a portion of the C2+ alkyl groups and/or aliphatic rings annelated to an aromatic ring are converted into light hydrocarbons, and non-aromatic hydrocarbons may be produced due to aromatic ring loss. As such, the transalkylation effluent may need to be first separated to remove such light hydrocarbons and the non-aromatic hydrocarbons (e.g., through a de-heptanizer, not shown) before being supplied to an aromatic hydrocarbon separation column (e.g., the benzene tower 141 in FIG. 1). In embodiments of the inventive process of FIG. 2, on the contrary, where dealkylation of the C2+-hydrocarbyl-substituted aromatic hydrocarbons is minimized or eliminated because of the low quantity of the C2+-hydrocarbyl-substituted aromatic hydrocarbons in stream 133, the transalkylation effluent 149 comprises those light hydrocarbons and non-aromatic hydrocarbons at such low quantities, if any at all, that effluent 149 may be directly supplied to the benzene tower 141 without an intermediate separation step to remove light hydrocarbons and non-aromatic hydrocarbons (with optional heating/cooling, and the like, as appropriate). Thus, the presence of one or more alkyl-demethylation zones in the process of FIG. 2 enables a simpler transalkylation process requiring less equipment and steps that is also less energy intensive and more energy efficient. Stream 149 in FIG. 2 can comprise, e.g., benzene, toluene, xylenes, trimethylbenzenes, tetramethylbenzenes, and the C8, C9, C10, and C11+C2+-hydrocarbyl-substituted aromatic hydrocarbons desirably at low quantities. $\geq$ In certain embodiments, $\geq 50$ wt %, or $\geq 60$ wt %, or $\geq 70$ wt %, or $\geq 80$ wt %, or $\geq 90$ wt %, or $\geq 95$ wt %, or $\geq 98$ wt %, of stream 133 are methylated aromatic hydrocarbons. The majority of the reactions in the transalkylation zone 147 thus can be exchange of methyl groups between and among the aromatic hydrocarbons such as benzene, toluene, trimethylbenzenes, and tetramethylbenzenes, resulting in the net production of xylenes and consumption of the C9-C10 methylated aromatic hydrocarbons, and benzene and/or toluene. Preferably such transalkylation is carried out in liquid phase where (i) the C8 aromatic hydrocarbons present in the transalkylation zone are substantially in liquid phase; and/or (ii) the aromatic hydrocarbons, including benzene, present in the transalkylation zone are substantially in liquid phase. The transalkylation effluent 149 can comprise benzene, toluene, xylenes, C9+ methylated aromatic hydrocarbons, and C8+C2+-hydrocarbyl-substituted aromatic hydrocarbons at low quantities.

As shown in FIG. 2, stream 149 is then supplied to benzene tower 141 to separate the aromatic hydrocarbons contained therein to obtain a benzene product stream 143, a toluene-rich stream 146 rich in toluene and/or benzene which is fed, partly or entirely, to the transalkylation zone 147, and a C8+ aromatic hydrocarbons-rich stream 145 (comprising xylenes, C9+ methylated aromatic hydrocarbons, and C8+C2+-hydrocarbyl-substituted aromatic hydrocarbons at low quantities) which is supplied to the xylenes splitter 115 as described above.

Thus, in the inventive process of FIG. 2 of this disclosure, by deploying one or more of the alkyl-demethylation zones 203, 205, and 209 in the process, quantities of the C2+-hydrocarbyl-substituted aromatic hydrocarbons entering the xylenes loop and/or the transalkylation zone can be reduced significantly. The reduced quantity of ethylbenzene in the xylenes loop reduces the need for deethylation of ethylbenzene, reduces or eliminates the need for vapor-phase isomerization, and enables liquid-phase isomerization only, resulting in (i) a simpler xylenes loop with less required equipment, lower operating temperature, lower energy intensity, and higher energy efficiency, and (ii) higher productivity of xylenes in the xylenes loop. The reduced quantity of C9+C2+-hydrocarbyl-substituted aromatic hydrocarbons in the feed to the transalkylation zone reduces the need for dealkylation of the C9+C2+-hydrocarbyl-substituted aromatic hydrocarbons, reduces or eliminates the need for vapor-phase transalkylation, and enables liquid-phase transalkylation only, resulting in (i) a simpler transalkylation process with less required equipment, lower operating temperature, lower energy intensity, and higher energy efficiency, and (ii) higher productivity of methylated aromatic hydrocarbons, particularly xylenes, in the transalkylation zone.

As shown in FIG. 2, similar to FIG. 1, the C6-C7 hydrocarbons-rich stream 111 is supplied to an extraction distillation zone 137, where a C6-C7 aromatic hydrocarbons-rich stream 139 and an aromatic hydrocarbons-depleted raffinate stream 138 are produced. Stream 138, rich in non-aromatic hydrocarbons compared to stream 111, can be conducted away and used as, e.g., a motor gas blending stock. Stream 139 is then supplied to a benzene tower 141, from which a benzene product stream 143, a toluene-rich stream 146, and a C8+ aromatic hydrocarbons-rich stream 145 are produced. The toluene-rich stream 146 (or a portion thereof) is supplied to the transalkylation 147 together with the C9-C10 aromatic hydrocarbons-rich stream 133 as described above. The C8+ aromatic hydrocarbons-rich stream 145 is then supplied to the xylenes splitter 115 along with stream 113, as described above.

In the inventive process of FIG. 2, if either or both of zones 203 and 205 is present, a portion of the C2+-hydrocarbyl-substituted aromatic hydrocarbon produced in zone 105 and/or present in stream 107 is converted into methylated aromatic hydrocarbons including toluene. For example, ethylbenzene is at least partly converted into toluene, and C9+ aromatic hydrocarbons substituted by a single C2+ alkyl group can be alkyl-demethylated to produce toluene. Toluene quantity can be increased in stream 207 in such embodiments compared to those where both zones 203 and 205 are absent. Thus, an embodiment of the inventive process including either or both of zones 203 and 205 can yield a higher quantity of toluene in streams 111, 139, and 146. As discussed above, where zone 209 is present, stream 211 contains toluene converted from, e.g., ethylbenzene and C9+ aromatic hydrocarbons single substituted with a C3+ alkyl group. The toluene present in stream 211 may be separated in the xylenes splitter 115 (not shown), and then supplied to the aromatic hydrocarbon extraction zone 137, resulting in increased quantity of toluene in streams 139 and 146. The increased production of toluene in stream 146 can be used at least partly in a transalkylation zone 147 for the production of additional quantity of xylenes, as illustrated in FIG. 2. In the comparative process shown in FIG. 1 and discussed above, however, in the absence of any of zones 203, 205, and 209, the C2+-hydrocarbyl-substituted aromatic hydrocarbons present in stream 107 are typically converted into benzene via dealkylation in the vapor-phase isomerization zone 125 and/or the vapor-phase transalkylation zone 147. Thus, the quantity of benzene product stream 143 can be lower in the process of FIG. 2 than in the conventional process of FIG. 1. While benzene is a valuable industrial chemical, the p-xylene that can be produced from the increased toluene quantity in stream 146 can be of significantly higher economic value than the reduced benzene production in stream 143.

Alternatively or additionally, at least a portion of the toluene-rich stream 146 can be supplied to a toluene disproportionation zone (now shown), where the toluene contacts a disproportionation catalyst disposed therein under disproportionation conditions to produce a disproportionation effluent rich in xylenes. Any toluene disproportionation catalyst and reaction conditions may be utilized for converting at least a portion of stream 146. The disproportionation catalyst is preferably shape-selective for the production of p-xylene over m-xylene and o-xylene, enabling a high p-xylene concentration based on all C8 aromatic hydrocarbons in the disproportionation effluent. A high-purity p-xylene product can be conveniently separated from a high p-xylene concentration C8 aromatic hydrocarbon mixture by using, e.g., a high-efficiency crystallization technology known in the art. A portion of the disproportionation effluent, such as the filtrate from the crystallization separation step, may be supplied to the p-xylene recovery sub-system 119 in FIG. 2 to produce the p-xylene product stream 121. Toluene disproportionation processes, catalysts, and conditions are described in, e.g., U.S. Pat. Nos. 5,476,823 and 6,486,373, the contents of which are incorporated herein by reference in their entirety.

Alternatively or additionally, at least a portion of the toluene-rich stream 146 and/or a portion of the benzene product stream 143 can be supplied to a methylation zone together with a methylating agent feed (now shown). On contacting a methylating catalyst disposed in the methylation zone under methylation conditions, the benzene/toluene reacts with the methylating agent to produce a methylation effluent comprising xylenes. Preferred methylating agents are methanol, dimethyl ether and mixtures thereof. The methylation zone can include a fixed bed reactor, a fluid bed reactor, a moving bed reactor, and the like. The xylenes produced in the methylation zone and present in the methylation effluent can be separated from the other components (benzene/toluene, the methylating agent, and the like), and then at least partly supplied to the p-xylene recovery sub-system 119, from which additional quantity of p-xylene product is produced in stream 121. Methylation processes, catalysts, and conditions are described in, e.g., U.S. Pat. Nos. 5,939,597 and 6,423,879, the contents of all of which are incorporated herein by reference in their entirety.

Figure 4:
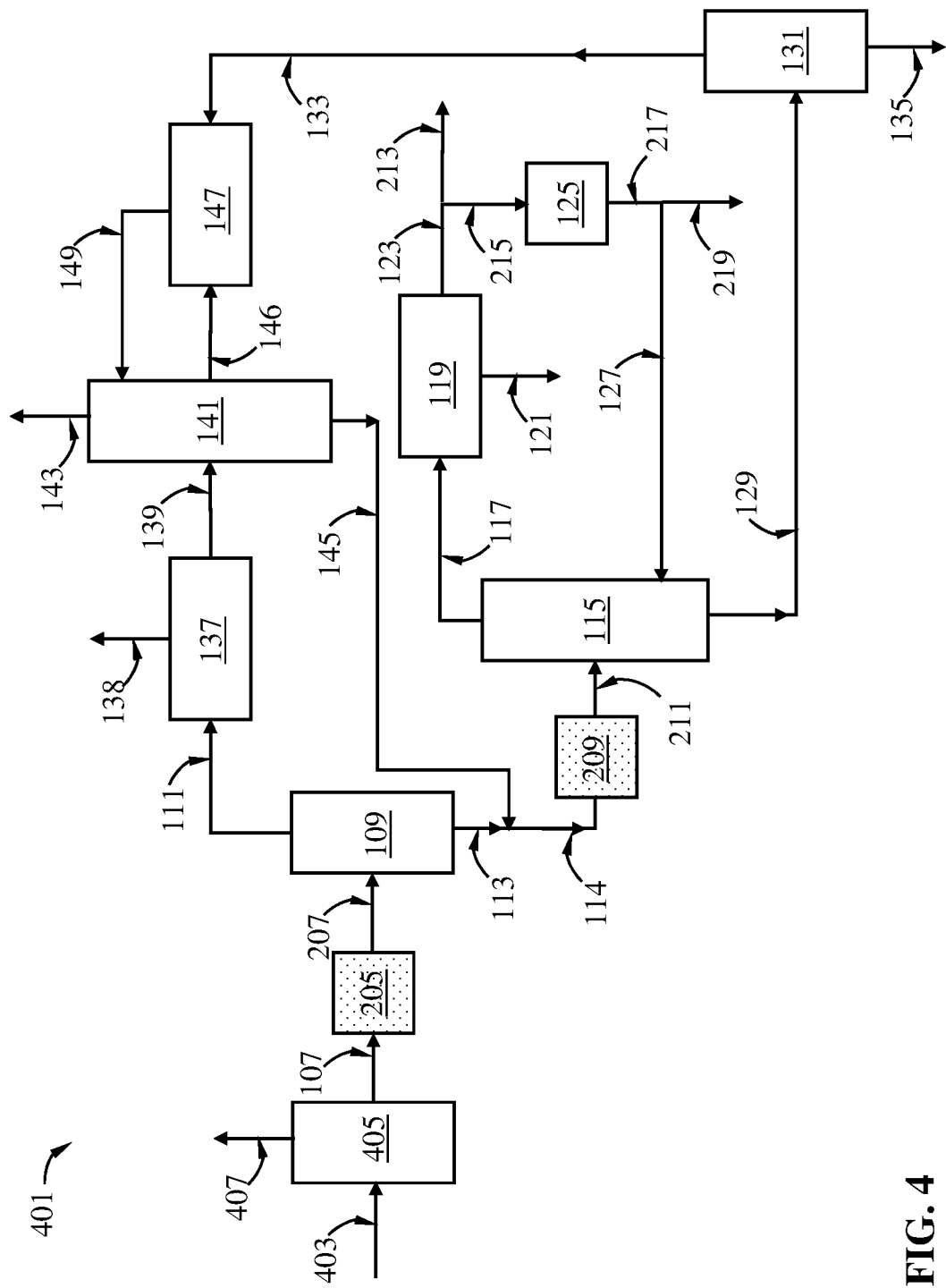
FIG. 4 is a schematic diagram showing a process of this disclosure for producing p-xylene from a hydrotreated steam-cracked naphtha stream.

FIG. 4: An Exemplary Inventive Process for Producing Xylenes from Hydrotreated Steam Cracked Naphtha ("SCN")

In a petrochemical plant, light naphtha produced from crude refining can be fed into pyrolysis reactor called a steam cracker comprising winding tube sections located in a heated furnace, where the hydrocarbons in the light naphtha are first heated in a convection zone of the winding tubes to an intermediate temperature, and then briefly heated to an elevated temperature in a radiant zone to effect pyrolysis to produce a steam cracked mixture comprising hydrogen, higher-value chemicals such as olefins (e.g., ethylene, propylene, butylenes, and the like), steam cracked naphtha, gas oil and tar. The quickly quenched steam cracked mixture upon exiting the steam cracker can be separated to obtain various olefins products, hydrogen product, fuel gas, a SCN stream, gas oil stream and a tar stream. The SCN stream, comprising aromatic and non-aromatic hydrocarbons, is typically then hydrotreated to saturate the diolefinic and olefinic non-aromatic hydrocarbons and/or the olefinic substitutes on olefinic aromatic hydrocarbons. Hydrotreating of the SCN can also abate heteroatoms (e.g., sulfur and nitrogen) present in some of the compounds present in the SCN to reduce or prevent poisoning of catalysts (e.g., an alkyl-demethylation catalyst used in a process of this disclosure) used in a downstream process. Valuable aromatic hydrocarbons can be extracted and/or produced from the thus hydrotreated SCN stream.

Figure 3:
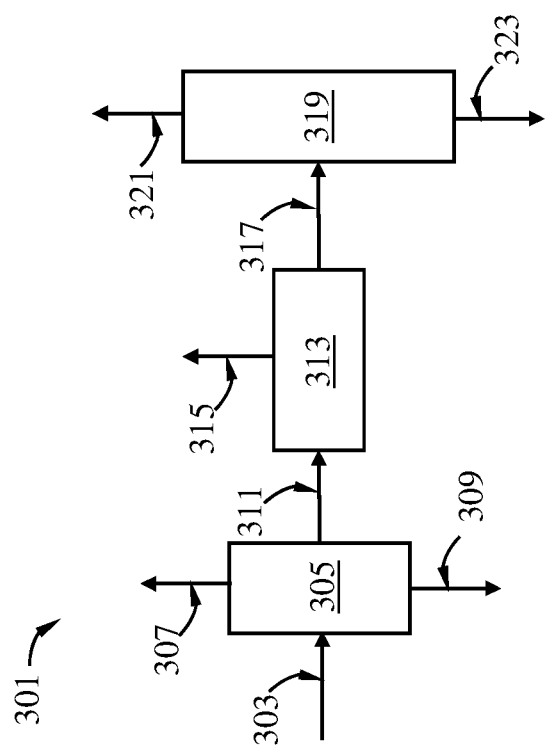
FIG. 3 is a schematic diagram showing a prior art process in processing hydrotreated steam-cracked naphtha stream.

FIG. 3 schematically illustrates a process in the prior art for processing a typical hydrotreated SCN stream. In this figure, a hydrotreated SCN stream 303 is first supplied to a separation system 305 (e.g., one or more distillation columns) to obtain a C5– hydrocarbons-rich stream 307, a C7+ hydrocarbons-rich or C8+ hydrocarbons-rich stream 309, and a benzene-rich or C6-C7 aromatic hydrocarbons-rich stream 311. Stream 311, comprising benzene and non-aromatic co-boilers thereof, and optionally toluene and non-aromatic co-boilers thereof, is then supplied to an extraction separation zone 313 to obtain an aromatic hydrocarbons-rich stream 317 consisting essentially of benzene and optionally toluene, and a non-aromatic raffinate stream 315. Stream 315 can be conducted away and used for, e.g., motor gas blending stock, fuel gas, and the like. Stream 317, if containing toluene at significant quantity, can be supplied into a benzene tower 319 to produce a benzene product stream 321 consisting essentially of benzene and a toluene-rich stream 323. Stream 309 produced from the separation sub-system 305, rich in C7+ aromatic hydrocarbons or C8+ aromatic hydrocarbons, are typically conducted away and used as, e.g., motor gas blending stock.

The C7+ aromatic hydrocarbons or C8+ aromatic hydrocarbons contained in stream 309, similar to the reformate stream produced from a heavy naphtha stream, can comprise significant quantities of the C2+-hydrocarbyl-substituted aromatic hydrocarbons, in addition to toluene, xylenes, and C9+ methylated aromatic hydrocarbons. Since p-xylene, o-xylene, toluene, and benzene products can be of higher economic value than motor gasoline blending stocks, producing one or more of these aromatic hydrocarbon products from the hydrotreated SCN stream can be of great economic interest to a petrochemical plant operating a naphtha steam cracker. Compared to typical reformate produced from heavy naphtha reforming, a hydrotreated SCN stream can comprise the C2+-alkyl-substituted aromatic hydrocarbons at an even higher weight percentage, based on the total weight of the C8+ aromatic hydrocarbons contained therein. Moreover, a hydrotreated SCN stream can comprise indane and indane derivatives at concentrations substantially higher than a reformate stream, which are difficult to convert to xylenes via transalkylation with lighter aromatic hydrocarbons. Due to the high concentrations of C2+-hydrocarbyl substituted aromatic hydrocarbons in typical hydrotreated SCN streams, they have conventionally been considered as less than desirable and even uneconomical sources for making xylene products.

FIG. 4 schematically illustrates an inventive process 401 for producing a p-xylene product and/or a benzene product from a hydrotreated SCN stream 403. In this figure, a hydrotreated SCN stream 403 is first supplied to a separation sub-system 405, from which a light hydrocarbon stream 407 rich in C5– hydrocarbons and a stream 107 rich in C6+ hydrocarbons are obtained. Stream 107 can be similar to the corresponding stream in FIG. 2, and therefore can be similarly processed by the same downstream process and equipment in FIG. 2, as shown in FIG. 4. Thus, in a petrochemical plant comprising a steam cracker and a heavy naphtha reformer, stream 107 produced from separating hydrotreated SCN in FIG. 4 can be combined with the reformate produced from a reforming zone, optionally treated together in the first alkyl-demethylation zone 205, and then supplied to the reformate splitter 109. P-xylene (and optionally o-xylene), benzene, and other potential aromatic hydrocarbon products can be produced from both the heavy naphtha stream and the hydrotreated SCN stream by the inventive process of this disclosure. In the demethylation zones 205 and/or 209, a significant portion of the C2+-hydrocarbyl-substituted aromatic hydrocarbons contained in stream 107 from the hydrotreated SCN stream 403 can be converted into methylated aromatic hydrocarbons, which, in turn, can be converted into a p-xylene product (and/or an o-xylene product). The inclusion of zones 205 and/or 209 in the process of FIG. 4 significantly reduces the quantity of the C2+-hydrocarbyl-substituted aromatic hydrocarbons in the xylenes loop and/or the C9+ aromatic hydrocarbons fed into the transalkylation zone, enables isomerization and/or transalkylation at lower temperature and/or in liquid phase, reduces or eliminates the need for complex and energy-intensive vapor-phase isomerization and/or vapor-phase transalkylation, and results in the production of products with higher value compared to the prior art process of FIG. 3 where the C7+ hydrocarbon-rich or C8+ hydrocarbon rich stream 309 is used for motor gasoline blending. To the extent stream 107 contains the C2+-hydrocarbyl-substituted aromatic hydrocarbons at a greater quantity than the corresponding stream in FIG. 2, the inclusion of zones 205 and/or 209 in the process of FIG. 4 for processing a hydrotreated SCN stream can be even more significant in the process of FIG. 4.

It may be possible to modify the inventive process of FIG. 4 to eliminate the alkyl-demethylation zones 205 and 209. In such case, to the extent stream 107 can comprise large quantities of the C2+-hydrocarbyl-substituted aromatic hydrocarbons, stream 117 can comprise ethylbenzene at large quantity, and streams 129/133 can comprise C9+C2+-hydrocarbyl-substituted aromatic hydrocarbons at large quantity, necessitating the use of vapor-phase isomerization in the isomerization zone 125 to effect ethylbenzene deethylation and vapor-phase transalkylation in the transalkylation zone 147 to effect dealkylation of the C9+ aromatic hydrocarbons, resulting in (i) a more energy-intensive and less energy efficient xylenes loop; (ii) a more energy-intensive and less energy efficient transalkylation process; and (iii) the production of less quantity of valuable products such as p-xylene, compared to the process illustrated in FIG. 4 including one or both of the alkyl-demethylation zones 205 and 209.

Heavy naphtha, and indeed even crude oil or a fraction thereof (e.g., a fraction separated by using a flashing drum), may be subject to pyrolysis such as stream cracking, to produce a hydrocarbon mixture comprising C6+ aromatic hydrocarbons including C8 aromatic hydrocarbons. Any C6+ aromatic hydrocarbons in the hydrocarbon mixture may be used in lieu or in combination with a hydrotreated SCN stream 401 in the process illustrated in FIG. 4 and similar processes of this disclosure, even if such C6+ aromatic hydrocarbons may comprise C2+-hydrocarbyl substituted aromatic hydrocarbons at elevated levels.

Figure 5:
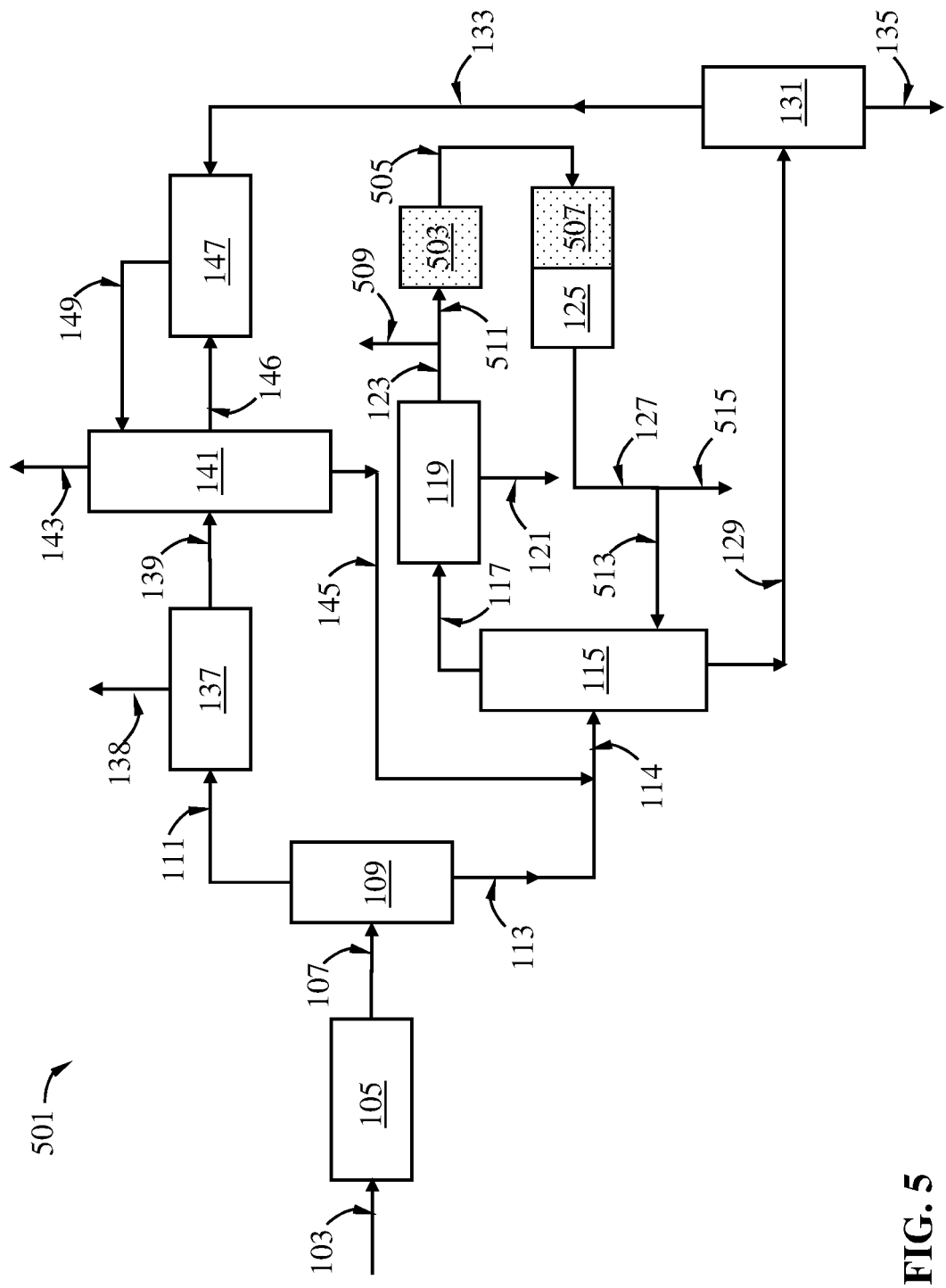
FIG. 5 is a schematic diagram showing a C8 aromatic hydrocarbon isomerization process of this disclosure for isomerizing a C8 aromatic hydrocarbon mixture including one or more ethyl-demethylation steps.

FIG. 5: An Exemplary Inventive Process for Isomerizing C8 Aromatics

Another aspect of this disclosure relates to a C8 aromatic hydrocarbon isomerization process, an example 501 of which is schematically illustrated in FIG. 5 as an adaptation of the prior art process shown in FIG. 1.

In FIG. 5, similar to FIG. 1, stream 114, a combination of streams 113 and 145, is fed into a xylenes splitter 115, from which a xylenes-rich stream 117 and a C9+ aromatic hydrocarbons-rich stream 129 are produced. The xylenes-rich stream 117 comprises the xylenes and ethylbenzene. The concentration of ethylbenzene in stream 117 in FIG. 5 can range from $c(EB)5$ to $c(EB)6$ wt %, based on the total weight of the C8 aromatic hydrocarbons contained in stream 117, where $c(EB)5$ and $c(EB)6$ can be, independently, e.g., 2, 4, 5, 6, 8, 10, 12, 14, 15, 16, 18, 20, 22, 24, 25, 26, 28, 30, 32, 34, 35, 36, 38, 40, as long as $c(EB)5<c(EB)6$. In certain cases the ethylbenzene concentration can be high such that that $c(EB)5 \geq 10$, $c(EB)5 \geq 15$, $c(EB)5 \geq 20$, or even $c(EB)5 \geq 25$. Stream 117 in FIG. 5 can comprise p-xylene at $\geq$ various concentrations, depending on the composition(s) of the C8+ aromatic hydrocarbons-rich stream(s) supplied to the xylenes splitter 115. For example, stream 117 can comprise p-xylene at a concentration from $c(pX)5$ to $c(pX)6$ wt %, based on the total weight of the C8 aromatic hydrocarbons contained in stream 117, where $c(pX)6$ and $c(pX)7$ can be, independently, e.g., 15, 16, 18, 20, 22, 24, 25, 26, 28, 30, 32, 34, 35, 36, 38, 40, 42, 44, 45, 48, 50, 52, 54, 55, 56, 58, 60, as long as $c(pX)6<c(pX)7$.

As shown in FIG. 5, similar to the convention process of FIG. 1, the xylenes-rich stream 117 produced from the xylenes splitter 115 is then supplied to a first p-xylene recovery sub-system 119, from which a first p-xylene product stream 121 rich in p-xylene and a first p-xylene depleted stream 123 are produced. The first p-xylene depleted stream 123, rich in m-xylene, o-xylene, and ethylbenzene compared to stream 117, partly (shown as stream 511) or entirely, is then supplied to an optional alkyl-demethylation (i.e., primarily an ethyl-demethylation) zone 503 having an alkyl-demethylation catalyst (i.e., an ethyl-demethylation catalyst) disposed therein. FIG. 5 shows that stream 123 is split into streams 509 and 511. Stream 509 or a portion thereof, especially if containing ethylbenzene at a very high concentration, can be conducted away as a purge stream and used as, e.g., motor gasoline blending stock. Additionally or alternatively, stream 509 or a portion thereof may be supplied to an optional isomerization zone (not shown) directly such as a vapor-phase isomerization zone comprising an isomerization catalyst housed therein. On contacting the isomerization catalyst and under isomerization conditions, the xylenes present in stream 509 isomerize to form additional p-xylene, and a portion of ethylbenzene therein may be de-ethylated to reduce the ethylbenzene quantity in the xylenes loop. The isomerization effluent from such optional isomerization zone, or a portion thereof, may be then supplied to the xylenes splitter 115.

On contacting the alkyl-demethylation catalyst and under alkyl-demethylation conditions, a portion of the ethylbenzene contained in stream 511 is demethylated to form toluene. The alkyl-demethylation effluent 505 exiting zone 503 is therefore depleted in ethylbenzene compared to stream 511. Stream 505 is then supplied into an optional alkyl-demethylation zone 507 having another alkyl-demethylation catalyst disposed therein under another set of alkyl-demethylation conditions to effect additional ethyl-demethylation of ethylbenzene. The alkyl-demethylation catalysts, and the alkyl-demethylation conditions in zones 503 and 507 may be the same or different if both zones are present. While either of zones 503 and 507 may be absent, at least one is present in the xylenes loop to effect ethyl-demethylation of ethylbenzene. The ethyl-demethylation zone 507 and the isomerization zone 125 may be present in separate vessels. Alternatively, zones 507 and 125 may be separate but housed in the same vessel (e.g., where a bed of the ethyl-demethylation catalyst in zone 507 is located upstream of a bed of the isomerization catalyst in zone 125 in a common reactor housing). Alternatively, zones 507 and 125 can partly overlap in the same vessel (e.g., where a portion, but not all, of the ethyl-demethylation catalyst in zone 207 is mixed with a portion, but not all, of the isomerization catalyst in zone 125). Alternatively, zones 507 and 125 may be substantially the same zone (e.g., where the ethyl-demethylation catalyst in zone 507 is admixed with the isomerization catalyst in zone 125 in their entireties in a common reactor housing; or where a common catalyst capable of performing the isomerization and ethyl-demethylation functions simultaneously). In the isomerization zone 125, m-xylene and/or o-xylene are isomerized to form additional p-xylene in the presence of a first isomerization catalyst under a first set of isomerization conditions. The isomerization zone 125 may be operated in liquid-phase conditions, vapor-phase conditions, or mixed-phase conditions.

The isomerization effluent 127, or a portion thereof (shown as stream 513), is then supplied to the xylenes splitter 115. The xylenes splitter 115, the p-xylene recovery sub-system 119, and the isomerization zone 125 form a xylenes-loop.

In the conventional process of FIG. 1, if the isomerization zone 125 does not have the sufficient capability to convert the ethylbenzene contained in stream 123, then ethylbenzene can undesirably accumulate in the xylenes loop overtime to a high concentration. To prevent ethylbenzene accumulation in the xylenes loop, especially where streams 113, 145, 117, and 123 comprise ethylbenzene at substantial concentrations (e.g., $\geq$10 wt %, based on the total weight of the C8 aromatics contained therein), typically the isomerization catalyst and the isomerization conditions in the isomerization zone in the conventional process of FIG. 1 are chosen such that at least a portion of the ethylbenzene is converted to benzene via deethylation under vapor-phase isomerization conditions. As a result of deethylation, the ethyl group in an ethylbenzene molecule is converted into ethane (in the presence of molecular hydrogen and a hydrogenation function in the deethylation catalyst used in the isomerization zone). The result of deethylation of ethylbenzene is the loss of an ethyl substitute connected to a benzene ring. Conducting xylenes isomerization substantially in vapor phase requires heating the hydrocarbons in the isomerization zone to a high temperature and subsequent cooling and condensing the isomerization effluent to liquid state for separation in the xylenes splitter 115, and therefore is energy intensive.

As shown in FIG. 5, to the extent streams 123 and 505 may comprise ethylbenzene at substantial quantity (e.g., where zone 503 is absent), one may operate the first isomerization zone 125 in FIG. 5 under vapor-phase conditions to covert at least a portion of the ethylbenzene via deethylation, so that ethylbenzene quantity in the xylenes loop does not become overly high, similar to the conventional process of FIG. 1 including an isomerization zone operated under vapor-phase conditions. Thus, in one embodiment, zone 503 is absent, zone 507 is present adjacent to or overlapping partly or entirely with zone 125, and zone 125 is operated under vapor-phase isomerization conditions.

In embodiments where ethyl-demethylation zone 503 is present, a portion of stream 505 may be recycled (not shown) back to zone 503 to enable a high conversion of ethylbenzene in zone 503.

In another embodiment, the ethyl-demethylation zone 503 is present, zone 507 is absent, stream 505 is separated to remove light hydrocarbons produced in zone 503 before being supplied to the isomerization zone 125, and zone 125 is operated in liquid-phase conditions. In such embodiments, because a portion of ethylbenzene in stream 511 is converted to toluene via ethyl-demethylation in zone 503, stream 505 is depleted in ethylbenzene. The need for deethylation of ethylbenzene in the isomerization zone 125 is thus reduced, and hence the need for vapor-phase isomerization conditions in zone 205 is reduced. Accordingly, at least a portion, desirably a majority, and even the entirety, of the p-xylene-depleted stream 123 can be processed in zone 125 under liquid-phase isomerization conditions. Because such liquid-phase isomerization is conducted under an operation temperature significantly lower than that in a conventional vapor-phase isomerization required in the process of FIG. 1, and hence is much less energy intensive, and more energy efficient.

The first isomerization effluent 127 exiting the first isomerization zone 125 is rich in p-xylene compared to stream 505. To recover the p-xylene from stream 217, a part (as shown as stream 127) or the entirety (not shown) of stream 217 is then supplied to the xylenes splitter. If zone 125 is operated under vapor-phase isomerization conditions, stream 217 may comprise, in addition to aromatic hydrocarbons such as xylenes and ethylbenzene, light hydrocarbons resulting from deethylation and non-aromatic hydrocarbons. Before being fed into the xylenes splitter 115, streams 217 and/or 127 may be separated to remove such light hydrocarbons and non-aromatic hydrocarbons (not shown). If zone 125 is operated under liquid-phase isomerization conditions without deethylation of ethylbenzene, stream 217 tends to comprise such light hydrocarbons and non-aromatic hydrocarbons at quantities significantly lower than a corresponding effluent stream exiting an isomerization zone under vapor-phase conditions, if any at all. Thus, stream 217 exiting a liquid-phase isomerization zone 125, or a portion thereof (shown as stream 127), can be directly supplied to the xylenes splitter 115 without an intermediate separation step (with optional heating/cooling, and the like). Isomerizing substantially the entirety of the p-xylene-depleted stream 123 only in a liquid-phase isomerization zone without using a vapor-phase isomerization zone clearly results in a simpler, less energy-intensive, and more energy-efficient xylenes loop compared to the conventional process of FIG. 1 necessitating a vapor-phase isomerization zone.

As shown in FIG. 5, the first isomerization effluent 127 is split into streams 513 and 515. Stream 513, or a portion thereof, after optional further intermediate separation as appropriate, is supplied to the xylenes splitter 115. Stream 515 or a portion thereof can be conducted away as a purge stream and used for, e.g., motor gas blending, especially where stream 515 comprises ethylbenzene at a high concentration. Additionally or alternatively, stream 515 or a portion thereof can be recycled (not shown) to one or more of zones 503 and 507 (if present), and preferably to zone 503 (if present), where the ethylbenzene contained therein can be further converted via ethyl-demethylation. Additionally or alternatively, stream 515 or a portion thereof can be recycled (not shown) directly to the p-xylene recovery sub-system 119, bypassing the xylenes splitter 115, to recover a portion of p-xylene therein. Bypassing the xylenes splitter can further improve the energy efficiency of the xylenes loop. The isomerization effluent from a vapor-phase isomerization zone typically contains light hydrocarbons and other non-aromatic hydrocarbons generated from, e.g., dealkylation, and therefore is not directly recycled to the p-xylene recovery sub-system without an intermediate separation step, e.g., in a deheptanizer and/or the xylenes splitter 115. Conversely, the isomerization effluent produced from a liquid phase isomerization zone 125 contains such light hydrocarbons and other non-aromatic hydrocarbons at much lower concentrations than in a typical vapor-phase isomerization effluent, if any at all, and therefore can be directly recycled to the p-xylene recovery sub-system to recover additional p-xylene formed in the isomerization zone, bypassing the xylenes splitter. A liquid-phase isomerization zone 125 in combination with one or both of the ethyl-demethylation zones 503 and 507 can completely eliminate the need for a vapor-phase isomerization zone in the xylenes loop, resulting in an overall higher energy efficiency, and the production of more valuable, methylated aromatic hydrocarbons compared to the conventional process requiring the use of a vapor-phase isomerization zone in the xylenes loop as illustrated in FIG. 1. The conversion of a portion of the C2+-hydrocarbyl-substituted aromatic hydrocarbons in zones 503 and/or 507 to methylated aromatic hydrocarbons enables the production of more xylenes compared to a conventional process of FIG. 1 where at least a portion of ethylbenzene is dealkylated in the vapor-phase isomerization zone.

While the process in FIG. 5 does not include an alkyl-demethylation zone at the locations of zones 203, 205, and 209 in the processes of FIG. 2 or 3, in certain embodiments, it may be desirable to additionally provide an alkyl-demethylation zone to the process of FIG. 5 in one or more of the locations 203, 205, and 209 in the processes of FIG. 2 or 3. In such embodiments, high energy efficiency in the xylenes loop including liquid-phase isomerization, high energy efficiency in the transalkylation process including liquid-phase transalkylation, and high quantity of xylene products can be produced.

Figure 6:
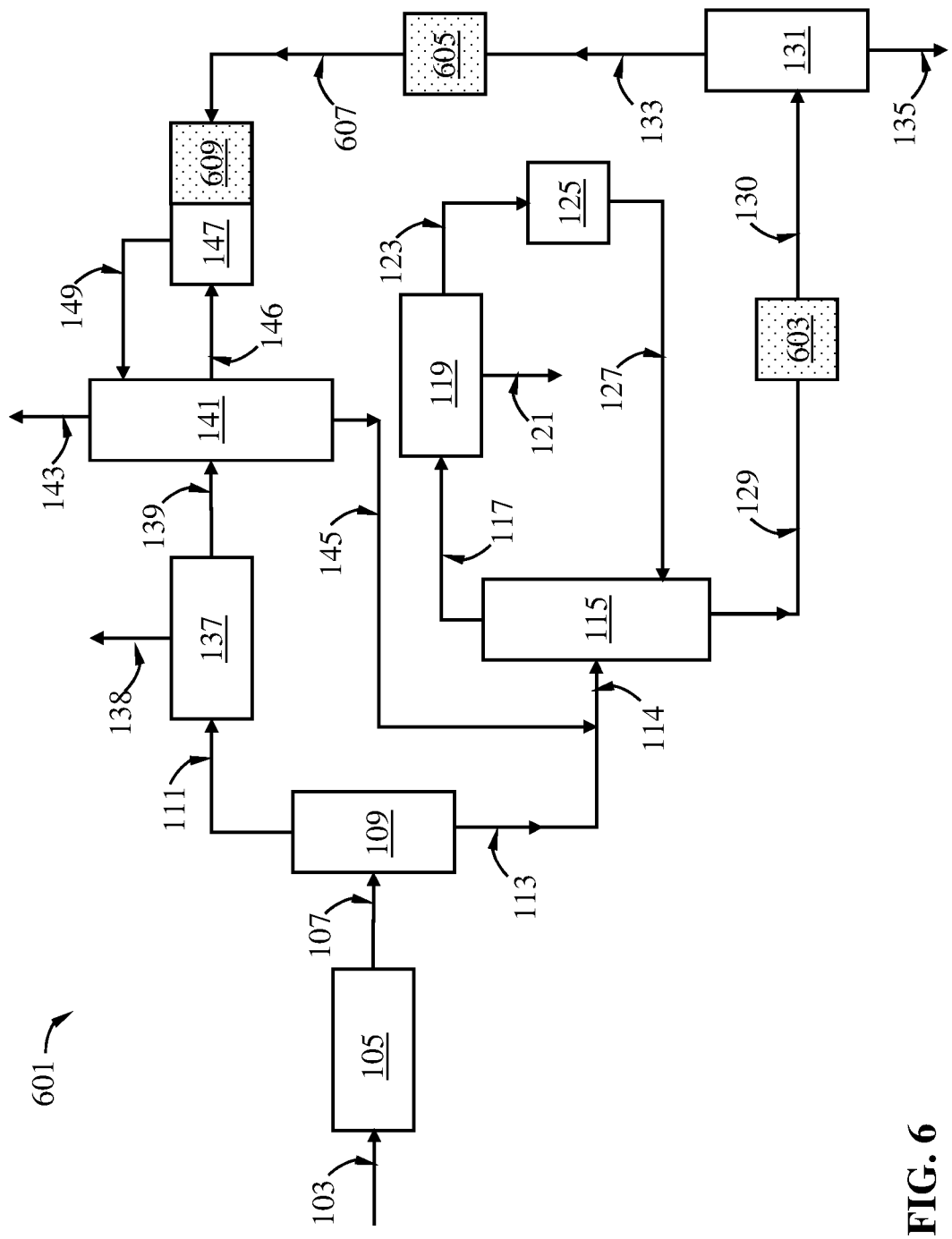
FIG. 6 is a schematic diagram showing a transalkylation process of this disclosure for transalkylating a C9+ aromatic hydrocarbon with benzene and/or toluene including one or more alkyl-demethylation steps.

FIG. 6: An Exemplary Inventive Transalkylation Process

Another aspect of this disclosure relates to a transalkylation process, an example of which is schematically illustrated in FIG. 6.

As shown in FIG. 6, similar to FIG. 1, the C9+ aromatic hydrocarbons-rich stream 129 produced from the xylenes splitter 115, rich in C9, C10, and C11+ aromatic hydrocarbons compared to stream 114, can comprise significant quantity of the C2+-hydrocarbyl-substituted aromatic hydrocarbons in addition to methylated aromatic hydrocarbons. In FIG. 6, stream 129 can be first supplied to an optional alkyl-demethylation zone 603 (if present) comprising an alkyl-demethylation catalyst disposed therein. On contacting the alkyl-demethylation catalyst and under alkyl-demethylation conditions, the C2+-hydrocarbyl-substituted aromatic hydrocarbons undergo alkyl-demethylation reactions. As a result, the alkyl-demethylation effluent 130 exiting zone 603 is depleted in the C2+-hydrocarbyl-substituted aromatic hydrocarbons and rich in methylated aromatic hydrocarbons compared to stream 129. The presence of zone 603 enables the conversion of certain C11+C2+-hydrocarbyl-substituted aromatic hydrocarbons present in stream 129 to useful C9-C10 aromatic hydrocarbons in streams 129 and 133. Without zone 603, those C11+C2+-hydrocarbyl-substituted aromatic hydrocarbons converted in zone 603 would mostly enter stream 135 and become lost. The conversion of C9+C2+-hydrocarbyl-substituted aromatic hydrocarbons in zone 603 results in the formation of light hydrocarbons, C8 aromatic hydrocarbons, toluene, and optionally benzene.

Stream 130, after optional removal of light hydrocarbons, is then separated in a distillation column 131 to obtain a C9-C10 aromatic hydrocarbons-rich stream 133 (also containing C6-C8 aromatic hydrocarbons formed in zone 603 if present) and a C11+ aromatic hydrocarbons-rich stream 135. Stream 135 can be conducted away and used as, e.g., motor gas blending stock, fuel oil, and the like. The C9-C10 aromatic hydrocarbons-rich stream 133 comprises, e.g., methylated aromatic hydrocarbons such as trimethylbenzenes and tetramethylbenzenes, and C2+-hydrocarbyl-substituted aromatic hydrocarbons such as ethylmethylbenzenes, indane, ethyldimethylbenzenes, diethylbenzenes, tetralin, methylindanes, and methyltetralins. Stream 133 is then supplied into an optional alkyl-demethylation zone 605 comprising an alkyl-demethylation catalyst disposed therein. On contacting the alkyl-demethylation catalyst and under alkyl-demethylation conditions in zone 605, the C2+-hydrocarbyl-substituted aromatic hydrocarbons undergo alkyl-demethylation reactions to produce an additional quantity of methylated aromatic hydrocarbons and/or benzene. Effluent 607 exiting zone 605 is thus depleted in the C2+-hydrocarbyl-substituted aromatic hydrocarbons and rich in methylated aromatic hydrocarbons compared to stream 133.

As shown in FIG. 6, stream 607 is then supplied into an optional alkyl-demethylation zone 609 comprising an alkyl-demethylation catalyst disposed therein. Upon contacting the alkyl-demethylation catalyst under alkyl-demethylation conditions in zone 609, a portion of the remaining C2+-hydrocarbyl-substituted aromatic hydrocarbons in stream 607 is then converted to methylated aromatic hydrocarbons and/or benzene. The optional zone 609 can be upstream and separate from the transalkylation zone 147 (e.g., where the alkyl-demethylation catalyst in zone 609 and the transalkylation catalyst in zone 147 are located in separate vessels, or in separate beds in a common vessel). Alternatively, the optional zone 609 can overlap partly with zone 147 (e.g., where the alkyl-demethylation catalyst in zone 609 and the transalkylation catalyst in zone 147 are partly admixed in a common vessel). Alternatively, the zones 609 and 147 are the same zone (e.g., where the alkyl-demethylation catalyst and the transalkylation catalyst are entirely admixed in a single mixed catalyst bed, or a single catalyst performs the dual functions of alkyl-demethylation and transalkylation).

The alkyl-demethylation effluent from zone 609 can be directly used for transalkylation in the transalkylation zone 147.

One or more of the alkyl-demethylation zones 603, 605, and 609 is present in the transalkylation process of this disclosure.

A toluene-rich stream 146 is also supplied into transalkylation zone 147. In the presence of the transalkylation catalyst and under transalkylation conditions, the C9+ aromatic hydrocarbons react with benzene/toluene to produce xylenes. The streams 129 and 133, produced from a reformate stream as illustrated in FIG. 1 and/or hydrotreated SCN, can contain significant quantity of the C2+-hydrocarbyl-substituted aromatic hydrocarbons. The direct transalkylation between such C9-C10 C2+-hydrocarbyl-substituted aromatic hydrocarbons and benzene/toluene would yield ethylbenzene and other C9+C2+-hydrocarbyl-substituted aromatic hydrocarbons. To increase the production of xylenes and/or benzene/toluene in the transalkylation zone 147, the transalkylation catalyst and the transalkylation conditions in the process of FIG. 1 are typically chosen such that at least a portion of the C9-C10 C2+-hydrocarbyl-substituted aromatic hydrocarbons and ethylbenzene in the transalkylation zone are converted to toluene and/or benzene via dealkylation from the aromatic rings of the C2+ alkyl groups in their entirety. The dealkylation results in the conversion of the C2+ alkyl groups into light hydrocarbons (typically in the presence of molecular hydrogen and a hydrogenation function in the dealkylation catalyst used in the transalkylation zone). The removal of the C2+ alkyl group is therefore a loss for the purpose of producing xylenes. It would be desirable to convert the C2+ alkyl group into a methyl group attached to a benzene ring—which can be then used for producing xylenes via, e.g., isomerization, transalkylation, and/or disproportionation. Similar to deethylation of ethylbenzene, effective dealkylation from the C9-C10 C2+-hydrocarbyl-substituted aromatic hydrocarbons and ethylbenzene in the transalkylation zone typically calls for vapor phase conditions which require high temperature. Such vapor-phase transalkylation is energy-intensive because the vapor effluent from the transalkylation zone needs to be cooled and condensed into liquid for the purpose of distillation separation.

In the inventive process of FIG. 5, due to the presence of one or more of zones 603, 605, and 609, the quantity of the C2+-hydrocarbyl-substituted aromatic hydrocarbons entering or present in the transalkylation zone 147 is significantly reduced compared to the process of FIG. 1, because a significant portion of such C9+C2+-hydrocarbyl-substituted aromatic hydrocarbons in stream 129 can be converted into methylated aromatic hydrocarbons in zones 603, 605, and/or 609. The low concentration of the C2+-hydrocarbyl-substituted aromatic hydrocarbons in the transalkylation zone significantly reduces the need for dealkylation in transalkylation zone 147. The reduced need for dealkylation enables transalkylation in zone 147 under a significantly lower temperature than a conventional vapor-phase transalkylation process requiring dealkylation, such that a portion, or even the entirety, of the aromatic hydrocarbons present in zone 147 is in liquid phase. Such partial liquid-phase or completely liquid-phase transalkylation can be much less energy intensive and much more energy efficient than the conventional full vapor-phase transalkylation necessitated by dealkylation. The conversion of a portion of the C2+-hydrocarbyl-substituted aromatic hydrocarbons in zones 603, 605, and/or 609 to methylated aromatic hydrocarbons also enables the production of more xylenes compared to a conventional process of FIG. 1 where at least a portion of the C2+-hydrocarbyl-substituted aromatic hydrocarbons are dealkylated in the transalkylation zone. In a conventional process of FIG. 1 in the absence of zones 603, C11+C2+-hydrocarbyl-substituted aromatic hydrocarbons present in stream 129 exits separation column 131 in stream 135 and therefore will not be used for transalkylation for the purpose of making xylenes. In an embodiment of the transalkylation process of this disclosure including zone 603, as discussed above, a portion of the C11+C2+-hydrocarbyl-substituted aromatic hydrocarbons present in stream 129 is alkyl-demethylated to make C10− aromatic hydrocarbons, which will exit separation column 131 in stream 133 and eventually can be converted into useful xylenes and/or benzene product(s) through the optional zones 605 and 609, and finally the transalkylation zone 147. Therefore, if streams 113, 114, and/or 129 comprise C11+C2+-hydrocarbyl-substituted aromatic hydrocarbons at significant quantity, an inventive transalkylation process of this disclosure including the alkyl-demethylation zone 603 is highly advantageous because, among others, more methylated aromatic hydrocarbons such as xylenes and/or benzene can be produced.

In a conventional transalkylation process including dealkylation of the C2+-hydrocarbyl-substituted aromatic hydrocarbons, a portion of the C2+ alkyl groups and/or aliphatic rings annelated to an aromatic ring are converted into light hydrocarbons, and non-aromatic hydrocarbons may be produced due to aromatic ring loss. As such, the transalkylation effluent may need to be first separated to remove such light hydrocarbons and the non-aromatic hydrocarbons (e.g., through a de-heptanizer, not shown in FIG. 1) before being supplied to an aromatic hydrocarbon separation column (e.g., the benzene tower 141 in FIG. 1). In embodiments of the inventive process of FIG. 6, on the contrary, where dealkylation of the C2+-hydrocarbyl-substituted aromatic hydrocarbons is minimized or eliminated because of the low quantity of the C2+-hydrocarbyl-substituted aromatic hydrocarbons in stream 607 and/or the transalkylation zone 147, the transalkylation effluent 149 comprises those light hydrocarbons and non-aromatic hydrocarbons at such low quantities, if any at all, that effluent 149 may be directly supplied to the benzene tower 141 without an intermediate separation step to remove light hydrocarbons and non-aromatic hydrocarbons (with optional heating/cooling, and the like, as appropriate). Thus, the presence of one or more alkyl-demethylation zones 603, 605, and 609 in the process of FIG. 6 enables a simpler transalkylation process requiring less equipment and steps that is also less energy intensive and more energy efficient. Stream 149 in FIG. 6 can comprise, e.g., benzene, toluene, xylenes, trimethylbenzenes, tetramethylbenzenes, and the C8, C9, C10, and C11+C2+-hydrocarbyl-substituted aromatic hydrocarbons desirably at low quantities.

In certain embodiments, $\geq 50$ wt %, or $\geq 60$ wt %, or $\geq 70$ wt %, or $\geq 80$ wt %, or $\geq 90$ wt %, or $\geq 95$ wt %, or $\geq 98$ wt %, of stream 607 are methylated aromatic hydrocarbons. The majority of the reactions in the transalkylation zone 147 thus can be exchange of methyl groups between and among the aromatic hydrocarbons such as benzene, toluene, trimethylbenzenes, and tetramethylbenzenes, resulting in the net production of xylenes and consumption of the C9-C10 methylated aromatic hydrocarbons, and benzene and/or toluene. Preferably such transalkylation is carried out in liquid phase where (i) the C8 aromatic hydrocarbons present in the transalkylation zone are substantially in liquid phase; and/or (ii) the aromatic hydrocarbons, including benzene, present in the transalkylation zone are substantially in liquid phase. The transalkylation effluent 149 can comprise benzene, toluene, xylenes, C9+ methylated aromatic hydrocarbons, and C8+C2+-hydrocarbyl-substituted aromatic hydrocarbons at low quantities.

As shown in FIG. 6, stream 149 is then supplied to benzene tower 141 (along with other streams such as stream 139) to separate the aromatic hydrocarbons contained therein to obtain a benzene product stream 143, a toluene-rich stream 146 rich in toluene and/or benzene which is fed, partly or entirely, to the transalkylation zone 147, and a C8+ aromatic hydrocarbons-rich stream 145 (comprising xylenes, C9+ methylated aromatic hydrocarbons, and C8+C2+-hydrocarbyl-substituted aromatic hydrocarbons preferably at low quantities) which is supplied to the xylenes splitter 115 as described above.

This disclosure is further illustrated by the following non-limiting Examples.

EXAMPLES

Part A: Fabrication of Alkyl-Demethylation Catalyst

Alumina support used to prepare catalysts was purchased from Sasol (SBa-200, gamma-phase alumina). Catalysts A1, A2, A3, A4, A5, and A6 were prepared using the following method: The alumina support was pre-calcined at 500° C. for 6 hours in air. Rh metal was added to the support by incipient wetness impregnation (IWI) of Rh(III) nitrate from BASF in aqueous solution. The Rh(III) nitrate solutions were added to the IWI point of each support (0.5-1.0 g solution/g support) to give the specified metal loading. The samples were then dried at 120° C. for 16 hours, then calcined in air at 600° C. for 6 hours. Catalyst A7 was prepared using a method similar to the one described above, except the alumina support was first treated with a 3-5 mol % La(III) nitrate aqueous solution in order to incorporate La into the alumina support prior to pre-calcination at 500° C. for 6 hours in air. Catalyst A8 was prepared similar to Catalyst A7 except the alumina support following treatment with a 3-5 mol % La(III) nitrate aqueous solution was subject to pre-calcination at 1200° C. for 8 hours in air in order to convert the gamma-phase alumina to theta-phase alumina. It is hypothesized that La doping in alumina may help in stabilizing and promoting desirable theta-phase formation achieving optimized physical and chemical properties. The La dopant is believed to reside in the vacant octahedral locations within the alumina lattice, hence stabilizing the alumina and preventing undesired loss of pore volume and surface area due to high temperature treatment at 1200° C. The compositions of catalysts A1-A8 are listed below, where the Rh concentration is expressed as the percentage of Rh based on the total weight of the catalyst composition:

| A1 | Rh(0.1%)/Alumina(gamma) |
|---|---|
| A2 | Rh(0.7%)/Alumina(gamma) |
| A3 | Rh(0.9%)/Alumina(gamma) |
| A4 | Rh(1.8%)/Alumina(gamma) |
| A5 | Rh(2.0%)/Alumina(gamma) |
| A6 | Rh(3.5%)/Alumina(gamma) |
| A7 | Rh(3.5%)/La-Alumina(gamma) |
| A8 | Rh(3.5%)/La-Alumina(theta) |

Part B: Processes for Producing p-Xylene

In these examples, "C2-A" means aromatic hydrocarbons comprising an ethyl group attached to a benzene ring; "C2-A conversion" means the conversion of aromatic hydrocarbons comprising an ethyl group attached to a benzene ring by deethylation and/or ethyl-demethylation as previously defined; "C3-A" means aromatic hydrocarbons comprising an C3 alkyl group attached to a benzene ring; "C3-alkyl-aromatics conversion" means the conversion of aromatic hydrocarbons comprising a C3 alkyl group attached to a benzene ring by dealkylation and/or alkyl-demethylation as previously defined. TMZ means trimethylbenzenes.

Example B1 (Comparative): Conventional Process of FIG. 1 in the Absence of any Alkyl-Demethylation Zone Simulation of a process for producing p-xylene from naphtha reforming of FIG. 1 in the absence of any alkyl-demethylation zone was performed. Substantial quantity of the C2+-hydrocarbyl-substituted aromatic hydrocarbons are present in streams 107, 113, 114, 117, and 123, 129, 123. The process utilizes a vapor-phase isomerization zone to process the 50 wt % of the p-xylene-depleted stream 123 and a liquid-phase isomerization zone running in parallel with the vapor-phase isomerization zone to process the remaining 50 wt %. Ethylbenzene in stream 123 supplied into the vapor-phase isomerization zone 123 is subject to deethylation therein. Furthermore, the process utilizes a vapor-phase transalkylation zone to process stream 133 (heavy aromatics) along with stream 146 (toluene) to produce mixed xylenes and benzene. C9+C2+-hydrocarbyl-substituted aromatic hydrocarbons in stream 133 supplied to the vapor-phase transalkylation zone are subject to dealkylation therein. Process assumptions and simulation results are reported in TABLE I below.

Example B2 (Inventive): Inventive Process of FIG. 2 in the Presence of Alkyl-Demethylation Zone 209

Simulation of a process for producing p-xylene from naphtha reforming of FIG. 2 with the exception that stream 145 is fed directly to the xylenes splitter 115 instead of to the alkyl-demethylation zone 209, wherein the alkyl-demethylation zones 203 and 205 are absent, and the alkyl-demethylation zone 209 is present, was performed. The quantity of stream 113 and its composition in this Example B2 are the same as those in Example B1 above. In the process of this Example B2, in zone 209, a portion of ethylbenzene and C9+C2+-hydrocarbyl-substituted aromatic hydrocarbons and converted to toluene, xylenes, trimethylbenzenes and other methylated aromatic hydrocarbons. As such, the xylenes stream 117 and the p-xylene-depleted streams 123 in FIG. 2 comprise ethylbenzene at a reduced concentration compared to their corresponding streams in FIG. 1. At high enough conversion of ethylbenzene in Zone 209, vapor-phase isomerization of stream 123, and deethylation of ethylbenzene there in, becomes unnecessary. As such, in this Example, the entirety of stream 123 is fed into a liquid-phase isomerization zone 125. The isomerization effluent 217, in turn, is supplied to the xylenes splitter 115 in its entirety. A purge stream 213 may be optionally recycled back to zone 209. Furthermore, the C9+ stream 129 and the resulting stream 133 in FIG. 2 comprise C9+C2+-hydrocarbyl-substituted aromatic hydrocarbons at a reduced concentration compared to their corresponding streams in FIG. 1. Dealkylation of any remaining C9+C2+-hydrocarbyl-substituted aromatic hydrocarbons is affected in Zone 147 vapor-phase transalkylation. While not assumed in this example, it is speculated that vapor-phase transalkylation of stream 144, and dealkylation of C9+C2+-hydrocarbyl-substituted aromatic hydrocarbons there in, may become unnecessary enabling the use of a liquid phase transalkylation zone 147, in combination with or replacing a vapor-phase transalkylation zone 147. Additional process assumptions and simulation results are reported in TABLE I below.

Example B3 (Comparative): Modified Process of Example B2 Above Wherein Zone 209 is Replaced by an Dealkylation Zone The process simulated in this Example B3 differs from that in Example B2 only in that the alkyl-demethylation zone 209 is replaced by a dealkylation zone at the same location. As such, in this Example B3, in zone 209, a portion of ethylbenzene and C9+C2+-hydrocarbyl-substituted aromatic hydrocarbons are converted to benzene and toluene. As such, the xylenes stream 117 and the p-xylene-depleted streams 123 in in this Example comprise ethylbenzene at a reduced concentration compared to their corresponding streams in FIG. 1. Deethylation and vapor-phase isomerization of stream 123 becomes unnecessary. As such, in this Example B3, the entirety of stream 123 is fed into a liquid-phase isomerization zone 125, similar to Example B2. Similar to Example B2, in this Example B3, the isomerization effluent 217, in turn, is supplied to the xylenes splitter 115 in its entirety. Additional process assumptions and simulation results are reported in TABLE I below.

TABLE I

| | | Example | | |
|---|---|---|---|---|
| | | B1 | B2 | B3 |
| Yield Assumptions in Zone 209 | Ethyl Conversion (%) | n/a | 90 | 85 |
| | C3-Alkyl Conversion (%) | n/a | 100 | 100 |
| | Methyl Conversion | n/a | 3 | 0 |
| Process Assumptions in Zone 209 | Stream 213 recycle to Zone 209 (% of Stream 123) | n/a | 4 | 4 |
| Performance | Nominal p-Xylene Production (KTA) | 1 | 1.09 | 1 |
| | p-Xylene/Feed (wt %) | 57 | 62 | 57 |
| | Benzene/Feed (wt %) | 20 | 16 | 20 |
| | (p-Xylene + Benzene)/Feed (wt %) | 77 | 78 | 77 |
| | (Liquid Products)/Feed (wt %) | 94 | 96 | 94 |

Data in TABLE I clearly shows the superiority of the inventive process of Example B2 over the comparative processes in comparative Examples B1 and B3. In terms of nominal p-xylene production, for every 1 kilotons per annum ("KTA") produced in Examples B1 and B3, 1.09 KTA of p-xylene is produced in the inventive process of Example B2 from the same quantity of feed material having the same composition, representing a 9% of increase. The increase in p-xylene production is partly achieved by a reduced production of benzene. The total weight percentage of p-xylene and benzene relative to the feed, and the total weight percentage of liquid products relative to the feed both increased in the inventive process of Example B2. Correspondingly, total percentages gas products, typically of low value, decreased in the inventive process of Example B2 compared to those in Examples B1 and B3. These data clearly demonstrate the advantages and higher economic value of the alkyl-demethylation zone over the use of dealkylation either before the xylenes loop or in a vapor-phase isomerization step in the xylenes loop.

Examples B4-B7: Ethyl-Demethylation of Ethylbenzene in the Context of Isomerization In these examples, a feed comprising 87 wt % xylenes and 13 wt % ethylbenzene, simulating a p-xylene-depleted stream 123 in FIG. 5 was contacted with an ethyl-demethylation catalyst in an ethyl-demethylation reactor 503. The effluent from the ethyl-demethylation reactor was analyzed for compositions. The catalysts prepared in Examples A1, A3, A4 and A6 were tested in these examples. Process conditions and test results are reported in TABLE II below.

TABLE II

| | | Example No. | | | |
|---|---|---|---|---|---|
| | | B4 | B5 | B6 | B7 |
| Catalyst | of Example | A1 | A3 | A4 | A6 |
| | Rh Loading (wt %) | 0.1 | 0.9 | 1.8 | 3.5 |
| Process Conditions | WHSV (hr$^{-1}$) | 5.0 | 5.0 | 5.0 | 8.0 |
| | H$_2$:HC (molar) | 8.4 | 2.2 | 2.2 | 2.2 |
| | Pressure (psig) | 148 | 95 | 73 | 149 |
| | Temperature (° C.) | 379 | 382 | 380 | 377 |
| Conversion (%) | Ethylbenzene | 21 | 78 | 97 | 87 |
| | Xylene | 3 | 21 | 39 | 35 |
| | Ethylbenzene/Xylene | 6.50 | 3.69 | 2.47 | 2.47 |
| Aromatic Ring Loss (%) | | 1 | 0 | 0 | 4 |
| Product Selectivity (%) | Toluene | 87 | 81 | 74 | 83 |
| | Benzene | 3 | 6 | 15 | 0 |
| | Methane | 10 | 13 | 11 | 17 |

Data in TABLE II show that the alkyl-demethylation catalysts and processes in Examples B4-B7 achieved significantly higher conversion of ethylbenzene (desired) than xylenes (undesired). High product selectivity towards toluene (desired product) was achieved, and further demethylation of toluene to benzene, and aromatic ring loss are minimized. Therefore, the catalysts and process conditions in these Examples B4-B7 can be deployed in the ethyl-demethylation zones 503 and/or 507 in the process of FIG. 5.

This is in contrast with the disclosure in U.S. Pat. No. 4,331,825 where significant conversion of xylenes (undesired) and high selectivity towards methane (undesired) was observed.

Example B8: Alkyl-Demethylation of a Transalkylation Feed Comprising C9+C2+-Hydrocarbyl-Substituted Aromatic Hydrocarbons In this example, a feed mixture, representative of feed to a transalkylation zone, comprising approximately 80% C9+ aromatics (representative of feed 133 in the process of FIG. 6) and 20% toluene (representative of feed 146 in the process of FIG. 6), was fed into an alkyl-demethylation reactor (zone 605 in FIG. 6) to contact an alkyl-demethylation catalyst prepared in Example A6 above. Process conditions included temperature ranging from 380 to 405° C., a pressure of 103 psig, WHSV: ranging from 2.5 to 20 hr$^{-1}$, and H$_2$/hydrocarbon molar ratio ranging from 2-6. The process conditions were varied during the experiment to achieve differing levels of conversions of the C9+ aromatics components. The effluent from the reactor was analyzed for its composition. Partial test conditions and results are reported in TABLE III below. Methane was found to be present, while ethane and propane absent, in the effluent, indicating the conversion of ethyl-aromatics and C3-alkyl-aromatics by alkyl-demethylation reactions instead of dealkylation reactions.

Data in TABLE III show that the alkyl-demethylation catalysts and processes in this Example B8 achieved significantly higher conversion of ethyl-aromatics and propyl-aromatics (desired) than trimethylbenzenes (undesired). Therefore, the catalysts and process conditions in this example can be deployed in alkyl-demethylation zones 603, 605, and/or 609 in the process of FIG. 6.

Examples B9-B10: Alkyl-Demethylation of C9+C2+-Hydrocarbyl Substituted Aromatic Hydrocarbon Transalkylation Feeds The same procedure in Example B8 was carried out in these examples, except that the alkyl-demethylation catalyst used in Example B8 was replaced by the catalysts prepared in Examples A7 and A8 in Examples B9 and B10, respectively. In Examples B9-B10, similar to Example B8, significantly higher ethyl-aromatics conversion and C3-alkyl-aromatics conversion than trimethylbenzenes conversion were observed. Partial test results of Examples B9 and B10 are also included in TABLE III below. Methane was found to be present, while ethane and propane absent, in the effluent, indicating the conversion of ethyl-aromatics and C3-alkyl-aromatics by alkyl-demethylation reactions instead of dealkylation reactions.

TABLE III

| Example | Catalyst | Process Condition | Conversion (%) | | | Ratio of Conversion | |
|---|---|---|---|---|---|---|---|
| | | | C2-A | C3-A | TMZ | C2-A/TMZ | C3-A/TMZ |
| B8 | A6 Rh(3.5%)/ Alumina (gamma) | I | 52.4 | 62.5 | 28.3 | 1.8 | 2.2 |
| | | II | 48.8 | 58.1 | 25.6 | 1.9 | 2.3 |
| | | III | 33.8 | 54.0 | 22.8 | 1.5 | 2.4 |
| B9 | A7 Rh(3.5%)/ La-Alumina (gamma) | I | 71.8 | 79.1 | 42.9 | 1.7 | 1.8 |
| | | II | 62.7 | 71.8 | 35.5 | 1.8 | 2.0 |
| | | III | 35.0 | 42.1 | 16.0 | 2.2 | 2.6 |
| B10 | A8 Rh(3.5%)/ La-Alumina (theta) | I | 55.3 | 65.2 | 29.0 | 1.9 | 2.2 |
| | | II | 44.2 | 55.1 | 22.9 | 1.9 | 2.4 |
| | | III | 17.2 | 22.8 | 3.5 | 4.9 | 6.4 |

The present disclosure can further include the following non-limiting embodiments:

A1. A process for making xylenes, the process comprising:

(I) providing a C6+ aromatic hydrocarbon-containing stream comprising a C2+-hydrocarbyl-substituted aromatic hydrocarbon, wherein the C2+-hydrocarbyl-substituted aromatic hydrocarbon has (i) a C2+ alkyl substitute attached to an aromatic ring therein and/or (ii) an aliphatic ring annelated to an aromatic ring therein;

(II) optionally contacting the C6+ aromatic hydrocarbon-containing stream with a first alkyl-demethylation catalyst in a first alkyl-demethylation zone under a first set of alkyl-demethylation conditions to convert at least a portion of the C2+-hydrocarbyl-substituted aromatic hydrocarbon to an alkyl-demethylated aromatic hydrocarbon to obtain an optional first alkyl-demethylated effluent exiting the first alkyl-demethylation zone;

(III) separating at least a portion of the C6+ aromatic hydrocarbon-containing stream and/or the first alkyl-demethylated effluent in a first separation apparatus to obtain a C6-C7 hydrocarbons-rich stream and a first C8+ aromatic hydrocarbons-rich stream;

(IV) optionally contacting the first C8+ aromatic hydrocarbons-rich stream with a second alkyl-demethylation catalyst in a second alkyl-demethylation zone under a second set of alkyl-demethylation conditions to convert at least a portion of the C2+-hydrocarbyl-substituted aromatic hydrocarbon, if any, contained in the first C8+ aromatic hydrocarbons-rich stream to an alkyl-demethylated aromatic hydrocarbon to obtain an optional second alkyl-demethylated effluent exiting the second alkyl-demethylation zone;

(V) separating at least a portion of the first C8+ aromatic hydrocarbons-rich stream and/or the second alkyl-demethylated effluent in a second separation apparatus to obtain a xylenes-rich stream and a C9+ aromatic hydrocarbons-rich stream; and (VI) optionally separating the xylenes-rich stream in a first p-xylene recovery sub-system to obtain a first p-xylene product stream and a first p-xylene depleted stream; wherein at least one of steps (II) and (IV) is carried out.

A2. The process of A1, wherein:
the C2+-hydrocarbyl-substituted aromatic hydrocarbon comprises ethylbenzene, ethylmethylbenzenes, n-propylbenzene, cumene, diethylbenzenes, n-propylmethylbenzenes, isopropylmethylbenzenes, ethyldimethylbenzenes, n-butylbenzene, sec-butylbenzene, isobutylbenzene, tert-butylbenzene, indane, indene, methylindanes, tetralin, and mixtures thereof.

A3. The process of A1 or A2, wherein the C2+-hydrocarbyl-substituted aromatic hydrocarbon has a total concentration in a range from 2 to 70 wt %, based on the total weight of the C6+ aromatic hydrocarbons contained in the C6+ aromatic hydrocarbon-containing stream.

A4. The process of A2 or A3, wherein the C2+-hydrocarbyl-substituted aromatic hydrocarbon comprises ethylbenzene at a concentration in a range from 2% to 50 wt %, based on the total weight of the C8 aromatic hydrocarbons contained in the C6+ aromatic hydrocarbon-containing stream.

A5. The process of any of A2 to A4, wherein the C2+-hydrocarbyl-substituted aromatic hydrocarbon comprises a C9 aromatic hydrocarbon portion thereof, and the C9 aromatic hydrocarbon portion has a total concentration in a range from 30 to 90 wt %, based on the total weight of the C9 aromatic hydrocarbons contained in the C6+ aromatic hydrocarbon-containing stream.

A6. The process of any of A1 to A5, wherein step (VI) is carried out, and the process further comprises:

(VII) optionally contacting at least a portion of the first p-xylene-depleted stream with a third alkyl-demethylation catalyst in a third alkyl-demethylation zone under a third set of alkyl-demethylation conditions to convert at least a portion of the C2+-hydrocarbyl-substituted aromatic hydrocarbon, if any, contained in the first p-xylene-depleted stream to an alkyl-demethylated aromatic hydrocarbon to obtain an optional third alkyl-demethylated effluent exiting the third alkyl-demethylation zone;

(VIII) contacting at least a portion of the first p-xylene-depleted stream and/or at least a portion of the third alkyl-demethylated effluent with an isomerization catalyst in a first isomerization zone under isomerization conditions to produce a first isomerization effluent exiting the first isomerization zone comprising p-xylene at a concentration higher than the first p-xylene-depleted stream; and (IX) separating at least a portion of the first isomerization effluent in a second p-xylene recovery sub-system to obtain a second p-xylene product stream and a second p-xylene depleted stream.

A7. The process of A6, wherein step (VII) is carried out, and the first isomerization zone is downstream of the third alkyl-demethylation zone.

A8. The process of A7, further comprising:

(VIIIa) contacting at least a portion of the first p-xylene-depleted stream and/or at least a portion of the third alkyl-demethylated effluent with a fourth alkyl-demethylation catalyst in the first isomerization zone under a fourth set of alkyl-demethylation conditions to convert at least a portion of the C2+-hydrocarbyl-substituted aromatic hydrocarbon, if any, contained in the first p-xylene-depleted stream and/or the third alkyl-demethylated effluent to an alkyl-demethylated aromatic hydrocarbon.

A9. The process of A6, wherein the first isomerization zone at least partly overlaps with the third alkyl-demethylation zone.

A10. The process of A6, wherein the second p-xylene recovery sub-system is the first p-xylene recovery sub-system, the first and second p-xylene product streams are parts of a joint stream, and the first and second p-xylene-depleted streams are parts of a joint stream.

A11. The process of any of A6 to A10, wherein liquid-phase isomerization is conducted in the first isomerization zone.

A12. The process of A11, wherein in step (VIII), substantially all of the third alkyl-demethylated effluent is fed to the first isomerization zone.

A13. The process of any of A6 to A10, wherein the isomerization conditions comprise maintaining the xylenes substantially in vapor phase in the first isomerization zone.

A14. The process of A13, wherein in step (VIII), a first portion of the p-xylene-depleted stream or a portion of the third alkyl-methylated effluent is fed to the first isomerization zone, and the process further comprises:

(VIIIb) contacting a second portion of the third alkyl-methylated effluent with a second isomerization catalyst in a second isomerization zone under a second set of isomerization conditions sufficient to effect vapor-phase isomerization to produce a second isomerization effluent; and (VIIIc) separating at least at least a portion of the second isomerization effluent in the second p-xylene recovery sub-system to obtain the second p-xylene product stream and the second p-xylene depleted stream.

A15. The process of any of A1 to A14, further comprising:

(X) optionally contacting at least a portion of the C9+ aromatic hydrocarbons-rich stream with a fifth alkyl-demethylation catalyst in a fifth alkyl-demethylation zone under a fifth set of alkyl-demethylation conditions to convert at least a portion of the C2+-hydrocarbyl-substituted aromatic hydrocarbon, if any, contained in the C9+ aromatic hydrocarbons-rich stream to an alkyl-demethylated hydrocarbon to produce a fifth alkyl-demethylated effluent exiting the fifth alkyl-demethylation zone;

(XI) optionally separating the C9+ aromatic hydrocarbons-rich stream and/or the fifth alkyl-demethylated effluent in a third separation apparatus to obtain a C9-C10 aromatic hydrocarbons-rich stream and a C11+ aromatic hydrocarbons-rich stream;

(XII) optionally contacting at least a portion of the C9+ aromatic hydrocarbon stream, and/or at least a portion of the fifth alkyl-demethylated effluent, and/or at least a portion of the C9-C10 aromatic hydrocarbons-rich stream with a sixth alkyl-demethylation catalyst in a sixth alkyl-demethylation zone under a sixth set of alkyl-demethylation conditions to convert at least a portion of the C2+-hydrocarbyl-substituted aromatic hydrocarbon, if any, contained in the C9+ aromatic hydrocarbon stream, and/or the fifth alkyl-demethylated effluent, and/or the C9-C10 aromatic hydrocarbons-rich stream to an alkyl-demethylated hydrocarbon to produce a sixth alkyl-demethylated effluent exiting the sixth alkyl-demethylation zone;

(XIII) feeding at least a portion of the C9+ aromatic hydrocarbons-rich stream, and/or at least a portion of the fifth alkyl-demethylated effluent, and/or at least a portion of the C9-C10 aromatic hydrocarbons-rich stream, and/or at least a portion of the sixth alkyl-demethylated effluent, and optionally a benzene/toluene stream to a transalkylation zone;

(XIV) contacting C9+ aromatic hydrocarbons with benzene/toluene in the presence of a transalkylation catalyst under transalkylation conditions to produce a transalkylation effluent exiting the transalkylation zone; and (XV) separating the transalkylation effluent in a fourth separation apparatus to obtain an optional first benzene product stream, a toluene-rich stream, and a second C8+ aromatic hydrocarbons-rich stream.

A16. The process of A15, further comprising:
(XVI) feeding the second C8+ aromatic hydrocarbons-rich stream, along with the first C8+ aromatic hydrocarbons-rich stream, to the second separation apparatus.

A17. The process of A15 or A16, further comprising:
(XVII) feeding at least a portion of the first benzene product stream and/or at least a portion of the toluene-rich stream to the transalkylation zone as at least a portion of the benzene/toluene stream.

A18. The process of any of A15 to a17, wherein the sixth alkyl-demethylation zone is upstream of the transalkylation zone.

A19. The process of any of A15 to A17, wherein the sixth alkyl-demethylation zone at least partly overlaps with the transalkylation zone.

A20. The process of any of A1 to A19, further comprising:
(XVIII) obtaining a first C6-C7 aromatic hydrocarbons-rich stream from the C6-C7 hydrocarbons-rich stream; and
(XIX) separating the first C6-C7 aromatic hydrocarbons-rich stream in a fifth separation apparatus to obtain a second benzene product stream, and a second toluene-rich stream.

A21. The process of A20, wherein the fifth separation apparatus is the fourth separation apparatus, the first and the second benzene product streams are a joint stream, and the first and second toluene-rich streams are a joint stream.

A22. The process of any of A15 to A21, further comprising:
(XX) contacting at least a portion of the first toluene-rich stream and/or at least a portion of the second toluene-rich stream with a disproportionation catalyst in a disproportionation zone under disproportionation conditions to produce a disproportionation effluent exiting the disproportionation zone comprising p-xylene;
(XXI) separating at least a portion of the disproportionation effluent in a sixth separation apparatus to obtain a third p-xylene-rich stream and a third toluene-rich stream; and
(XXII) optionally recycling at least a portion of the third toluene-rich stream to the disproportionation zone.

A23. The process of any of A15 to A21, wherein the sixth separation apparatus and/or the fifth separation apparatus and/or the fourth separation apparatus are the same apparatus, the third p-xylene-rich stream, and/or the first C8+ aromatic hydrocarbons-rich stream, and/or the second C8+ aromatic hydrocarbons-rich stream are parts of a joint stream, and the first toluene-rich stream, and/or the second toluene-rich stream, and/or the third toluene are parts of a join stream.

A24. The process of A22, further comprising:
(XXIII) separating the third p-xylene-rich stream in a third p-xylene recovery sub-system to obtain a third p-xylene product stream and a third p-xylene depleted stream.

A25. The process of any of A15 to A24, further comprising:
(XXIV) contacting at least a portion of the first benzene product stream, and/or at least a portion of the second benzene product stream, and/or at least a portion of the first toluene-rich stream, and/or at least a portion of the second toluene-rich stream, and/or at least a portion of the third toluene-rich stream with methanol and/or dimethyl ether in the presence of an alkylation catalyst in an alkylation zone under alkylation conditions to produce an alkylation effluent exiting the alkylation zone comprising p-xylene;

(XXV) separating at least a portion of the alkylation effluent to obtain a fourth p-xylene-rich stream and a fourth toluene-rich stream; and (XXVI) separating the fourth p-xylene-rich stream in a fourth p-xylene recovery sub-system to obtain a fourth p-xylene product stream and a fourth p-xylene depleted stream.

A26. The process of A23 or A24, wherein the third and fourth p-xylene recovery sub-systems are the same sub-system, and the third and fourth p-xylene product streams are parts of a joint stream.

A27. The process of A24 or A25, wherein the third p-xylene recovery sub-system and/or the fourth p-xylene recovery system comprise a crystallizer.

A28. The process of any of A1 to A27, wherein step (I) comprises:
(Ia) providing a heavy naphtha stream;
(Ib) contacting the heavy naphtha stream with a reforming catalyst in a reforming zone under reforming conditions to obtain a reforming effluent comprising C6+ aromatic hydrocarbons exiting the reforming zone, wherein at least a portion of the C2+-hydrocarbyl-substituted aromatic hydrocarbon is produced in this step (Ib); and
(Ic) providing at least a portion of the reforming effluent as at least a portion of the C6+ aromatic hydrocarbon-containing stream.

A29. The process of A28, further comprising:
(Id) contacting the heavy naphtha stream and/or an intermediate reaction mixture with a seventh alkyl-demethylation catalyst in the reforming zone under a seventh set of alkyl-demethylation conditions to convert at least a portion of the C2+-hydrocarbyl-substituted aromatic hydrocarbon to an alkyl-demethylated aromatic hydrocarbon.

A30. The process of A28 or A29, wherein the first alkyl-demethylation zone is downstream of the reforming zone and/or the seventh alkyl-demethylation zone.

A31. The process of A28 or A29, wherein the first alkyl-demethylation zone overlaps at least partly with the reforming zone and/or the seventh alkyl-demethylation zone.

A32. The process of any of A1 to A31, wherein at least a portion of the first C6+ aromatic hydrocarbons-containing stream is derived from a hydrotreated steam-cracked naphtha stream.

A33. The process of A32, wherein a C5− hydrocarbon-rich stream is obtained in step (III).

A34. The process of any of A1 to A33, wherein the first alkyl-demethylation catalyst, and/or the second alkyl-demethylation catalyst, and/or the third alkyl-demethylation catalyst, and/or the fourth alkyl-demethylation catalyst, and/or the fifth alkyl-demethylation catalyst, and/or the six alkyl-demethylation catalyst, and/or the seventh alkyl-demethylation catalyst, the same or different, comprise a first metal element selected from groups 7, 8, 9, and 10 metals and combinations thereof, and a support.

A35. The process of A34, wherein the first metal element is selected from Fe, Co, Ni, Cu, Ru, Rh, Pd, Re, Os, Ir, Pt, and combinations thereof.

A36. The process of A34 or A35, wherein the concentration of the first metal element in the respective alkyl-demethylation catalyst is in a range from 0.1 to 10 wt %, based on the total weight of the respective alkyl-demethylation catalyst.

A37. The process of any of A34 to A36, wherein the first alkyl-demethylation catalyst, and/or the second alkyl-demethylation catalyst, and/or the third alkyl-demethylation catalyst, and/or the fourth alkyl-demethylation catalyst, and/or the fifth alkyl-demethylation catalyst, and/or the six alkyl-demethylation catalyst, and/or the seventh alkyl-demethylation catalyst, the same or different, further comprises a second metal element selected from groups 11, 12, 13, and 14 metals, and combinations thereof.

A38. The process of A37, wherein the second metal element is selected from Cu, Ag, Au, Zn, Al, Ga, Sn, and combinations thereof.

A39. The process of A37 or A38, wherein the concentration of the second metal element in the respective alkyl-demethylation catalyst is in a range from 0.1 to 10 wt %, based on the total weight of the respective alkyl-demethylation catalyst.

A40. The process of any of A34 to A39, wherein the first alkyl-demethylation catalyst, and/or the second alkyl-demethylation catalyst, and/or the third alkyl-demethylation catalyst, and/or the fourth alkyl-demethylation catalyst, and/or the fifth alkyl-demethylation catalyst, and/or the six alkyl-demethylation catalyst, and/or the seventh alkyl-demethylation catalyst, the same or different, further comprises a third metal element selected from groups 1 and 2 metals, and combinations thereof.

A41. The process of A40, wherein the third metal element is selected from Li, N, K, Rb, Cs, Mg, Ca, Ba, and combinations thereof.

A42. The process of A40 or A41, wherein the concentration of the third metal element in the respective alkyl-demethylation catalyst is in a range from 0.1 to 10 wt %, based on the total weight of the respective alkyl-demethylation catalyst.

A43. The process of any of A34 to A42, wherein at least one of the respective first, second, third, fourth, fifth, sixth, and seventh alkyl-demethylation catalysts comprises a molecular sieve (preferably a zeolite) as at least a portion of the support.

A44. The process of any of A1 to A43, wherein the first, second, third, fourth, fifth, sixth, and seventh sets of alkyl-demethylation conditions, the same or different, comprise at least one of the following:

a temperature in a range from 200 to 500° C.;

an absolute pressure in a range from 350 to 2500 kilopascal;

a molar ratio of molecular hydrogen to hydrocarbon in a range from 0.5 to 20; and a liquid weight hourly space velocity in a range from 1 to 20 hour$^{-1}$.

B1. A C8 aromatic hydrocarbon isomerization process, the process comprising:

(i) providing a first C8 aromatic hydrocarbon stream comprising ethylbenzene, p-xylene, m-xylene, and optionally o-xylene;

(ii) separating the first C8 aromatic hydrocarbon stream in a p-xylene recovery sub-system to obtain a p-xylene product stream and a p-xylene depleted stream;

(iii) contacting at least a portion of the p-xylene depleted stream with a first ethyl-demethylation catalyst in a first ethyl-demethylation zone to convert at least a portion of the ethylbenzene present in the p-xylene depleted stream to toluene to obtain a first ethyl-demethylation effluent exiting the first ethyl-demethylation zone;

(iv) contacting at least a portion of the p-xylene depleted stream and/or at least a portion of the first ethyl-demethylation effluent with a first xylenes isomerization catalyst in a first xylenes isomerization zone under a first set of xylenes isomerization conditions to obtain a first xylenes isomerization effluent; and (v) supplying at least a portion of the first xylenes isomerization effluent to the p-xylene recovery sub-system to obtain the p-xylene product stream and the p-xylene depleted stream.

B2. The C8 aromatic hydrocarbon isomerization process of B1, wherein the first xylenes isomerization zone is downstream of the first ethyl-demethylation zone.

B2a. The C8 aromatic hydrocarbon isomerization process of B2, further comprising:

(iva) contacting at least a portion of the p-xylene depleted stream and/or at least a portion of the first ethyl-demethylation effluent with a second ethyl-demethylation catalyst in the first xylenes isomerization zone under a second set of ethyl-demethylation conditions to convert at least a portion of the ethylbenzene present in the second isomerization zone to toluene.

B3. The C8 aromatic hydrocarbon isomerization process of B1, wherein the first xylenes isomerization zone at least partly overlaps with the first ethyl-demethylation zone.

B4. The C8 aromatic hydrocarbon isomerization process of any of B1 to B3, wherein liquid-phase isomerization is carried out in the first xylenes isomerization zone.

B5. The C8 aromatic hydrocarbon isomerization process of B4, wherein substantially all of the first ethyl-demethylation effluent is fed into the first xylenes isomerization zone.

B6. The C8 aromatic hydrocarbon isomerization process of B4 or B5, wherein the first set of xylenes isomerization conditions comprise an absence of a molecular hydrogen co-fed into the first isomerization zone.

B7. The C8 aromatic hydrocarbon isomerization process of any of B1 to B3, wherein vapor-phase isomerization is carried out in the first xylenes isomerization zone.

B8. The C8 aromatic hydrocarbon isomerization process of B7, wherein a first portion of the first ethyl-demethylation effluent is fed into the first xylenes isomerization zone, and the process further comprises:

(vi) contacting a second portion of the first ethyl-demethylation effluent with a second xylenes isomerization catalyst in a second xylenes isomerization zone under a second set of xylenes isomerization conditions to produce a second xylenes isomerization effluent, wherein liquid-phase isomerization is carried out in the second xylenes isomerization zone;

(vii) separating at least a portion of the second xylenes isomerization effluent in the p-xylene recovery sub-system to obtain the p-xylene product stream and the p-xylene depleted stream.

B9. The C8 aromatic hydrocarbon isomerization process of any of B1 to B8, further comprising:

(viii) conducting away a portion of the p-xylene-depleted stream as a first purge stream.

B10. The C8 aromatic hydrocarbon isomerization process of any of B1 to B7, further comprising:

(ix) conducting away a portion of the first isomerization effluent and/or a portion of the second isomerization effluent as a second purge stream.

B11. The process of any of B1 to B10, wherein the first ethyl-demethylation catalyst, and/or the second ethyl-demethylation catalyst, the same or different, comprise a first metal element selected from groups 7, 8, 9, and 10 metals and combinations thereof, and a support.

B12. The process of B11, wherein the first metal element is selected from Fe, Co, Ni, Cu, Ru, Rh, Pd, Re, Os, Ir, Pt, and combinations thereof.

B13. The process of B12 or B13, wherein the concentration of the first metal element in the respective ethyl-demethylation catalyst is in a range from 0.1 to 10 wt %, based on the total weight of the respective ethyl-demethylation catalyst.

B14. The process of any of B11 to B13, wherein the first ethyl-demethylation catalyst and/or the second ethyl-demethylation catalyst, the same or different, further comprises a second metal element selected from groups 11, 12, 13, and 14 metals, and combinations thereof.

B15. The process of B14, wherein the second metal element is selected from Cu, Ag, Au, Zn, Al, Ga, Sn, and combinations thereof.

B16. The process of B14 or B15, wherein the concentration of the second metal element in the respective ethyl-demethylation catalyst is in a range from 0.1 to 10 wt %, based on the total weight of the respective ethyl-demethylation catalyst.

B17. The process of any of B11 to B16, wherein the first ethyl-demethylation catalyst and/or the second ethyl-demethylation catalyst, the same or different, further comprises a third metal element selected from groups 1 and 2 metals, and combinations thereof.

B18. The process of B17, wherein the third metal element is selected from Li, N, K, Rb, Cs, Mg, Ca, Ba, and combinations thereof.

B19. The process of B17 or B18, wherein the concentration of the third metal element in the respective ethyl-demethylation catalyst is in a range from 0.1 to 10 wt %, based on the total weight of the respective ethyl-demethylation catalyst.

B20. The process of any of B1 to B19, wherein the first ethyl-demethylation catalyst and/or the second ethyl-demethylation catalyst, the same or different, comprises a molecular sieve, preferably a zeolite, as at least a portion of the support.

B21. The process of any of B1 to B19, wherein the first and second sets of alkyl-demethylation conditions, the same or different, comprise at least one of the following:

a temperature in a range from 200 to 500° C.;

an absolute pressure in a range from 350 to 2500 kilopascal;

a molar ratio of molecular hydrogen to hydrocarbon in a range from 0.5 to 20; and a liquid weight hourly space velocity in a range from 1 to 20 hour$^{-1}$.

B22. A process for converting C8 aromatic hydrocarbons, the process comprising:

(i) providing a first C8 aromatic hydrocarbon stream comprising ethylbenzene, p-xylene, m-xylene, and optionally o-xylene;

(ii) separating the first C8 aromatic hydrocarbon stream in a p-xylene recovery sub-system to obtain a p-xylene product stream and a p-xylene depleted stream;

(iii) contacting at least a portion of the p-xylene depleted stream with a first ethyl-demethylation catalyst in a first ethyl-demethylation zone under a first set of alkyl-demethylation conditions to convert at least a portion of the ethylbenzene present in the p-xylene depleted stream to toluene to obtain a first ethyl-demethylation effluent exiting the first ethyl-demethylation zone;

(iv) contacting at least a portion of the first ethyl-demethylation effluent and optionally at least a portion of the p-xylene depleted stream with a first xylenes isomerization catalyst in a first xylenes isomerization zone under a first set of xylenes isomerization conditions to obtain a first xylenes isomerization effluent; and (v) supplying at least a portion of the first xylenes isomerization effluent to the p-xylene recovery sub-system to obtain the p-xylene product stream and the p-xylene depleted stream;

wherein:

the first set of ethyl-demethylation conditions comprise: a temperature in a range from 200 to 500° C.; an absolute pressure in a range from 350 to 2500 kilopascal; a molar ratio of molecular hydrogen to hydrocarbon in a range from 0.5 to 20; and a liquid weight hourly space velocity in a range from 1 to 20 hour$^{-1}$; and the first ethyl-demethylation catalyst comprises a first metal element selected from groups 7, 8, 9, and 10 metals and combinations thereof, and a support.

C1. A transalkylation process, the process comprising:

(A) providing a C9+ aromatic hydrocarbon stream comprising a C2+-hydrocarbyl-substituted aromatic hydrocarbon, wherein the C2+-hydrocarbyl-substituted aromatic hydrocarbon has (i) a C2+ alkyl substitute attached to an aromatic ring therein and/or (ii) an aliphatic ring annelated to an aromatic ring therein;

(B) optionally contacting at least a portion of the C9+ aromatic hydrocarbon stream with an alkyl-demethylation catalyst No. 1 in an alkyl-demethylation zone No. 1 under a set of alkyl-demethylation conditions No. 1 to convert at least a portion of the C2+-hydrocarbyl-substituted aromatic hydrocarbon contained in the C9+ aromatic hydrocarbon stream to an alkyl-demethylated hydrocarbon to produce an alkyl-demethylated effluent No. 1 exiting the alkyl-demethylation zone No. 1;

(C) optionally separating the C9+ aromatic hydrocarbons stream and/or the alkyl-demethylated effluent No. 1 in a separation device No. 1 to obtain a C9-C10 aromatic hydrocarbons-rich stream and a C11+ aromatic hydrocarbons-rich stream;

(D) optionally contacting at least a portion of the alkyl-demethylated effluent No. 1 and/or at least a portion of the C9-C10 aromatic hydrocarbons-rich stream with an alkyl-demethylation catalyst No. 2 in an alkyl-demethylation zone No. 2 under a set of alkyl-demethylation conditions No. 2 to convert at least a portion of the C2+-hydrocarbyl-substituted aromatic hydrocarbon, if any, contained in the alkyl-demethylated effluent No. 1 and/or the C9-C10 aromatic hydrocarbons-rich stream to an alkyl-demethylated hydrocarbon to produce an alkyl-demethylated effluent No. 2 exiting the alkyl-demethylation zone No. 2;

(E) feeding at least a portion of the C9+ aromatic hydrocarbons stream, and/or at least a portion of the alkyl-demethylated effluent No. 1, and/or at least a portion of the C9-C10 aromatic hydrocarbons-rich stream, and/or at least a portion of the alkyl-demethylated effluent No. 2, and an optional benzene/toluene stream to a transalkylation zone;

(F) contacting C9+ aromatic hydrocarbons with benzene/toluene in the presence of a transalkylation catalyst in the transalkylation zone under transalkylation conditions to produce a transalkylation effluent exiting the transalkylation zone; and (G) separating the transalkylation effluent in a separation device No. 2 to obtain an optional benzene product stream, a toluene-rich stream, and a C8+ aromatic hydrocarbons-rich stream;
wherein at least one of steps (B) and (D) is carried out.

C2. The transalkylation process of C1, further comprising:
(H) separating at least a portion of the C8+ aromatic hydrocarbons-rich stream in a separation device No. 3 to obtain a xylenes-rich stream and a C9+ aromatic hydrocarbons-rich stream; and
(I) providing at least a portion of the C9+ aromatic hydrocarbons-rich stream as at least a portion of the C9+ aromatic hydrocarbon stream in step (A).

C3. The transalkylation process of C1, wherein step (B) is carried out.

C4. The transalkylation process of any of C1 to C3, wherein step (C) is carried out.

C5. The transalkylation process of C3, wherein step (C) is carried out, and the C9-C10 aromatic hydrocarbons-rich stream further comprises C7 and C8 aromatic hydrocarbons.

C6. The process of any of C1 to C5, further comprising:
(J) feeding at least a portion of the benzene product stream and/or at least a portion of the toluene-rich stream to the transalkylation zone as at least a portion of the benzene/toluene stream in step (E).

C7. The process of any of C1 to C6, wherein the alkyl-demethylation zone No. 2 is upstream of the transalkylation zone.

C8. The process of C4, further comprising:
contacting at least a portion of the alkyl-demethylated effluent No. 2 and/or at least a portion of the C9-C10 aromatic hydrocarbons-rich stream with an alkyl-demethylation catalyst No. 3 in an alkyl-demethylation zone No. 3 under a set of alkyl-demethylation conditions No. 3 to convert at least a portion of the C2+-hydrocarbyl-substituted aromatic hydrocarbon, if any, contained in the alkyl-demethylated effluent No. 2 and/or the C9-C10 aromatic hydrocarbons-rich stream to an alkyl-demethylated hydrocarbon, wherein the alkyl-demethylation zone No. 3 at least partly overlaps with the transalkylation zone.

C9. The process of any of C1 to C7, wherein the alkyl-demethylation zone No. 2 at least partly overlaps with the transalkylation zone.

C10. The process of any of C1 to C9, wherein the first alkyl-demethylation catalyst, and/or the second alkyl-demethylation catalyst, and/or the third alkyl-demethylation catalyst, the same or different, comprise a first metal element selected from groups 7, 8, 9, and 10 metals and combinations thereof, and a support.

C11. The process of C10, wherein the first metal element is selected from Fe, Co, Ni, Cu, Ru, Rh, Pd, Re, Os, Ir, Pt, and combinations thereof.

C12. The process of C10 or C11, wherein the concentration of the first metal element in the respective alkyl-demethylation catalyst is in a range from 0.1 to 10 wt %, based on the total weight of the respective alkyl-demethylation catalyst.

C13. The process of any of C10 to C12, wherein the first alkyl-demethylation catalyst, and/or the second alkyl-demethylation catalyst, and/or the third alkyl-demethylation catalyst, the same or different, further comprises a second metal element selected from groups 11, 12, 13, and 14 metals, and combinations thereof.

C14. The process of C13, wherein the second metal element is selected from Cu, Ag, Au, Zn, Al, Ga, Sn, and combinations thereof.

C15. The process of C13 or C14, wherein the concentration of the second metal element in the respective alkyl-demethylation catalyst is in a range from 0.1 to 10 wt %, based on the total weight of the respective alkyl-demethylation catalyst.

C16. The process of any of C10 to C15, wherein the first alkyl-demethylation catalyst and/or the second alkyl-demethylation catalyst, the same or different, further comprises a third metal element selected from groups 1 and 2 metals, and combinations thereof.

C17. The process of C16, wherein the third metal element is selected from Li, N, K, Rb, Cs, Mg, Ca, Ba, and combinations thereof.

C18. The process of C16 or C17, wherein the concentration of the third metal element in the respective alkyl-demethylation catalyst is in a range from 0.1 to 10 wt %, based on the total weight of the respective alkyl-demethylation catalyst.

C19. The process of any of C10 to C18, wherein the first alkyl-demethylation catalyst, and/or the second alkyl-demethylation catalyst, and/or the third alkyl-demethylation catalyst, the same or different, comprises a molecular sieve as at least a portion of the support.

C20. The process of any of C1 to C19, wherein the set of alkyl-demethylation conditions No. 1, the set of alkyl-demethylation conditions No. 2, and the set of alkyl-demethylation conditions No. 3, the same or different, comprise at least one of:
a temperature in a range from 200 to 500° C.;
an absolute pressure in a range from 350 to 2500 kilopascal;
a molar ratio of molecular hydrogen to hydrocarbon in a range from 0.5 to 20; and
a liquid weight hourly space velocity in a range from 1 to 20 hour$^{-1}$.

C21. The process of C20, wherein liquid-phase transalkylation is carried out in the transalkylation zone.

C22. The process of C21, wherein the transalkylation conditions comprises the absence of a molecular hydrogen stream co-fed into the transalkylation zone.

C23. A process for converting aromatic hydrocarbons, the process comprising:
(A) providing a C9+ aromatic hydrocarbon stream comprising a C2+-hydrocarbyl-substituted aromatic hydrocarbon, wherein the C2+-hydrocarbyl-substituted aromatic hydrocarbon has (i) a C2+ alkyl substitute attached to an aromatic ring therein and/or (ii) an aliphatic ring annelated to an aromatic ring therein;
(B) optionally contacting at least a portion of the C9+ aromatic hydrocarbon stream with an alkyl-demethylation catalyst No. 1 in an alkyl-demethylation zone No. 1 under a set of alkyl-demethylation conditions No. 1 to convert at least a portion of the C2+-hydrocarbyl-substituted aromatic hydrocarbon contained in the C9+ aromatic hydrocarbon stream to an alkyl-demethylated hydrocarbon to produce an alkyl-demethylated effluent No. 1 exiting the alkyl-demethylation zone No. 1;
(C) optionally separating the C9+ aromatic hydrocarbons stream and/or the alkyl-demethylated effluent No. 1 in a separation device No. 1 to obtain a C9-C10 aromatic hydrocarbons-rich stream and a C11+ aromatic hydrocarbons-rich stream;
(D) optionally contacting at least a portion of the alkyl-demethylated effluent No. 1 and/or at least a portion of the C9-C10 aromatic hydrocarbons-rich stream with an alkyl-demethylation catalyst No. 2 in an alkyl-demethylation zone No. 2 under a set of alkyl-demethylation conditions No. 2 to convert at least a portion of the C2+-hydrocarbyl-substituted aromatic hydrocarbon, if any, contained in the alkyl-demethylated effluent No. 1 and/or the C9-C10 aromatic hydrocarbons-rich stream to an alkyl-demethylated hydrocarbon to produce an alkyl-demethylated effluent No. 2 exiting the alkyl-demethylation zone No. 2;

(E) feeding at least a portion of the C9+ aromatic hydrocarbons stream, and/or at least a portion of the alkyl-demethylated effluent No. 1, and/or at least a portion of the C9-C10 aromatic hydrocarbons-rich stream, and/or at least a portion of the alkyl-demethylated effluent No. 2, and an optional benzene/toluene stream to a transalkylation zone;

(F) contacting C9+ aromatic hydrocarbons with benzene/toluene in the presence of a transalkylation catalyst in the transalkylation zone under transalkylation conditions to produce a transalkylation effluent exiting the transalkylation zone; and (G) separating the transalkylation effluent in a separation device No. 2 to obtain an optional benzene product stream, a toluene-rich stream, and a C8+ aromatic hydrocarbons-rich stream;

wherein:
at least one of steps (B) and (D) is carried out;
the set of alkyl-demethylation conditions No. 1 and the set of alkyl-demethylation conditions No. 2, the same or different, comprise at least one of: a temperature in a range from 200 to 500° C.; an absolute pressure in a range from 350 to 2500 kilopascal; a molar ratio of molecular hydrogen to hydrocarbon in a range from 0.5 to 20; and a liquid weight hourly space velocity in a range from 1 to 20 hour$^{-1}$; and
the first alkyl-demethylation catalyst and/or the second alkyl-demethylation catalyst, the same or different, comprises a first metal element selected from groups 7, 8, 9, and 10 metals and combinations thereof, and a support.

D1. A catalyst composition for alkyl-demethylating an aromatic hydrocarbon having (i) a C2+ alkyl substitute attached to an aromatic ring therein and/or (ii) an aliphatic ring annelated to an aromatic ring therein, the catalyst composition comprising a first metal element selected from groups 7, 8, 9, and 10 metals and combinations thereof, and a support.

D2. The catalyst composition of D1, wherein the first metal element is selected from Fe, Co, Ni, Ru, Rh, Pd, Re, Os, Ir, Pt, and combinations thereof.

D3. The catalyst composition of D1 or D2, wherein the concentration of the first metal element in the catalyst composition is in a range 0.1 to 10 wt %, based on the total weight of the catalyst composition.

D4. The catalyst composition of D3, further comprising a second metal element selected from groups 11, 12, 13, and 14 metals, and combinations thereof.

D5. The catalyst composition of D4, wherein the second metal element is selected from Cu, Ag, Au, Zn, Al, Ga, Sn, and combinations thereof.

D6. The catalyst composition of D4 or D4, wherein the concentration of the second metal element in the respective alkyl-demethylation catalyst is in a range from 0.1 to 10 wt %, based on the total weight of the respective alkyl-demethylation catalyst.

D7. The catalyst composition of any of D1 to D6, further comprising a third metal element selected from Groups 1 and 2 metals, and combinations thereof.

D8. The catalyst composition of D7, wherein the third metal element is selected from Li, N, K, Rb, Cs, Mg, Ca, Ba, and combinations thereof.

D9. The catalyst composition of D7 or D8, wherein the concentration of the third metal element is in a range from 0.1 to 10 wt %, based on the total weight of the catalyst composition.

D10. The catalyst composition of any of D1 to D9, comprising a molecular sieve as at least a portion of the support.

D11. The catalyst composition of D10, wherein the molecular sieve comprises a zeolite.

D12. The catalyst composition of D10 or D11, wherein the molecular sieve has a specific area of $\geq 100$ m$^2$/g.

What is claimed is:

1. A transalkylation process, the process comprising:
(A) providing a C9+ aromatic hydrocarbon stream comprising a C2+-hydrocarbyl-substituted aromatic hydrocarbon, wherein the C2+-hydrocarbyl-substituted aromatic hydrocarbon has (i) a C2+ alkyl substitute attached to an aromatic ring therein and/or (ii) an aliphatic ring annelated to an aromatic ring therein;
(B) optionally contacting at least a portion of the C9+ aromatic hydrocarbon stream with an alkyl-demethylation catalyst No. 1 in an alkyl-demethylation zone No. 1 under a set of alkyl-demethylation conditions No. 1 to convert at least a portion of the C2+-hydrocarbyl-substituted aromatic hydrocarbon contained in the C9+ aromatic hydrocarbon stream to an alkyl-demethylated hydrocarbon to produce an alkyl-demethylated effluent No. 1 exiting the alkyl-demethylation zone No. 1;
(C) optionally separating the C9+ aromatic hydrocarbons stream and/or the alkyl-demethylated effluent No. 1 in a separation device No. 1 to obtain a C9-C10 aromatic hydrocarbons-rich stream and a C11+ aromatic hydrocarbons-rich stream;
(D) optionally contacting at least a portion of the alkyl-demethylated effluent No. 1 and/or at least a portion of the C9-C10 aromatic hydrocarbons-rich stream with an alkyl-demethylation catalyst No. 2 in an alkyl-demethylation zone No. 2 under a set of alkyl-demethylation conditions No. 2 to convert at least a portion of the C2+-hydrocarbyl-substituted aromatic hydrocarbon, if any, contained in the alkyl-demethylated effluent No. 1 and/or the C9-C10 aromatic hydrocarbons-rich stream to an alkyl-demethylated hydrocarbon to produce an alkyl-demethylated effluent No. 2 exiting the alkyl-demethylation zone No. 2;
(E) feeding at least a portion of the C9+ aromatic hydrocarbons stream, and/or at least a portion of the alkyl-demethylated effluent No. 1, and/or at least a portion of the C9-C10 aromatic hydrocarbons-rich stream, and/or at least a portion of the alkyl-demethylated effluent No. 2, and an optional benzene/toluene stream to a transalkylation zone;
(F) contacting C9+ aromatic hydrocarbons with benzene/toluene in the presence of a transalkylation catalyst in the transalkylation zone under transalkylation conditions to produce a transalkylation effluent exiting the transalkylation zone; and
(G) separating the transalkylation effluent in a separation device No. 2 to obtain an optional benzene product stream, a toluene-rich stream, and a C8+ aromatic hydrocarbons-rich stream;
wherein at least one of steps (B) and (D) is carried out.

2. The transalkylation process of claim 1, further comprising:
(H) separating at least a portion of the C8+ aromatic hydrocarbons-rich stream in a separation device No. 3 to obtain a xylenes-rich stream and a C9+ aromatic hydrocarbons-rich stream; and (I) providing at least a portion of the C9+ aromatic hydrocarbons-rich stream as at least a portion of the C9+ aromatic hydrocarbon stream in step (A).

3. The transalkylation process of claim 1, wherein step (B) is carried out.

4. The transalkylation process of claim 1, wherein step (C) is carried out.

5. The transalkylation process of claim 3, wherein step (C) is carried out, and the C9-C10 aromatic hydrocarbons-rich stream further comprises C7 and C8 aromatic hydrocarbons.

6. The process of claim 1, further comprising:

(J) feeding at least a portion of the benzene product stream and/or at least a portion of the toluene-rich stream to the transalkylation zone as at least a portion of the benzene/toluene stream in step (E).

7. The process of claim 1, wherein the alkyl-demethylation zone No. 2 is upstream of the transalkylation zone.

8. The process of claim 4, further comprising:

(K) contacting at least a portion of the alkyl-demethylated effluent No. 2 and/or at least a portion of the C9-C10 aromatic hydrocarbons-rich stream with an alkyl-demethylation catalyst No. 3 in an alkyl-demethylation zone No. 3 under a set of alkyl-demethylation conditions No. 3 to convert at least a portion of the C2+-hydrocarbyl-substituted aromatic hydrocarbon, if any, contained in the alkyl-demethylated effluent No. 2 and/or the C9-C10 aromatic hydrocarbons-rich stream to an alkyl-demethylated hydrocarbon, wherein the alkyl-demethylation zone No. 3 at least partly overlaps with the transalkylation zone.

9. The process of claim 1, wherein the alkyl-demethylation zone No. 2 at least partly overlaps with the transalkylation zone.

10. The process of claim 1, wherein the first alkyl-demethylation catalyst, and/or the second alkyl-demethylation catalyst, and/or the third alkyl-demethylation catalyst, the same or different, comprise a first metal element selected from groups 7, 8, 9, and 10 metals and combinations thereof, and a support.

11. The process of claim 10, wherein the first metal element is selected from Fe, Co, Ni, Cu, Ru, Rh, Pd, Re, Os, Ir, Pt, and combinations thereof.

12. The process of claim 10, wherein the concentration of the first metal element in the respective alkyl-demethylation catalyst is in a range from 0.1 to 10 wt %, based on the total weight of the respective alkyl-demethylation catalyst.

13. The process of claim 10, wherein the first alkyl-demethylation catalyst, and/or the second alkyl-demethylation catalyst, and/or the third alkyl-demethylation catalyst, the same or different, further comprises a second metal element selected from groups 11, 12, 13, and 14 metals, and combinations thereof.

14. The process of claim 13, wherein the second metal element is selected from Cu, Ag, Au, Zn, Al, Ga, Sn, and combinations thereof.

15. The process of claim 13, wherein the concentration of the second metal element in the respective alkyl-demethylation catalyst is in a range from 0.1 to 10 wt %, based on the total weight of the respective alkyl-demethylation catalyst.

16. The process of claim 10, wherein the first alkyl-demethylation catalyst and/or the second alkyl-demethylation catalyst, the same or different, further comprises a third metal element selected from groups 1 and 2 metals, and combinations thereof.

17. The process of claim 16, wherein the third metal element is selected from Li, N, K, Rb, Cs, Mg, Ca, Ba, and combinations thereof.

18. The process of claim 16, wherein the concentration of the third metal element in the respective alkyl-demethylation catalyst is in a range from 0.1 to 10 wt %, based on the total weight of the respective alkyl-demethylation catalyst.

19. The process of claim 10, wherein the first alkyl-demethylation catalyst, and/or the second alkyl-demethylation catalyst, and/or the third alkyl-demethylation catalyst, the same or different, comprises a molecular sieve as at least a portion of the support.

20. The process of claim 1, wherein the set of alkyl-demethylation conditions No. 1, the set of alkyl-demethylation conditions No. 2, and the set of alkyl-demethylation conditions No. 3, the same or different, comprise at least one of:

a temperature in a range from 200 to 500° C.;

an absolute pressure in a range from 350 to 2500 kilopascal;

a molar ratio of molecular hydrogen to hydrocarbon in a range from 0.5 to 20; and a liquid weight hourly space velocity in a range from 1 to 20 hour$^{-1}$.

21. The process of claim 20, wherein liquid-phase transalkylation is carried out in the transalkylation zone.

22. The process of claim 21, wherein the transalkylation conditions comprises the absence of a molecular hydrogen stream co-fed into the transalkylation zone.

23. A process for converting aromatic hydrocarbons, the process comprising:

(A) providing a C9+ aromatic hydrocarbon stream comprising a C2+-hydrocarbyl-substituted aromatic hydrocarbon, wherein the C2+-hydrocarbyl-substituted aromatic hydrocarbon has (i) a C2+ alkyl substitute attached to an aromatic ring therein and/or (ii) an aliphatic ring annelated to an aromatic ring therein;

(B) optionally contacting at least a portion of the C9+ aromatic hydrocarbon stream with an alkyl-demethylation catalyst No. 1 in an alkyl-demethylation zone No. 1 under a set of alkyl-demethylation conditions No. 1 to convert at least a portion of the C2+-hydrocarbyl-substituted aromatic hydrocarbon contained in the C9+ aromatic hydrocarbon stream to an alkyl-demethylated hydrocarbon to produce an alkyl-demethylated effluent No. 1 exiting the alkyl-demethylation zone No. 1;

(C) optionally separating the C9+ aromatic hydrocarbons stream and/or the alkyl-demethylated effluent No. 1 in a separation device No. 1 to obtain a C9-C10 aromatic hydrocarbons-rich stream and a C11+ aromatic hydrocarbons-rich stream;

(D) optionally contacting at least a portion of the alkyl-demethylated effluent No. 1 and/or at least a portion of the C9-C10 aromatic hydrocarbons-rich stream with an alkyl-demethylation catalyst No. 2 in an alkyl-demethylation zone No. 2 under a set of alkyl-demethylation conditions No. 2 to convert at least a portion of the C2+-hydrocarbyl-substituted aromatic hydrocarbon, if any, contained in the alkyl-demethylated effluent No. 1 and/or the C9-C10 aromatic hydrocarbons-rich stream to an alkyl-demethylated hydrocarbon to produce an alkyl-demethylated effluent No. 2 exiting the alkyl-demethylation zone No. 2;

(E) feeding at least a portion of the C9+ aromatic hydrocarbons stream, and/or at least a portion of the alkyl-demethylated effluent No. 1, and/or at least a portion of the C9-C10 aromatic hydrocarbons-rich stream, and/or at least a portion of the alkyl-demethylated effluent No. 2, and an optional benzene/toluene stream to a transalkylation zone;

(F) contacting C9+ aromatic hydrocarbons with benzene/toluene in the presence of a transalkylation catalyst in the transalkylation zone under transalkylation conditions to produce a transalkylation effluent exiting the transalkylation zone; and (G) separating the transalkylation effluent in a separation device No. 2 to obtain an optional benzene product stream, a toluene-rich stream, and a C8+ aromatic hydrocarbons-rich stream;

wherein:

at least one of steps (B) and (D) is carried out;

the set of alkyl-demethylation conditions No. 1 and the set of alkyl-demethylation conditions No. 2, the same or different, comprise at least one of: a temperature in a range from 200 to 500° C.; an absolute pressure in a range from 350 to 2500 kilopascal; a molar ratio of molecular hydrogen to hydrocarbon in a range from 0.5 to 20; and a liquid weight hourly space velocity in a range from 1 to 20 hour$^{-1}$; and the first alkyl-demethylation catalyst and/or the second alkyl-demethylation catalyst, the same or different, comprises a first metal element selected from groups 7, 8, 9, and 10 metals and combinations thereof, and a support.

* * * * *